(12) United States Patent
Manderville et al.

(10) Patent No.: US 11,215,619 B2
(45) Date of Patent: Jan. 4, 2022

(54) FLUORESCENT MEROCYANINE DYES, ASSOCIATED CONJUGATES AND METHODS

(71) Applicant: University of Guelph, Guelph (CA)

(72) Inventors: Richard Manderville, Guelph (CA); Micaela Gray, Tavistock (CA); Prashant Deore, Guelph (CA); Andrew Chung, Guelph (CA); Abigail Van Riesen, Guelph (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 16/884,927

(22) Filed: May 27, 2020

(65) Prior Publication Data

US 2020/0378979 A1 Dec. 3, 2020

Related U.S. Application Data

(60) Provisional application No. 62/855,414, filed on May 31, 2019.

(51) Int. Cl.
| | | |
|---|---|---|
| *G01N 33/58* | (2006.01) | |
| *G01N 21/77* | (2006.01) | |
| *C07D 401/06* | (2006.01) | |

(52) U.S. Cl.
CPC ......... *G01N 33/582* (2013.01); *C07D 401/06* (2013.01); *G01N 21/77* (2013.01)

(58) Field of Classification Search
CPC ..... G01N 33/582; G01N 21/77; C07D 401/06
See application file for complete search history.

(56) References Cited

PUBLICATIONS

Gu et al. Trimethine cyanine dyes with an indole nucleous: synthesis and spectral properties studies. Journal of Luminescence 2013, vol. 134, pp. 184-190. (Year: 2013).*

Schwechheimer et al. A new structure-activity relationship for cyanine dyes to improve photostability and fluorescence properties for live cell imaging. Chem. Sci. 2018, vol. 9, pp. 6557-6563. (Year: 2018).*
Kulinich, A., et al., "Merocyanine Dyes: Synthesis, Structure, Properties and Applications." Russ. Chem. Rev. 2009, 78 (2), 141-164.
Armitage, B. A., "Cyanine Dye-DNA Interactions: Intercalation, Groove Binding, and Aggregation." Top. Curr. Chem. 2005, 253, 55-76.
Zhang, D., et al., "Fluorescence Anisotropy Analysis for Mapping Aptamer—Protein Interaction at the Single Nucleotide Level." J. Am Chem Soc 2011, 133, 9188-9191.
Brooker, L. G. S., et al., "Color and Constitution. XIII. Merocyanines as Solvent Property Indicators." J. Am. Chem. Soc 1965, 87 (11), 2443-2450.
Wang, R. E., et al., "Aptamer-Based Fluorescent Biosensors." Curr. Med. Chem. 2011, 18 (27), 4175-4184.
Bohlander, P. R., et al., "Synthesis and Evaluation of Cyanine-Styryl Dyes with Enhanced Photostability for Fluorescent DNA Staining." Org. Biomol. Chem. 2013, 11 (43), 7458-7462.
Xu, W., et al., "Fluorescent Nucleobases as Tools for Studying DNA and RNA." Nat. Chem. 2017, 9, 1043-1055.
Deore, P. S., et al., "Ligand-Induced G-Quadruplex Polymorphism: A Dna Nanodevice for Label-Free Aptasensor Platforms." Journal of the American Chemical Society, 2019, 141, 14288-14297.
Gray, M., "Uncovering the Impact of a Fluorescent Merocyanine Probe on the Structure and Function of Aptamers for Protein and Small Molecule Detection." A Thesis presented to the University of Guelph, Guleph, Ontario, Canada, Nov. 2018.
Van Riesen, A., et al., "DNA Aptamer Toxin-binding Motif Revealed Using an Internal FRET Probe." Department of Chemistry and Toxicology, University of Guelph, Guelph, Ontario, Canada, N1G 2W1, Poster 2017.

* cited by examiner

*Primary Examiner* — Shafiqul Haq
(74) *Attorney, Agent, or Firm* — Bereskin & Parr LLP /S.E.N.C.R.L., s.r.l.; I. Laurence MacPhie

(57) ABSTRACT

Described are fluorescent merocyanine dyes useful as labels for the detection of target molecules. The dyes may be conjugated to a binding agent, such as an aptamer, or used in label-free assays. An exemplary merocyanine dye termed 4QI based on its 4-methylquinoline and indole heterocycle components is also described as well as phosphoramidite compounds and methods for the detection of targets.

20 Claims, 12 Drawing Sheets

Specification includes a Sequence Listing.

FLUORESCENT MEROCYANINE DYES, ASSOCIATED CONJUGATES AND METHODS

RELATED APPLICATIONS

This application claims the benefit of priority to U.S. Provisional Patent Application No. 62/855,414 filed May 31, 2019, the entire contents of which are hereby incorporated by reference.

INCORPORATION OF SEQUENCE LISTING

A computer readable form of the Sequence Listing "6580-P58804US01_SequenceListing.txt" (4,096 bytes), submitted via EFS-WEB and created on May 26, 2020, is herein incorporated by reference.

FIELD

The present disclosure relates to fluorescent merocyanine dyes and more specifically to fluorescent merocyanine dyes, associated conjugates and methods useful for labelling or detection of target molecules.

INTRODUCTION

Biosensors are increasingly popular for detecting and quantifying small molecule and protein targets. (Jayasena et al., 1999; Turner et al., 1989) Biosensors work to convert physio-chemical responses generated from interactions between target molecules and a biosensor recognition element into detectable signals. (Turner et al., 1989) Biosensor recognition elements sense and often bind to a target of interest, while the signal transducer produces a signal proportional to the sensor-target interaction. (Turner et al., 1989) For example, immunosensors have been developed to rely on specific antibody-antigen interactions to generate electrochemical, colorimetric, fluorescence or anisotropic signals.

Aptamers fold into well-defined three-dimensional shapes for target selectivity and affinity. (Jayasena et al., 1999) Owing to their target binding potential, aptamers are excellent biological recognition elements when coupled with a suitable signal transducer. DNA aptasensors are biosensors in which aptamers act as a signal transducer that produces an analytical signal upon binding to a small molecule or protein target. (Annamaria et al., 2016) Immunosensors and DNA aptasensors often generate the same types of signals. DNA aptasensors are relatively inexpensive, fast-acting and uncomplicated. (Jayasena et al., 1999; Annamaria et al., 2016) For example, DNA aptasensors have applications in biomarker detection, cancer screening, and therapeutic medicine. (Hong et al., 2012) DNA aptasensors also used in the detection of environmental pollutants. (Justino et al., 2017)

Various dyes have been developed for use with biosensors by acting as a signal transducer because of the dyes' inherent fluorescence and other optical properties. Bohländer and Wagenknect (Bohländer et al., 2013) reported in 2013 a quinoline-indole dye that are fluorescent in the visible region ($\lambda_{max}$=521 nm), has a large Stokes shift (133 nm) and is moderately bright ($\varepsilon$=30 800 $M^{-1}$ $cm^{-1}$).

There remains a need for fluorescent merocyanine dyes and associated methods useful for the labeling or detection of target molecules.

SUMMARY

In one aspect, there is provided a fluorescent compound of Formula I:

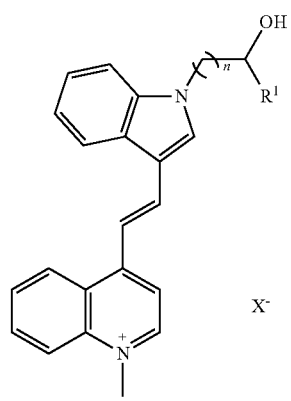

wherein $R^1$ is selected from H and $CH_2OH$, $X^-$ is a suitable counterion and n=1 or 2.

Also provided is a fluorescent phosphoramidite of Formula II:

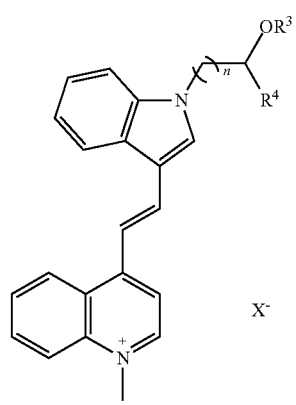

wherein $R^3$ is selected from a protective group and a phosphoramidite functionality, $R^4$ is selected from H and —$CH_2$Phosphoramidite, n=1 or 2, $X^-$ is a suitable counterion, when $R^4$ is H, $R^3$ is the phosphoramidite functionality and when $R^4$ is —$CH_2$Phosphoramidite, $R^3$ is the protective group.

In another aspect, there is also provided a fluorescently labelled nucleotide or polynucleotide of structure selected from Formulae V, VI, and VII:

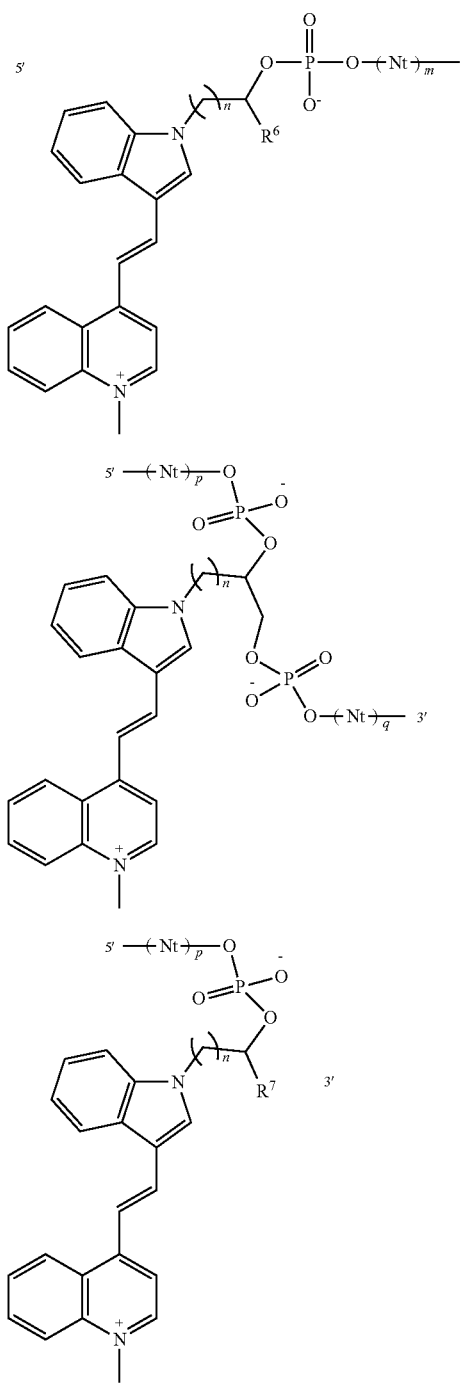

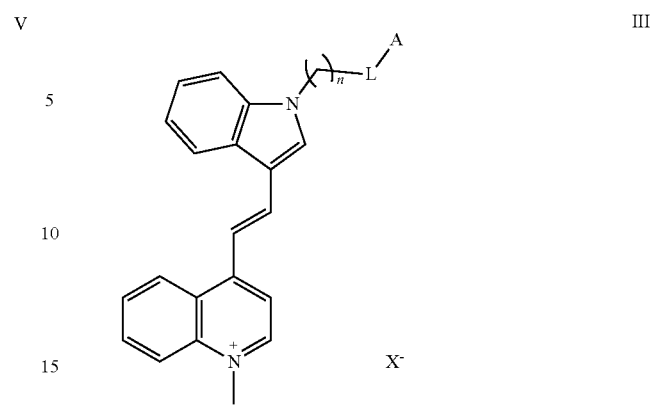

wherein $R^6$ and $R^7$ are independently selected from H and $CH_2OH$, n=1 or 2, m, p and q are independently an integer between 1 and 1000 and Nt is a nucleotide. In one embodiment, the polynucleotide is an aptamer that binds to a target.

Also provided is a fluorescent merocyanine compound as described herein, such as the fluorescent compound of Formula I conjugated to a substrate. In one embodiment, there is provided a compound of Formula III wherein L is an optional linker, A is a substrate, $X^-$ is an optional suitable counterion and n is an integer between 1 to 4.

In one embodiment, the substrate is a binding agent such as an aptamer, ligand or antibody. In one embodiment, the substrate is a biomolecule such as a polypeptide, polynucleotide, polysaccharide, lipid, carbohydrate, or organic molecule or a therapeutic agent such as a drug.

In another aspect, there are provided methods that use the fluorescent compounds described herein, such as the compounds of Formulae I-VII, for labelling and/or detecting a target.

In one embodiment, the fluorescent compounds of Formula I is used in combination with a binding agent for the detection of a target in a sample. For example, in one embodiment, there is provided a method comprising:

contacting the sample with the fluorescent compound of Formula I and a binding agent for the target, wherein binding of the binding agent to the target changes the optical properties of the fluorescent compound in the sample; and detecting a change in the optical properties of the fluorescent compound in the sample.

Optionally, in one embodiment the binding agent and the fluorescent compound are combined prior to contacting the sample.

In another embodiment, a fluorescently labelled polynucleotide of Formulae V, VI or VII or a fluorescent merocyanine compound of Formula III that comprises a binding agent is used to detect a target in a sample. For example, in one embodiment there is provided a method for detecting a target in a sample, the method comprising:

contacting the sample with the fluorescently labelled polynucleotide of Formulae V, VI or VII, or the compound of Formula III; and detecting the fluorescently labelled polynucleotide or the compound of Formula III bound to the target in the sample.

In one embodiment, the detecting the fluorescently labelled polynucleotide or compound bound to the target in the sample comprises detecting a change in one or more optical properties of the fluorescently labelled polynucleotide or fluorescent merocyanine compound. For example, in one embodiment, the method comprises detecting a change in absorbance, fluorescence or fluorescence polarization relative to a control.

In one embodiment, the method comprises detecting a fluorescent emission at one or more wavelengths between about 550 nm to 650 nm, about 580 nm to 600 nm, or about 590 nm in response to an excitation wavelength from about 450 nm to 550 nm, about 490 to 510 nm, or about 500 nm.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

DRAWINGS

Embodiments of the invention will now be described in relation to the drawings in which.

Figure 17:
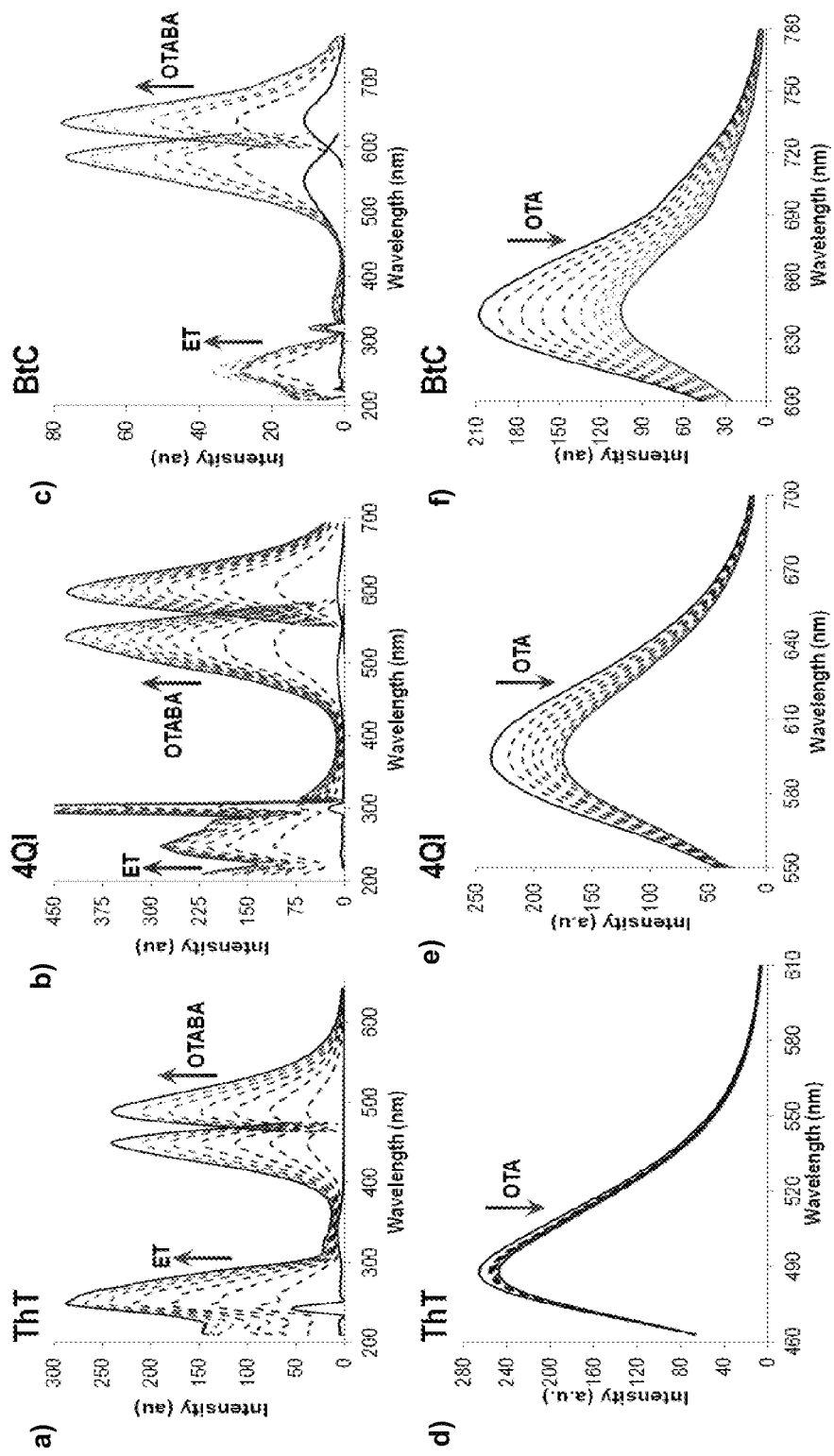

FIG. 17 shows fluorescent titrations of dye binding to OTABA (a, b and c) and dye displacement mediated by OTA (d, e and f) carried out at 25° C. in the OTA binding buffer (pH 8). For OTABA dye binding, the initial trace is depicted by the solid black line and represents free dye (6 µM), while dashed traces depict changes in dye emission/excitation upon successive addition of OTABA up to 1.5 equiv (9 µM). For OTA dis-placement, the initial solid black trace represents the 2:1 dye:OTABA complex (12:6 µM), while dashed traces represent changes in dye emission upon additions of OTA up to 1.5 equiv (9 µM).

Figure 18:
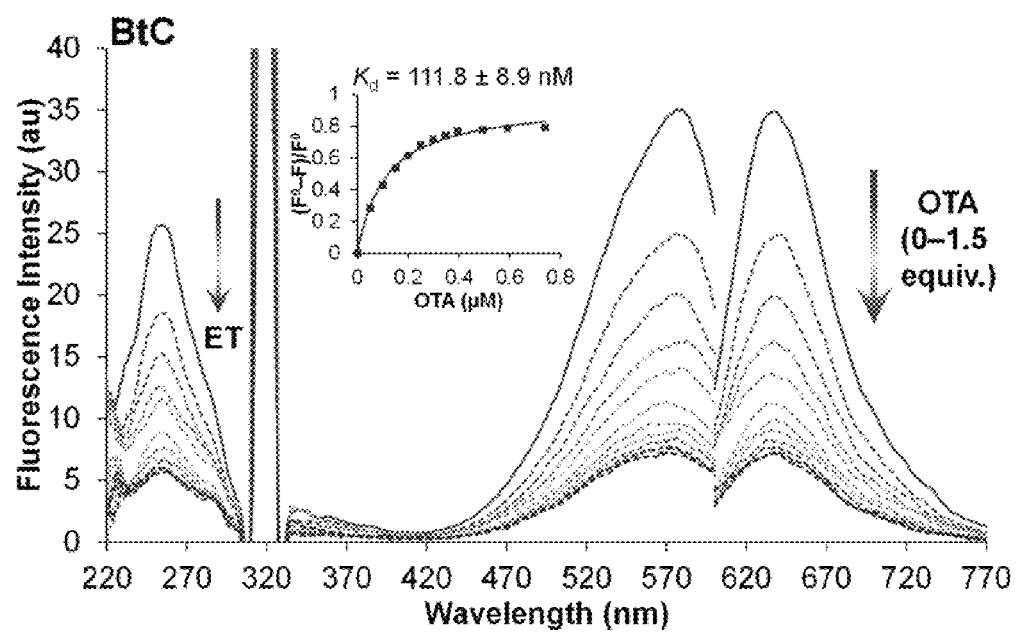

FIG. 18 shows fluorescence titration of the OTABA-BtC complex (solid green trace, 0.5 µM OTAA+1 µM BtC) with OTA (0-1.5 equiv., dotted green to red traces) in OTA binding buffer (pH 8.0) at 25° C. Insert displays the binding isotherm for the titration data.

Figure 19:
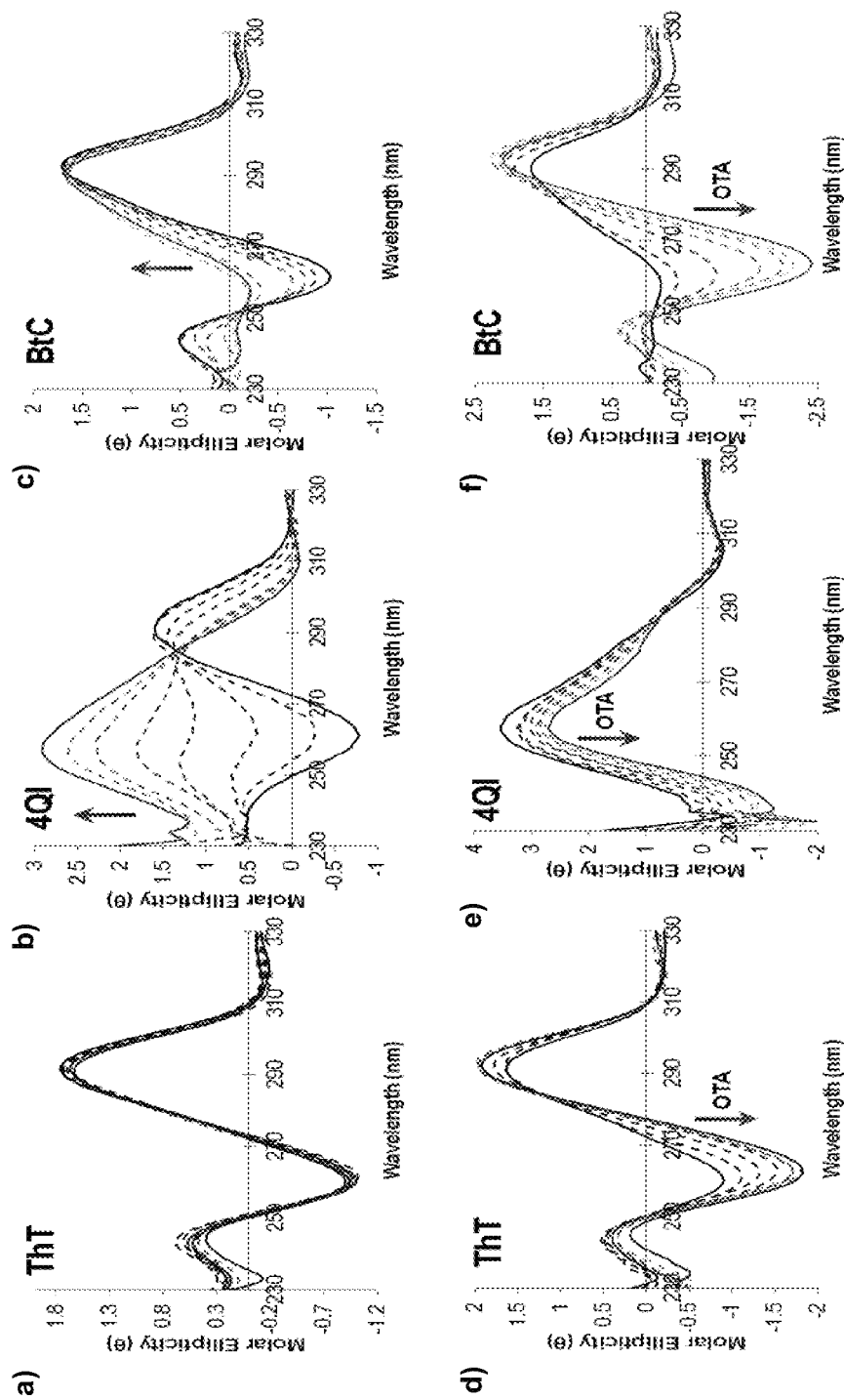

FIG. 19 shows CD titrations of dye binding to OTABA (a, b and c) and dye displacement mediated by OTA (d, e and f) carried out at 15° C. in the OTA binding buffer (pH 8). For dye binding, the initial trace is depicted by the solid black line and represents native OTABA (6 µM), while dashed traces depict changes in CD profile upon successive addition of dye up to 2 equiv (12 µM). For OTA displacement, the initial solid black trace represents the 2:1 dye:OTABA complex (12:6 µM), while dashed traces represent changes in CD profile upon additions of OTA up to 2 equiv (12 µM).

Figure 20:
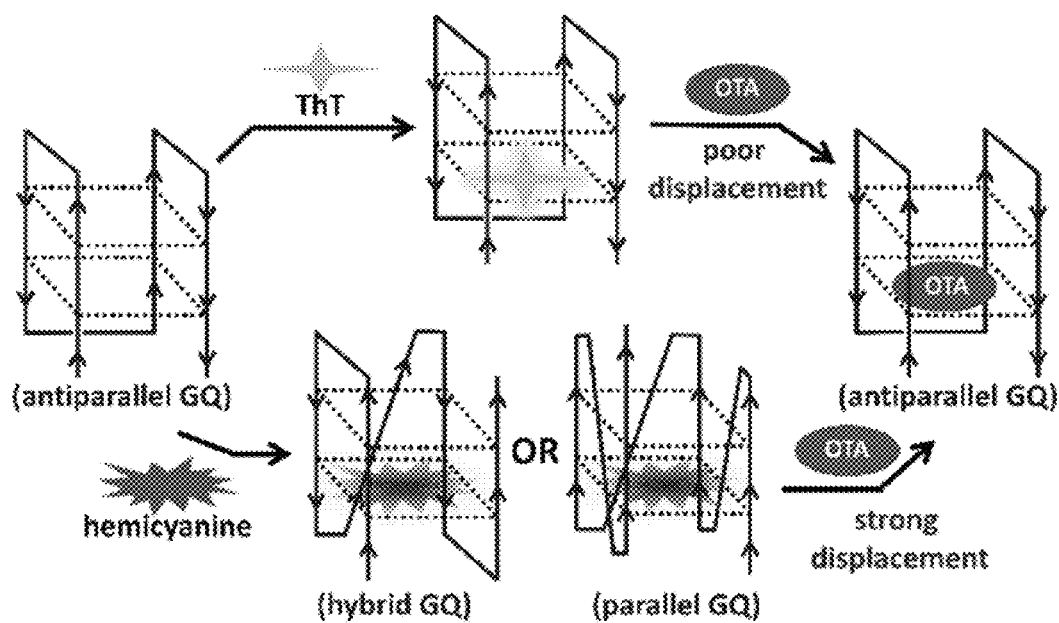

FIG. 20 shows an illustrative schematic for OTA-mediated dye displacement mechanism.

DESCRIPTION OF VARIOUS EMBODIMENTS

The embodiments described herein relate to merocyanine compounds that are useful as fluorescent labels and/or detection agents. In some embodiments, the merocyanine compounds are useful in combination with a binding agent for the detection of a target molecule. Optionally, the merocyanine compound may be conjugated to a binding agent (such as, but not limited to, an aptamer), or used in a label-free assay wherein the compound is free in solution.

Example 1 describes the synthesis of a number of fluorescent merocyanine compounds including compounds of Formula 1. Example 2 describes the incorporation of a specific cyanine-indole-quinolonium (4QI) compound into a thrombin-binding aptamer (TBA) as well as the label-free use of 4QI in combination with TBA for the detection of thrombin. Example 3 describes the incorporation of 4QI into an ochratoxin-A aptamer (OTAA) as well as the use of label-free use of 4QI in combination with OTAA for the detection of ochratoxin-A. Example 4 describes 4QI in a label-free aptasensor platform and ligand-induced G-Quadruplex polymorphism as a conformational switch with various dyes.

The 4QI dye was attached to a glycerol backbone and converted into a phosphoramidite for site-specific incorporation into DNA using solid phase DNA synthesis. The 4QI dye generates bright orange fluorescence at 590 nm, following excitation at 500 nm and was observed to be photostable within a DNA helix over a 6-month period in aqueous buffer at pH 7.4. In DNA, the dye exhibits bright emission at 590 nm that in one embodiment turns off upon aptamer binding to a target such as a protein or small molecule.

Most fluorescent signaling approaches for target detection by DNA aptamers utilize a complementary strand that can form a duplex with the DNA aptamer. Target binding to the aptamer displaces the complementary strand that may be detected by a change in optical properties such as fluorescence polarization or emission intensity, depending on the strategy employed to visualize the binding event, which may involve use of covalently attached end-labels, internal fluorescent probes, or label-free dyes. An issue with these assays is the need for optimization of the complementary strand for displacement that involves complex equilibria between duplex and the aptamer-target complex. Furthermore, the signal can be slow to develop as the target displaces the complementary strand.

The fluorescent merocyanine compounds described herein exhibit a number of advantageous characteristics for use in binding assays for the detection of target molecules such as with aptamers or other binding agents.

For example, in some embodiments the dye described herein only responds to target binding, which eliminates false-positive or -negative readouts and the dye response to the target is almost instantaneous. Furthermore, the red-shifted emission of 4QI at 590 nm and the stokes shift of 90 nm allows its application in difficult matrices, such as food components and blood with minimal sample pretreatment.

Accordingly, in one embodiment there is provided a fluorescent compound of Formula 1:

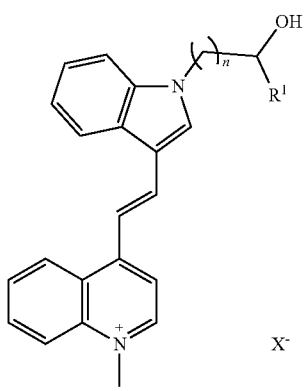

I wherein R is selected from H and $CH_2OH$; $X^-$ is a suitable counterion; and n=1 or 2.

In one embodiment, the fluorescent compound is selected from

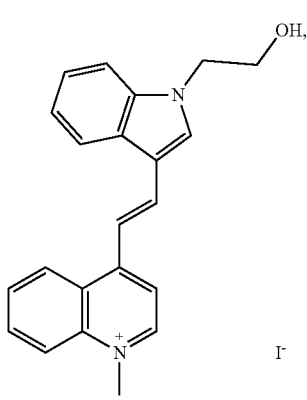

I-1

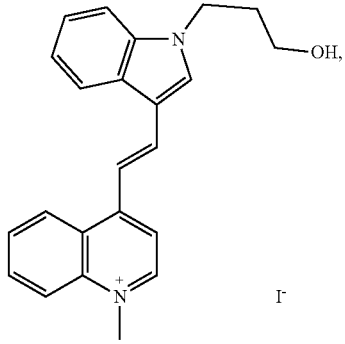

I-2

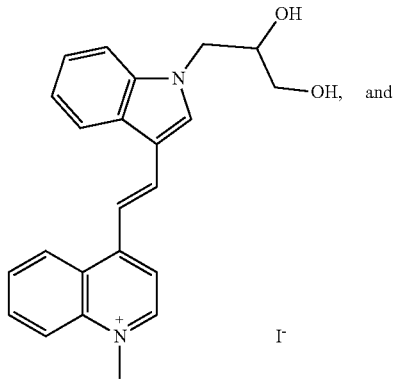

I-3 and

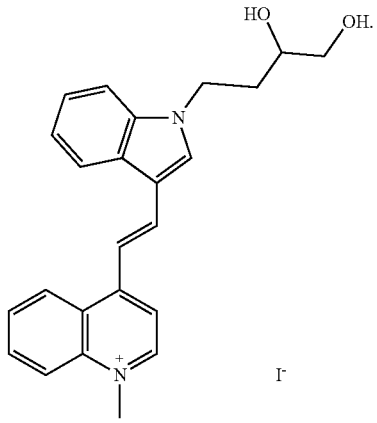

I-4

Examples of suitable counterions include iodide, bromide, fluoride, tosylate as well as other negatively charged ions that do not interfere with the fluorescent properties of the compounds described herein.

In one embodiment, the fluorescent compounds described herein are useful for labelling biomolecules such a nucleic acids. A common method for in vitro synthesis of polynucleotides is commonly known as the "phosphoramidite method" which involves building a nucleic acid polymer through the sequential addition of mononucleotides to a deoxyribonucleotide attached to a support (see for example Caruthers et al. 1987). During nucleic acid synthesis, the diisopropylamino group of an incoming phosphoramidite monomer may be activated by protonation using ETT (5-(ethylthio)-1H-tetrazole). The activated mononucleotide then reacts with the exposed 5'-OH of the previous nucleotide as it is added to the growing strand. This coupling results in a phosphite triester which is unstable and is therefore subsequently oxidized to a stable phosphate triester using diluted iodine in the presence of water and pyridine. Phosphoramidite compounds that contain a fluorescent merocyanine dye are therefore useful for labelling or the synthesis of nucleic acid molecules that contain a fluorescent merocyanine dye as described herein.

Accordingly, In one embodiment, there is provided a fluorescent phosphoramidite of Formula II

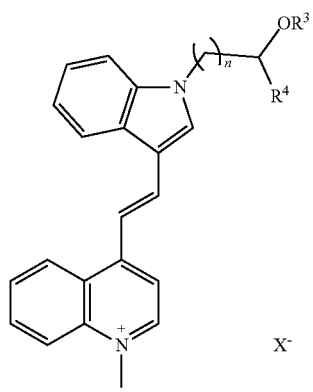

II wherein R³ is selected from a protective group and a phosphoramidite functionality; R⁴ is selected from H and —CH₂Phosphoramidite; n=1 or 2; X⁻ is a suitable counterion; when R⁴ is H, R³ is the phosphoramidite functionality; and when R⁴ is —CH₂Phosphoramidite, R³ is the protective group.

In one embodiment, the protective group is an acid-labile protective group. For example, in one embodiment the acid-labile protective group is selected from dimethoxytrityl (DMT), and 5'-O-2,7-dimethylpixyl (DMPx)

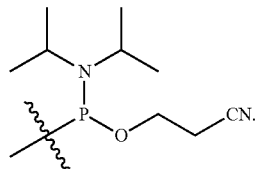 [SMILES: *P(OCCC#N)N(C(C)C)C(C)C]

The use of DMPx as a protecting group for the synthesis of DNA has been described in Sproviero et al., 2014.

In one embodiment, the phosphoramidite functionality is

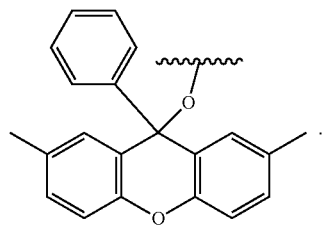

In one embodiment, the —CH₂Phosphoramidite is

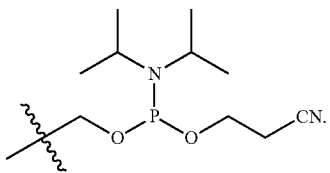 [SMILES: *COP(OCCC#N)N(C(C)C)C(C)C]

In one embodiment, the fluorescent phosphoramidite is selected from

II-1

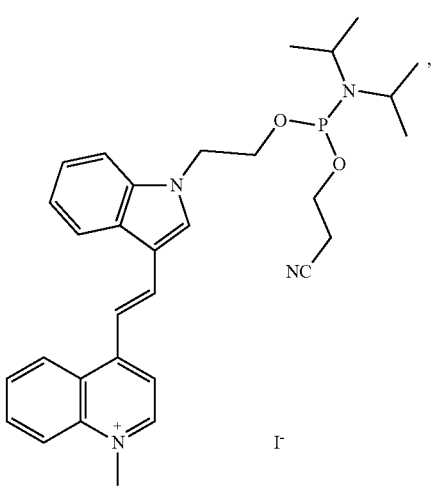

II-2

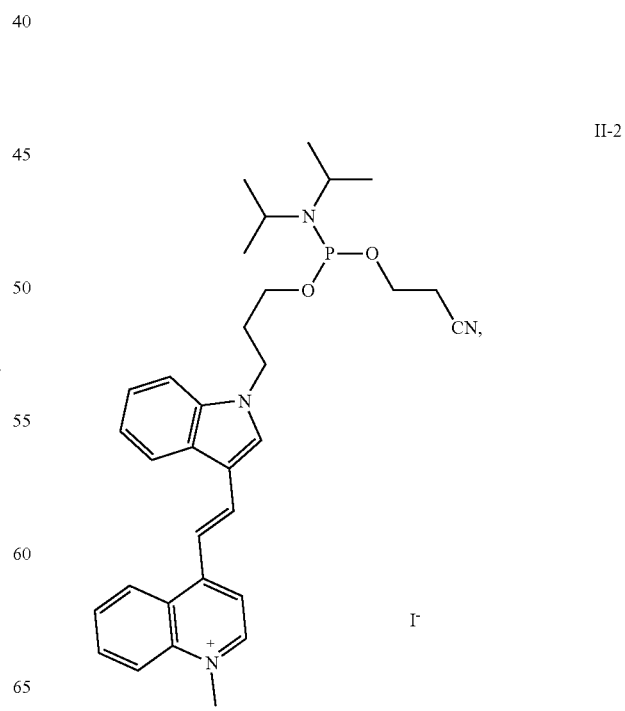

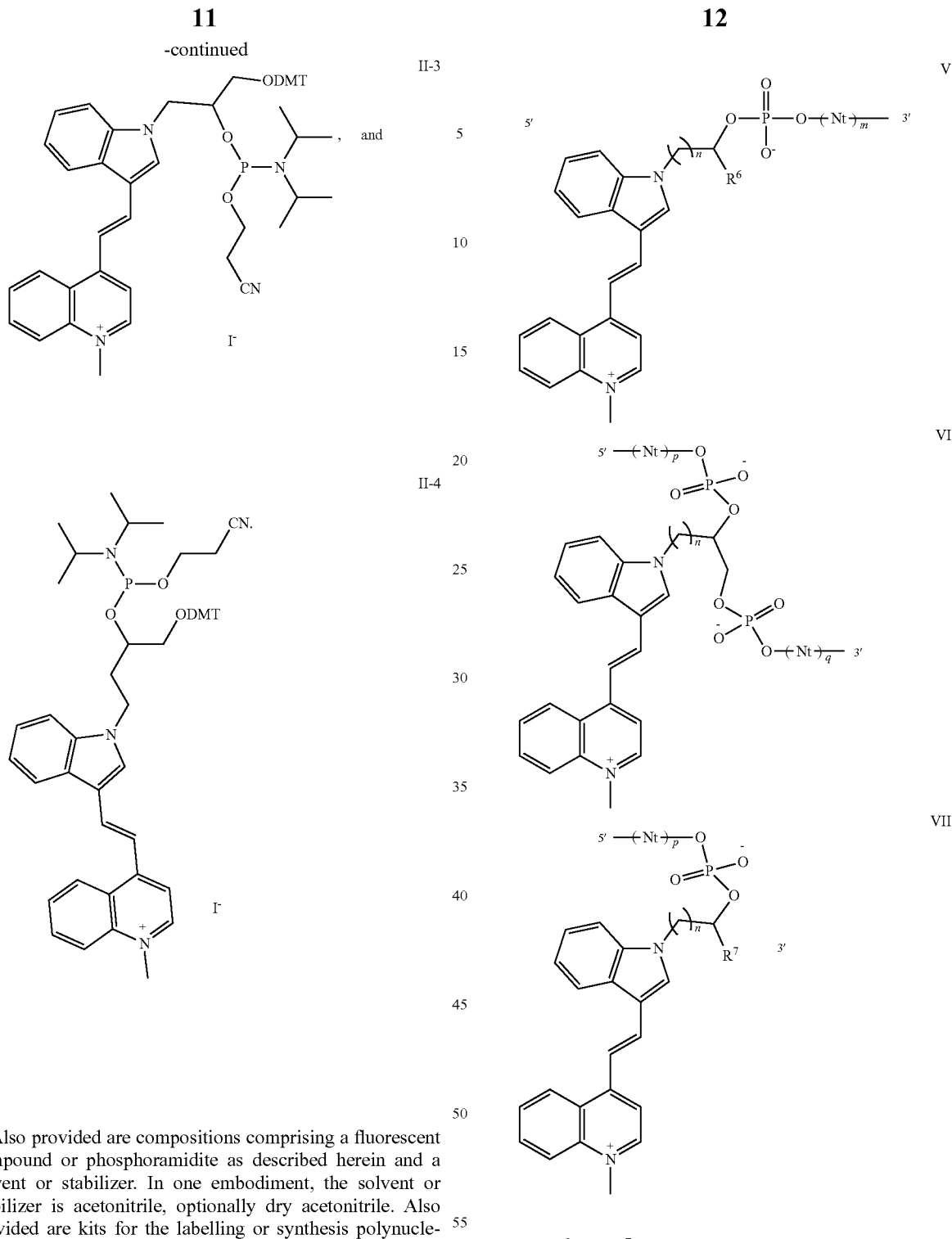

Also provided are compositions comprising a fluorescent compound or phosphoramidite as described herein and a solvent or stabilizer. In one embodiment, the solvent or stabilizer is acetonitrile, optionally dry acetonitrile. Also provided are kits for the labelling or synthesis polynucleotides with a fluorescent merocyanine dye. In one embodiment, the kit comprises one or more fluorescent phosphoramidites as described herein.

In one aspect, the fluorescent merocyanine dyes described herein may be conjugated to substrate such as a binding agent, polynucleotide or other biomolecule. Optionally, the fluorescent merocyanine dye may be directly conjugated to a substrate or through a linker.

In one embodiment there is provided a fluorescently labelled nucleotide or polynucleotide of structure selected from Formulae V, VI, and VII wherein $R^6$ and $R^7$ are independently selected from H and $CH_2OH$; n=1 or 2; m, p and q are independently an integer between 1 and 1000; and Nt is a nucleotide.

In one embodiment, m, p and q are independently an integer between 1 and 100, between 2 and 100 or optionally an integer between 10 and 60 or between 5 and 40.

In one embodiment, the polynucleotide comprises or consists of a nucleic acid molecule aptamer that binds to a target. In one embodiment, the aptamer comprises DNA and/or RNA. In one embodiment, the aptamer is a DNA aptamer.

The binding agents or aptamers described herein may selectively bind to a target, optionally to a target molecule. In one embodiment, the target comprises or consists or a biomolecule such as a protein, polypeptide, nucleic acid, lipid, polysaccharide, toxin, allergen or organic molecule. In one embodiment, the target is a cell surface protein. In one embodiment, the target is a virus, bacteria or cell.

In one embodiment, the fluorescently labelled polynucleotide of formula V, VI or VII comprises an aptamer that binds to thrombin. In one embodiment, the aptamer comprises 5'-GGTTGGTGTGGTTGG-3' (SEQ ID NO: 1). In one embodiment, the fluorescent label is attached to the thymine nucleotide at position 3 of SEQ ID NO: 1.

In another embodiment, the fluorescently labelled polynucleotide of formula V, VI or VII comprises an aptamer that binds to ochratoxin-A (OTA). In one embodiment, the aptamer comprises 5'-GATCGGGTGTGGGTGGCGTAAAGGGAGCATC-3' (SEQ ID NO: 2). In one embodiment, the fluorescent label is attached to the thymine nucleotide at position 19 of SEQ ID NO: 2.

Various methods known in the art of producing aptamers that bind to different targets may be used in combination with the embodiments described herein. For example, aptamer sequences may be determined using an in-vitro selection process known as Systematic Evolution of Ligands by Exponential Enrichment (SELEX) (se e.g. for example Blind and Blank, 2015). Essentially, SELEX proceeds through multiple rounds of selection wherein the target molecule is incubated with a large library of random DNA and/or RNA strands, after which binding aptamers are isolated and amplified until a highly specific and selective aptamer is isolated (see for example Jayasena, 1999).

In one embodiment, there is provided a compound of Formula III

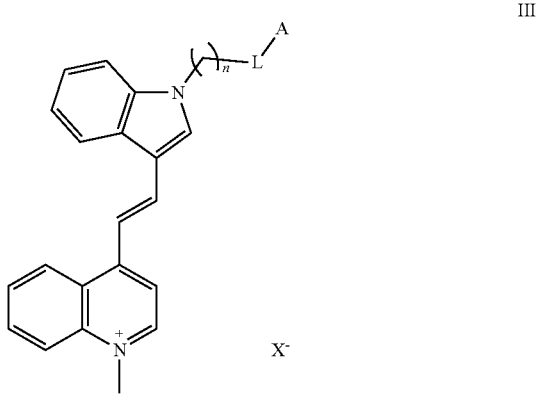

III wherein L is an optional linker; A is a substrate; $X^-$ is an optional suitable counterion; and n is an integer between 1 to 4.

In one embodiment, the substrate comprises or consists of a binding agent. For example, in one embodiment the binding agent is an aptamer, ligand or antibody that selectively binds a target molecule.

In one embodiment, the substrate comprises a biomolecule such as a polypeptide, polynucleotide, polysaccharide, lipid, carbohydrate, or organic molecule. In one embodiment, the substrate is a therapeutic agent such as a drug.

Optionally, in some embodiments the substrate comprises a magnetic bead. In one embodiment, a fluorescently labelled polynucleotide as described herein is conjugated to a magnetic beads. Magnetic beads are versatile tools for the purification, detection, and quantitative analysis of analytes from complex matrices (i.e. blood, urine, food components, cellular matrices). For example, in one embodiment a modified aptamer is synthesized with a 5'-end amine-modified group that is attached to carboxylated magnetic bead via peptide coupling reagents (i.e. EDC/NHS coupling). MBs modified with specific ligands such as aptamers allow isolation of the target molecule using strong magnets. This sample treatment increases the concentration of the target and avoids sample pre-treatment procedures like centrifugation, filtration and solid-phase extraction. (see for example, Modh et al. Sensors, 2018, 18, 1041)

Also provided are methods that use the fluorescent merocyanine compounds described herein for the detection of a target. Optionally, the compounds described herein may be conjugated to a binding agent or used in label-free assays for the detection of a target. As set out in Example 4, fluorescent merocyanine compounds such as 4QI have been demonstrated to be useful in label-free assays using aptasensors that exhibit GQ polymorphism.

Accordingly, in one embodiment there is provided a method for detecting a target in a sample, the method comprising:

contacting the sample with the fluorescent compound of Formula I and a binding agent for the target, wherein binding of the binding agent to the target changes the optical properties of the fluorescent compound in the sample; and detecting a change in the optical properties of the fluorescent compound in the sample.

In one embodiment, the binding agent and the fluorescent compound are combined prior to contacting the sample. In one embodiment, the binding agent is an aptamer, optionally a DNA aptamer.

In another embodiment, there is provided a method for detecting a target in a sample, the method comprising:

contacting the sample with a fluorescently labelled polynucleotide of any one of Formulae V, VI or VII; and detecting the fluorescently labelled polynucleotide bound to the target in the sample.

Also provided is a method for detecting a target in a sample, the method comprising:

contacting the sample with a compound of Formula III, wherein the substrate comprises a binding agent for the target; and detecting the compound bound to the target in the sample.

Various methods known in the art may be used to detect the fluorescently labelled polynucleotide or compound bound to the target in the sample. For example, in one embodiment, detecting the fluorescently labelled polynucleotide or compound bound to the target in the sample comprises detecting a change in one or more optical properties.

For example, a change in one or more optical properties may be detected by detecting a change in fluorescence, absorbance, fluorescence polarization and/or circular dichromism.

For example, in one embodiment, detecting a change in the optical properties of the fluorescently labelled polynucleotide bound to the target in the sample comprises detecting a level of the one or more optical properties of the fluorescently labelled polynucleotide and comparing the level of the one or more optical properties to one or more control levels. Optionally, the one or more control levels may include a predetermined control level or an experimentally determined control level.

In one embodiment, at least one of the control levels is representative of the optical properties of the fluorescently labelled polynucleotide in the sample in the absence of the target.

The methods described herein may also be used to determine a concentration or level of a target in a sample. In one embodiment, at least one of the control levels is representative of the optical properties of the fluorescently labelled polynucleotide or compound in the sample in the presence of a known concentration of the target. In one embodiment, the method further comprises determining a level of the target in the sample based on a difference or similarity between the one or more optical properties of the fluorescently labelled polynucleotide or compound in the sample and the one or more control levels.

In one embodiment, detecting a change in the optical properties of the fluorescently labelled polynucleotide or compound in the sample comprises detecting a change in absorbance, fluorescence or fluorescence polarization. In one embodiment, the change in absorbance is a change in circular dichroism.

In one embodiment, detecting the fluorescently labelled polynucleotide or compound bound to the target in the sample comprises detecting fluorescence emission intensity at one or more wavelengths. In one embodiment, the methods described herein comprise detecting fluorescence emission or absorbance at a plurality of wavelengths to obtain a fluorescence emission spectrum or an absorption spectrum.

In one embodiment, there is provided a method of detecting a target in a sample, the method comprising:
contacting the sample with a fluorescently labelled polynucleotide of any one of Formulas V, VI or VII, wherein the fluorescently labelled polynucleotide comprises an aptamer that binds to the target;
determining a fluorescence or an absorbance of the fluorescently labelled polynucleotide in contact with the sample; and
comparing the fluorescence or the absorbance of the fluorescently labelled polynucleotide in contact with the sample with a control.

In one embodiment, the control is representative of a sample that does not contain the target and a difference between the fluorescence or the absorbance of the fluorescently labelled polynucleotide in contact with the sample and the control is indicative of the presence of the target in the sample.

In one embodiment, the method comprises determining a fluorescence emission spectrum or an absorbance spectrum at a plurality of wavelengths and comparing the fluorescence emission spectrum or the absorption spectrum to one or more control fluorescence emission spectra or control absorption spectra.

In one embodiment, the method comprises determining a level of the target in the sample based on a change of intensity of the fluorescence or the absorbance of the fluorescently labelled polynucleotide in contact with the sample compared to the control.

In one embodiment, the method comprises determining a Stoke's shift for the fluorescently labelled polynucleotide or compound in contact with the sample and comparing the Stoke's shift for the fluorescently labelled polynucleotide in contact with the sample with a control.

In one embodiment, at least one of the excitation wavelengths is between about 200 nm and 2000 nm. In one embodiment, at least one of the excitation wavelengths between about 300 nm and 600 nm. In one embodiment, at least one of the excitation wavelengths is between about 450 nm and 550 nm, between about 490 and 510 nm, or about 500 nm.

In another embodiment, the fluorescent emission spectra or absorption spectra are generated by measuring the intensity of fluorescence or absorption at a plurality of wavelengths. In one embodiment, the spectra are generated by taking measurements from about 200 nm to about 2000 nm, from about 200 nm to 1000 nm, from about 200 nm to 630 nm, or from about 300 to 700 nm. In one embodiment, the spectra are generated by taking measurements from about 450 nm to 800 nm, from about 550 nm to 650 nm, from about 580 nm to 600 nm, or about 590 nm.

The products and methods described herein may be used to detect a target in vitro, ex vivo or in vivo. In one embodiment, the methods described here are for the detection of a target in a biological sample, such as a tissue sample, feces sample, urine sample or blood sample.

In another embodiment, the methods described here are for the detection of a target in an environmental sample such as a water sample or soil sample.

In another embodiment, the methods described herein are for the detection of a target in a food or beverage sample.

EXAMPLES

The following examples illustrate embodiments of the invention and do not limit the scope of the invention.

Materials and Methods

Materials

Commercial compounds were purchased from Sigma Aldrich (St. Louis, Mo.). Native TBA (5'-GGTTGGTGTGGTTGG), TBA-16 (5'-GGTTGGTGTGGTTGGT), its truncated complementary strand (5'-ACACCAACC) and native OTAA (5'-GATCGGGTGTGGGTGGCG TAAAGGGAGCATC) were purchased from Sigma Aldrich (Oakville, ON). Commercial aptamers less than and greater than 15 bases in length were cartridge purified and PAGE purified, respectively, by Sigma Aldrich (Oakville, ON). Bovine thrombin was purchased as a dry powder from Sigma Aldrich (St. Louis, Mo.) and stored at −10° C. Ochratoxin-A was obtained as a dry powder with 99.5% purity from by a collaborator at the University of Munster, Germany and stored at −10° C. Milli-Q (MQ) water purified water (18.2 MΩ·cm at 25° C.) was used in all buffers and spectroscopic studies.

Methods

NMR and HRMS Analysis $^1$H, $^{13}$C and $^{31}$P NMR spectra were recorded on Bruker™ Advance 300, 400 or 600 MHz spectrometers in either CDCl$_3$ (internal standard, for H$^1$ residual CHCl$_3$ $\delta_H$ 7.24; for $^{13}$C $\delta_C$ 77.0) or DMSO-d6 (internal standard, for H$^1$ residual DMSO $\delta_H$ 2.50; for $^{13}$C δC 40.0). All chemical shifts are reported in part per million (ppm) and coupling constants (J) were calculated based on first-order spectral analysis and reported in Hertz (Hz). $^1$H NMR data are reported using standard abbreviations: singlet (s) doublet (d), triplet (t), doublet of doublet (dd), triplet of doublet (td) and multiplet (m). HRMS (high-resolution mass spectrometry) spectra were obtained using electrospray ionization (ESI) on a high-resolution mass spectrometer equipped with an Orbitrap™ analyzer.

Oligonucleotide Synthesis and Purification

Oligonucleotide synthesis was performed to synthesize mTBA (4QI-TBA-E, 4QI-TBA-I) and mOTAA (4QI-OTAA-E, 4QI-OTAA-13, 4QI-OTAA-19). Oligonucleotide synthesis was carried out on 1 μM scale on a MerMaid 12 solid-phase oligonucleotide synthesizer using a modified version of an established protocol. (Fadock et al., 2016) Modifications included increasing the coupling time for the 4QI phosphoramidites from 2 min to 2 h, doubling the number of post-coupling acetonitrile washes for the 4QI phosphoramidites and leaving the final DMT on. Oligonucleotide synthesis reagents included: modified phosphoramidite (via standard 3-cyanoethylphosphoramidite chemistry), unmodified phosphoramidites (Pac-dA-CE, Ac-dC-CE, iPr-Pac-dG-CE, and dT-CE), activator (0.25 M 5-(ethylthio)-1H-tetrazole in $CH_3CN$), oxidizing agent (0.02 M $I_2$ in THF/pyridine/$H_2O$, 70/20/10, v/v/v), deblock (3% DCA in dry DCM), cap A (THF/2,6-lutidine/acetic anhydride), cap B (methylimidazole in THF), and solid supports (5'-DMT-dT or 5'-DMT-dC(ac) 1000 Å CPG). Following DNA synthesis, oligonucleotides were cleaved from the solid support and deprotected using a modified version of the UltraMild deprotection protocol.[17] The crude oligonucleotides were dissolved in 2 mL of 0.05 M $K_2CO_3$ in MeOH, heated to 37° C. for 3 h, cooled to RT overnight, and then centrifuged (10,000 rpm for 10 min). The supernatant was removed and retained, and the solid support beads were resuspended in 500 mM aqueous triethylamine. Both solutions were passed through a 22-micron filter to remove the solid support beads from the DNA solution.

The crude oligonucleotide solutions were purified using an HPLC equipped with an autosampler, an autocollector and a diode array detector (monitored at 254 nm and $\lambda_{abs}$ of 4QI). Separation was carried out at 45° C. using a 5 μm reversed-phase semipreparative C18 column (100×10 mm) with a flow rate of 3.3 mL/min. Various gradients of buffer B (30:70 aqueous 50 mM TEAA, pH 7.2/acetonitrile) in buffer D (95:5 aqueous 50 mM TEAA, pH 7.2/acetonitrile) were used to separate the oligonucleotides. Buffer gradient varied depending on oligonucleotide length as per Table 1.

TABLE 1

Buffer gradients for oligonucleotide purification based on length.

| Aptamer Length | Buffer Gradients |
|---|---|
| <20 bases | Buffer B at 100% for 5 min, then Buffer D increased to 15% for 10 min. Buffer D increased to 60% for 2 min, to 80% for 2 min, and then to 90% for 1 min. Buffer B increased to 100% for the last 2 min. |
| >40 bases | Buffer B at 100% for 5 min, then Buffer D increased to 5% for 3 min. Buffer D increased to 15% for 7 min, to 80% for 2 min, ad then to 90% for 1 min. Buffer B increased to 100% for last 1 min. |

Following purification, the collected samples were lyophilized until dry using a Labconco FreeZone 4.5 lyophilizer and then dissolved in MQ water and stored at −10° C.

Quantification of Oligonucleotides and Targets

All aptamer and target solutions were quantified using a UV-Vis spectrophotometer equipped with a 6×6 Multicell Block Peltier, stirrer and temperature controller. The extinction coefficients for all targets were drawn from supplier product information files: Bovine Thrombin $\epsilon=72,510$ $M^{-1}$ $cm^{-1}$ at 280 nm in water, and Ochratoxin-A $\epsilon=6,400$ $M^{-1}$ $cm^{-1}$ at 333 nm in methanol. The extinction coefficients for all native aptamers were estimated using IDT DNA online software. Extinction coefficients of the modified aptamers were estimated to be equal to that of the unmodified aptamers, aside from the internally modified aptamers for which the extinction coefficients were calculated minus the native nucleotide at the site of incorporation. Aliquots of stock solutions were added to 1000 μL MQ water in quartz cells (Hellma 114-QS), with a path length of 10 mm. No less than 5 aliquots were added and used to determine oligonucleotide/target concentration using the Beer Lambert law:

$$A = \epsilon l c$$

where A is sample absorbance after blank correction, t is the calculated extinction coefficient, l is the path length and c is the molar concentration of the sample in the cuvette. The average of the concentrations resulting from each aliquot was determined as the stock concentration.

Preparation of Buffer Stock Solutions

The standard potassium buffer ($K^+$ buffer) used in all TBA studies was prepared by dissolving $KH_2PO_4$ (5.0 M) and KCl (1.0 M) in MQ $H_2O$. The pH of the solution was then adjusted by adding dilute HCl or KOH until a pH of 7.00±0.05 was reached. The OTA binding buffer (OTABB) used in all OTA studies was prepared by dissolving $CaCl_2$) (2.0 M), NaCl (1.2 M), triphosphate (1.0 M) and KCl (0.5 M) in MQ $H_2O$. The pH of this solution was adjusted with dilute HCl or NaOH until a pH of 8.00 t 0.05 was reached. In all cases where buffer was added, the stock buffer was used as 10% of the final sample solution volume thus diluting the sample buffer concentrations stated here 10-fold.

Melting Temperature Studies

Thermal melting temperatures ($T_m$) were determined using quartz cells (Hellma 114-QS) with a light path of 10 mm. DNA UV absorbance was monitored at either 260 nm (duplex) or 295 nm (GQ) using a Cary 300-Bio UV-Vis spectrophotometer, fitted with a 6×6 multicell Peltier block heater. For all TBA and OTAA $T_m$ analyses, sample solutions of 6 μM oligonucleotide were prepared in 10% $K^+$ buffer or OTABB, respectively, and diluted with MQ water. Solutions containing free 4QI were prepared using TBA or OTAA and 4QI each at 6 μM. Duplex solutions were prepared to 6 μM oligonucleotide with 1.1 equivalents of complementary DNA. After mixing by inversion, UV absorbance was monitored for each sample over the course of five alternating ramps from 10° C. to 90° C. and 90° C. to 10° C. at a heating rate of 0.5° C. min-1. $T_m$ values were calculated using the hyperchromicity function included within the spectrophotometer software.

Circular Dichroism Studies

CD spectra were recorded using a Jasco J-815 CD spectrometer equipped with a thermal controlled 1×6 multicell block. 200 μL aliquots of samples resulting from thermal melting studies were deposited into quartz cells (110-Qs) with a light path of 1 mm. CD spectra for these samples were recorded at 10° C. with a scanning speed of 100 nm/min and a bandwidth of 1 mm. CD spectra were monitored between 200 and 600 nm. Five scans per sample were collected, smoothed and corrected against a blank measurement in the appropriate buffer using the spectrometer software.

Photophysical Measurements

All fluorescence excitation and emission measurements were made at 25.00° C. using a PTI Alphascan-2 spectrofluorometer equipped with a 1×4 Multicell Block Peltier and temperature controller, with baseline correction and variable slit widths as specified. All fluorescence excitation spectra were recorded at the maximum emission wavelength of the fluorophore and emission spectra were recorded at the maximum excitation wavelength.

Viscosity studies were completed using quartz cells (Hellma 101-QS) with a light path of 10 mm. A 100 μM stock solution of 4QI was prepared in MQ water. Using this stock solution, 3 µM solutions of 4QI were prepared using glycerol and MQ H$_2$O in varying proportions. Five separate solutions were prepared with the following glycerol:water ratios −0:100, 20:80, 40:60, 60:40, and 80:20. Following mixing by inversion (×20), emission and excitation spectra for each sample were recorded as described using slit widths of 5 nm.

Solvatochromatic studies were completed using quartz cells (Hellma 101-QS) with a light path of 10 mm. A 100 µM stock solution of 4QI was prepared in reagent grade DMSO. Using the stock solution, 3 µM solutions of 4QI were prepared in a series of solvents: MQ water, methanol, acetonitrile, THF, chloroform and isopropyl alcohol. After mixing by inversion (×20), emission and excitation spectra for each sample were recorded as described using slit widths of 5 nm.

Regarding the comparative oligonucleotide fluorescence studies, fluorescence emission was used to calculate $I_{rel}$ values as per the following formulas:

$$I_{rel}=(E_{ss}/E_{GQ}) \text{ or } I_{rel}=(E_{dup}/E_{GQ})$$

where the emission maxima of 4QI in single-stranded, double-stranded and GQ DNA correspond to $E_{ss}$, $E_{dup}$ and $E_{GQ}$, respectively.

Fluorescence Titration Binding Studies

Fluorescence binding studies were completed using quartz cells (Hellma 521-QS) with a light path of 3×3 mm. Solutions of 4QI-TBA-E and 4QI-TBA-I were prepared to 6 µM from stock solutions in 10% K$^+$ buffer diluted with MQ water. Solutions of 4QI-OTAA-E, 4QI-OTAA-13 and 4QI-OTAA-19 were prepared to 6 µM from stock solutions in 10% OTABB diluted with MQ water. Solutions of 4QI-TBA-Free and 4QI-OTAA-Free were prepared using 6 µM TBA or OTAA and 6 µM 4QI with 10% volume of the appropriate buffer diluted with MQ water. For the reverse OTA titrations, OTA solutions were prepared to 1 or 6 µM from 50 or 500 µM stock solutions in 10% OTABB diluted with MQ water.

After recording the emission and excitation spectra of each sample, 2 equivalents of target (thrombin, OTA or mOTAA for the reverse titrations) were added to the sample 0.2 equivalents at a time. After each addition, the sample was mixed by inversion (×20), and the emission and excitation spectra for each sample were again recorded. Fluorescence emission was used to calculate % displacement using the following equation:

$$\% \text{ displacement}=(E_{initial}-E_{plateau})/E_{initial}\times100$$

where $E_{initial}$ is the initial fluorescence emission maxima and $E_{plateau}$ is the fluorescence emission maxima after a plateau is observed or after the final addition when no plateau was observed. Either excitation or emission fluorescence intensity values were converted to percent bound and plotted against target concentration (M) in SigmaPlot 11.0 software using single-site saturation and/or linear models to afford $K_d$ values, $R^2$ values and binding curves.

Fluorescence Polarization

Fluorescence polarization studies were recorded on a PTI Alphascan-2 spectrofluorometer (Photon Technology International, London, ON) with a cell holder equipped with thermostat temperature control set to 20.00° C. Samples were analyzed in quartz cells (108.002F-QS) with light path of 10×2 mm, with excitation and emission slit widths set to 6 nm. Samples were excited at 505 nm, and emission at 580 nm was monitored with an integration time of 30 seconds. In all cases, 2 equivalents of target were added (0.2 eq at a time) into 6 µM oligonucleotide samples. Following each target addition, the sample was mixed by inversion (×20) and allowed to rest for 5 min before each scan. Fluorescence anisotropy measurements were made by simultaneously comparing the intensities of the vertically and horizontally polarized emitted light when the sample was excited with vertically polarized light. Each anisotropy value was calculated as the mean of two determinations. Fluorescence anisotropy values were converted to percent bound and plotted against target concentration (M) in SigmaPlot 11.0 software using single-site saturation and/or linear models to afford $K_d$ values, $R^2$ values and binding curves.

Example 1: Chemical Synthesis

Synthesis of 1,4-dimethylquinolin-1-ium iodide

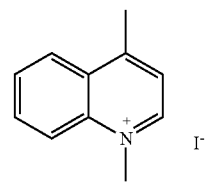

This compound was synthesized by the reported method as a bright yellow solid. (Coe et al, 2009) $^1$H-NMR (CDCl$_3$, 400 MHz): $\delta_H$ 2.99 (s, 3H), 4.57 (s, 3H), 8.05 (t, J=7 Hz, 2H), 8.26 (m, J=3 Hz, 1H), 8.50 (m, J=4.59 Hz, 1H), 9.35 (d, J=6 Hz, 1H).

Synthesis of 1-(3-hydroxypropyl)-1H-indole-3-carboxyaldehyde

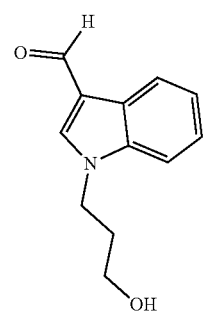 [SMILES: O=Cc1cn(CCCO)c2ccccc12]

This compound was synthesized by the reported method as a yellow/orange solid. 62 $^1$H-NMR (DMSO, 400 MHz): $\delta_H$ 1.94 (m, 2H), 3.39 (m, 2H), 4.33 (t, J=7 Hz, 2H), 4.69 (t, J=5 Hz, 1H), 7.27 (m, 2H), 7.60 (d, J=8 Hz, 1H), 8.11 (d, J=8 Hz, 1H), 8.28 (s, 1H), 9.90 (s, 1H).

Synthesis of 1-(2,3-dihydroxypropyl)-1H-indole-3-carboxyaldehyde

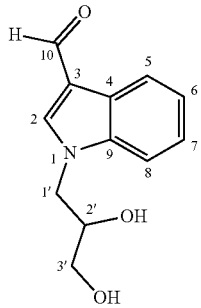 [SMILES: O=Cc1cn(CC(O)CO)c2ccccc12]

1H-indole-3-carboxyaldehyde (3.4 mmol) was dissolved in 5 mL DMF, and K2CO3 (17.2 mmol), KI (5.2 mmol) and 3-chloropropane-1,2-diol (4.5 mmol) were added to the mixture, which was then stirred at 80° C. for 12 hours. The mixture was then cooled to rt, filtered over silica and washed with MeOH (5×10 mL). The solvent was removed under reduced pressure, and the crude product was redissolved in 98:2 DCM:MeOH and loaded onto a silica column preconditioned with 98:2 DCM:MeOH. Unreacted 1H-indole-3-carboxyaldehyde eluted at 98:2 DCM:MeOH and the product eluted at 96:4 DCM:MeOH. After combining the pure fractions, the solvent was removed under reduced pressure to yield 345 mg of orange powder (46% yield). $^1$H-NMR (DMSO, 600 MHz): $\delta_H$ 3.38 (m, 1H, H-3'), 3.47 (m, 1H, H-3'), 3.87 (bs, 1H, H-2'), 4.16 (dd, J=8, 14 Hz, 1H, H-1'), 4.44 (dd, J=3, 14 Hz, 1H, H-1'), 4.92 (t, J=6 Hz, 1H, OH-3'), 5.15 (d, J=6 Hz, 1H, OH-2'), 7.26 (t, J=7 Hz, 1H, H-6), 7.31 (t, J=7 Hz, 1H, H-7), 7.62 (d, J=8 Hz, 1H, H-8), 8.14 (d, J=8 Hz, 1H, H-5), 8.24 (s, 1H, H-2), 9.93 (s, 1H, H-10). $^{13}$C-NMR (DMSO, 150 MHz): $\delta_C$ 50.23 (C-1'), 63.80 (C-3'), 70.66 (C-2'), 111.74 (C-8), 117.45 (C-4), 121.44 (C-5), 122.82 (C-6), 123.83 (C-7), 125.11 (C-3), 138.02 (C-9), 142.35 (C-2), 185.10 (C-10). HRMS calculated for $C_{12}H_{13}NO_3$=[M+H]+220.0974; found=220.0951.

Synthesis of 1-(3-ODMT-2-hydroxypropyl)-1H-indole-3-carbaldehyde

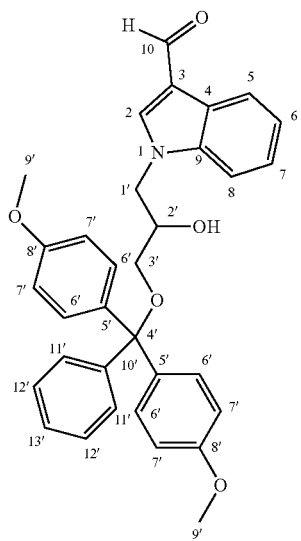 [SMILES: COc1ccc(C(OCC(O)Cn2cc(C=O)c3ccccc32)(c2ccccc2)c2ccc(OC)cc2)cc1]

This compound (1.8 mmol) was heated to 40° C. under reduced pressure for 2 h. The flask was then cooled to rt, fitted with a constant pressure dropping funnel and reverse filled with argon. The compound was then dissolved in 5 mL dry THF and TEA (18.3 mmol) was added to the mixture. A solution of DMT-CI (2.4 mmol) and THF (5 mL) was then added to the dropping funnel and added dropwise to the mixture over 30 min. The mixture was stirred at rt under argon and monitored by TLC. Upon reaction completion, the THF was removed under reduced pressure. The crude product was redissolved in 95:5 DCM:TEA and loaded onto a silica column which was preconditioned with 95:5 DCM:TEA. Running the column at 95:5 DCM:TEA, the unreacted DMT material eluted first, followed immediately by the product. The pure product fractions were combined, and the solvents were removed under reduced pressure to yield 716 mg of pale, yellow solid (75% yield). $^1$H-NMR (DMSO, 600 MHz): $\delta_H$ 2.91 (dd, J=6, 9 Hz, 1H, H-3'), 3.06 (dd, J=5, 9 Hz, 1H, H-3'), 3.74 (s, 2×3H, H-9'), 4.06 (bs, 1H, H-2'), 4.27 (dd, J=7, 14 Hz, 1H, H-1'), 4.46 (dd, J=4, 15 Hz, 1H, H-1'), 5.38 (d, J=4 Hz, 1H, OH-2'), 6.89 (dd, J=4, 9 Hz, 4×1H, H-7'), 7.24 (m, 3H, H-6, H-7, H-13'), 7.31 (m, 4×1H, 2×1H, H-6', H-12'), 7.46 (d, J=8 Hz, 2H, H-11'), 7.56 (d, J=8 Hz, 1H, H-8), 8.10 (m, 2×1H, H-5, H-2), 9.87 (s, 1H, H-10). $^{13}$C-NMR (DMSO, 150 MHz): $\delta_C$ 50.19 (C-1'), 55.48 (C-9'), 65.49 (C-3'), 68.80 (C-2'), 86.02 (C-4'), 111.78 (C-8), 113.64 (C-7'), 117.43 (C-3), 121.36 (C-5), 122.74 (C-6), 123.77 (C-7), 125.02 (C-4), 127.12 (C-13'), 128.19 (C-11'), 128.31, 130.23 (C-6', C-12'), 136.08 (C-5'), 137.97 (C-9), 142.08 (C-2), 145.43 (C-10'), 158.56 (C-8'), 184.99 (C-10). HRMS calculated for $C_{33}H_{32}NO_5$=[M+H]+ 522.2280; found=522.2269.

Synthesis of 4-(2-(1-(3-hydroxypropyl)-1H-indol-3-yl)vinyl)-1-methylquinolin-1-ium iodide (I-2)

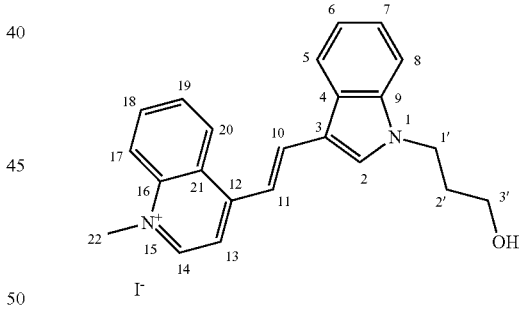

Compound 1-(2,3-dihydroxypropyl)-1H-indole-3-carboxyaldehyde (1.62 mmol), 1,4-dimethylquinolin-1-ium iodide (1.95 mmol) and 6 drops of piperidine were combined in a microwave vessel and dissolved in 3 mL ethanol. The mixture was exposed to microwave radiation using a CEM microwave reactor at a temperature of 80° C. with stirring under variable pressure for 10 min. After this time, 7 mL of acetonitrile was added, and the mixture was heated to reflux for 2 h. The mixture was then cooled to rt and the crude product was filtered and washed with diethyl ether (5×10 mL), affording 421 mg of red solid (62% yield). $^1$H-NMR (DMSO, 600 MHz): $\delta_H$ 1.97 (m, 1×2H, H-2'), 3.44 (q, J=5 Hz, 2H, H-3'), 4.30 (t, J=7 Hz, 2H, H-1'), 4.35 (s, 3H, H-22), 4.70 (t, J=5 Hz, 1H, OH-3'), 7.26 (td, J=1, 7 Hz, 1H, H-6), 7.30 (td, J=1, 7 Hz, 1H, H-7), 7.58 (d, J=8 Hz, 1H, H-8), 7.85 (d, J=16 Hz, 1H, H-11), 7.91 (t, J=8 Hz, 1H, H-19), 8.12 (td, J=1, 7 Hz, 1H, H-18), 8.15 (d, J=8 Hz, 1H, H-5), 8.20 (d, J=9 Hz, 1H, H-17), 8.32 (m, 2×1H, H-2, H-13), 8.42 (d, J=16 Hz, 1H, H-10), 8.83 (d, J=8 Hz, 1H, H-20), 9.00 (d, J=7 Hz, 1H, H-14). $^{13}$C-NMR (DMSO, 150 MHz): $\delta_C$ 32.97 (C-2'), 43.79 (C-1'), 44.34 (C-22), 58.07 (C-3'), 111.47 (C-8), 113.08 (C-11), 113.72 (C-13), 114.12 (C-3), 119.23 (C-17), 120.81 (C-5), 122.08 (C-6), 123.47 (C-7), 125.63 (C-21), 126.44 (C-4), 126.46 (C-20), 128.82 (C-19), 134.85 (C-18), 135.38 (C-2), 137.51 (C-9), 137.99 (C-10), 139.00 (C-16), 146.71 (C-14), 153.63 (C-12). HRMS calculated for $C_{23}H_{23}N_2O^+$ =[M]$^+$ 343.1805; found=343.1808.

Synthesis of 4-(2-(1-(3-ODMT-2-hydroxypropyl)-1H-indol-3-yl)vinyl)-1-methylquinolin-1-ium

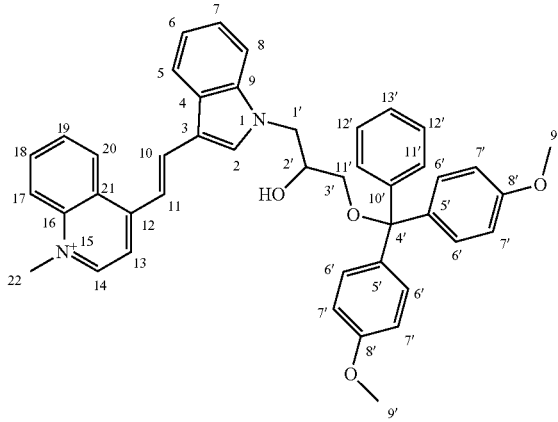 [SMILES: COc1ccc(C(OCC(O)Cn2cc(/C=C/c3cc[n+](C)c4ccccc34)c3ccccc32)(c2ccccc2)c2ccc(OC)cc2)cc1]

Compound 1-(3-ODMT-2-hydroxypropyl)-1H-indole-3-carbaldehyde (0.383 mmol), 1,4-dimethylquinolin-1-ium iodide (0.383 mmol) and 5 drops of piperidine were combined in a microwave vessel and dissolved in 4 mL ethanol. The mixture was exposed to microwave radiation using a CEM microwave reactor at a temperature of 80° C. with stirring under variable pressure for 10 min. After this time, the mixture was cooled to rt and diethyl ether (10 mL) was added to afford a purple solid which was filtered, washed with diethyl ether (5×5 mL) and collected. This crude product was redissolved in DCM and loaded onto a column packed with basic alumina which was preconditioned with DCM. Running the column at 98:2 DCM:MeOH, the product eluted first, followed by unreacted 1a. The pure product fractions were combined, and the solvents were removed under reduced pressure to yield 142 mg of iridescent, purple solid (56% yield). $^1$H-NMR (CDCl$_3$, 600 MHz): $\delta_{3.16}$ (dd, J=7, 9 Hz, 1H, H-3'), 3.34 (dd, J=4, 10 Hz, 1H, H-3'), 3.73 (s, 2×3H, H-9'), 4.19 (s, 3H, H-22), 4.27 (m, 2×1H, H-1', H-2'), 4.40 (m, 1H, H-1'), 4.56 (d, J=5 Hz, 1H, OH-2'), 6.79 (d, J=9 Hz, 4×1H, H-7'), 7.19 (m, 3×1H, H-13', H-7, H-8), 7.29 (m, 2×1H, H-12', 4×1H, H-6'), 7.37 (m, 1H, H-6), 7.45 (m, 1H, H-11, 2×1H, H-11'), 7.74 (t, J=8 Hz, 1H, H-19), 7.70 (m, 1H, H-5), 7.80 (d, J=9 Hz, 1H, H-17), 7.90 (m, 3×1H, H-10, H-13, H-18), 8.19 (s, 1H, H-2), 8.44 (d, J=9 Hz, 1H, H-20), 9.04 (d, J=7 Hz, 1H, H-14). $^{13}$C-NMR (CDCl$_3$, 150 MHz): $\delta_C$ 44.04 (C-22), 49.90 (C-1'), 55.14 (C-9'), 65.05 (C-3'), 68.89 (C-2'), 86.29 (C-4'), 111.03 (C-6), 111.94 (C-11), 113.07 (C-7'), 113.17 (C-13), 113.91 (C-3), 117.62 (C-17), 120.03 (C-5), 122.15 (C-8), 123.35 (C-7), 125.41 (C-21), 125.62 (C-4), 125.90 (C-20), 126.73 (C-13'), 127.78 (C-12'), 127.95 (C-11'), 128.46 (C-19), 129.92 (C-6'), 134.46 (C-18), 135.68, 135.74 (C-5'a, C-5'b), 137.32 (C-2), 137.92 (C-9), 138.23 (C-10), 138.42 (C-16), 144.62 (C-10'), 146.09 (C-14), 153.71 (C-12), 158.37 (C-8'). HRMS calculated for $C_{44}H_{41}N_2O_4^+$=[M]$^+$ 661.3061; found=661.3053.

Synthesis of 4-(2-(1-(3-hydroxypropyl)-1H-indol-3-yl)vinyl)-1-methylquinolin-1-ium iodide phosphoramidite (II-2)

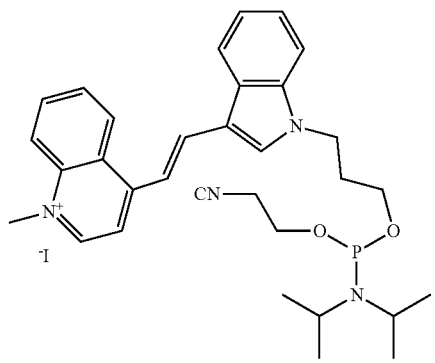

Compound 1-2 iodide (4-(2-(1-(3-hydroxypropyl)-1H-indol-3-yl)vinyl)-1-methylquinolin-1-ium iodide) (0.5 mmol) was co-evaporated with dry toluene (3×5 mL), and then dissolved in 7 mL dry acetonitrile under argon. Dry triethylamine (2.4 mmol) and 2-cyanoethyl N,N-diisopropylchlorophosphoramidite (0.7 mmol) were added and the mixture which was stirred at rt under argon and monitored via TLC until the reaction appeared to be complete (45 min). The crude product was dried under reduced pressure, redissolved in 3 mL dry DCM under argon and then added dropwise to a flask containing 20 mL dry hexanes under argon. The product precipitated as a solid and the hexane layer containing unreacted phosphitylating reagent and unreacted dye was removed. This purification process was repeated 3 times after which the solid product was again dried under reduced pressure and stored at −10° C. under argon, yielding 131 mg of product as a purple powder (62% yield). $^{31}$P NMR analysis was immediately performed. HRMS calculated for $C_{32}H_{40}N_4O_2P^+$=[M]$^+$ 543.2883; found=543.2877.

Synthesis of 4-(2-(1-(3-ODMT-2-hydroxypropyl)-1H-indol-3-yl)vinyl)-1-methylquinolin-1-ium phosphoramidite (II-3)

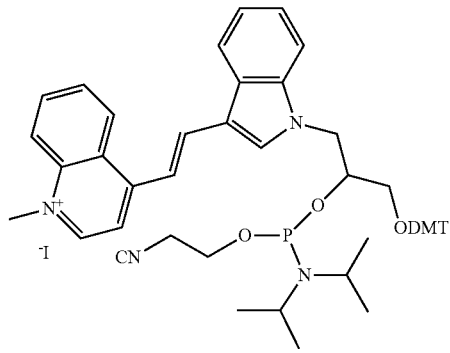

Compound 4-(2-(1-(3-ODMT-2-hydroxypropyl)-1H-indol-3-yl)vinyl)-1-methylquinolin-1-ium (0.3 mmol) was co-evaporated with dry toluene (3×5 mL), and then dissolved in 7 mL dry DCM under argon. Dry triethylamine (1.6 mmol) and 2-cyanoethyl N,N-diisopropyl-chlorophosphoramidite (0.5 mmol) were added and the mixture was stirred at rt under argon and monitored via TLC until completion (45 min). The crude product was dried under reduced pressure until a volume of 2 mL was achieved, and then added dropwise to a flask containing 20 mL dry hexanes under argon. The product precipitated as a solid and the hexane layer containing unreacted phosphitylating reagent and unreacted dye was removed. This purification process was repeated 3 times after which the solid product was again dried under reduced pressure and stored at −10° C. under argon, yielding 77 mg of product as a purple powder (28% yield). 31P NMR analysis was immediately performed. HRMS calculated for $C_{53}H_{58}N_4O_5P^+=[M]^+861.4139$; found=861.4133.

Example 2: Incorporation of 4QI within the Thrombin Binding Aptamer

The thrombin binding aptamer (TBA) has been widely used to model the responses of fluorescent ligands within DNA aptamers. In the presence of thrombin protein or stabilizing metal ions, this 15-mer aptamer folds into a GQ topology which has been well characterized using NMR and X-ray crystallography. (Wang et al., 1993; Wang et al., 1993; Kelly et al., 1996; Padmanabhan et al. 1993; Padmanabhan et al. 1993; Russo et al., 2012) These studies revealed that TBA forms an antiparallel, unimolecular GQ consisting of two G-tetrads connected via three edgewise loops. (Wang et al., 1993) A $T_7$-$G_8$-$T_9$ loop protrudes from the top face of the aptamer, and the structural integrity of this loop is known to be essential for aptamer stability. (Smimov et al., 2000) Two short T-T loops ($T_3$-$T_4$ and $T_1$-$T_{13}$) extend from the opposite face of the aptamer and interact directly with the protein target. (Russo et al., 2012) Isothermal titration calorimetry has been used to quantify the target binding affinity of TBA, yielding a $K_d$ of 0.33 μM. (Pagano et al. 2008) The wealth of information regarding TBA has favored its use as a "proof of concept" aptamer facilitating the development of many aptamer-based biosensors.

A massive array of fluorescent aptasensors have been developed for TBA, including those using label-free, end-label, and internal-label detection schemes. Here, experiments were performed to synthesize and characterize a fluorescent merocyanine dye. Experiments were also performed to develop fluorometric aptasensors for thrombin using label-free, end-label and internal-label designs using ≤3 assay components and a single merocyanine dye and to compare the utility of these DNA aptasensors in thrombin detection.

Synthesis and Characterization of Merocyanine Dyes

Synthesis of 4QI

Based on the sensitivity of merocyanine dyes to changes in their local environment, this class of dyes is well suited for incorporation into DNA aptasensors where target binding would cause such a change. (Want et al. 2011)

The probes synthesized herein is referred to as "4QI", named based on its 4-methylquinoline and indole heterocyclic components. Specifically, the quinoline nitrogen within 4QI is activated by $CH_3$, while a propanol or propanediol moiety resides on the indoline nitrogen.

Two structurally similar dyes containing the 4QI fluorophore were synthesized to afford phosphoramidites which could be covalently linked to oligonucleotides as end-labels or internal-labels. Dyes for use as end-labels must contain a single primary hydroxyl group, which is converted into a protected phosphate group during amidite synthesis that serves as an attachment point to 5'-OH termini during oligonucleotide synthesis. Dyes for use as internal-labels are more difficult to synthesize because they require two hydroxyl groups to serve as attachment points to the 5'-OH and 3'-$PO_4$ of a growing oligonucleotide. In this case, one of these hydroxyls is converted to the protected phosphate while the other is DMT protected.

The merocyanine dye 4QI-alcohol (1-2) was synthesized by condensing 1,4-dimethylquinolin-1-ium iodide (Coe et al., 2009) with indole-3-carboxyaldehyde adducted at the nitrogen with a propanol moiety (Naik et al., 2013) as per Scheme 1. 4QI-DMT (4-(2-(1-(3-ODMT-2-hydroxypropyl)-1H-indol-3-yl)vinyl)-1-methylquinolin-1-ium) was synthesised by condensing 1,4-dimethylquinolin-1-ium iodide with indole-3-carboxyaldehyde adducted at the nitrogen with a propanediol moiety (1-(2,3-dihydroxypropyl)-1H-indole-3-carboxyaldehyde) (Hirayama et al., 2012) protected with 4,4'-dimethoxytrityl chloride (1-(3-ODMT-2-hydroxypropyl)-1H-indole-3-carbaldehyde) as per Scheme 2. 4QI-alcohol (1-2) and 4QI-DMT (4-(2-(1-(3-ODMT-2-hydroxypropyl)-1H-indol-3-yl)vinyl)-1-methylquinolin-1-ium) were then converted to their corresponding abasic phosphoramidites II-2 and II-3 using standard phosphoramidite synthesis. All new compounds were characterized by HR-mass spectrometry and NMR for identification and to confirm purity.

Scheme 1: Overview of 4QI-alcohol phosphoramidite (compounds I-2 and II-2) synthesis.

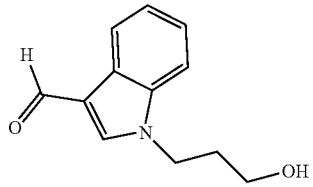

-continued
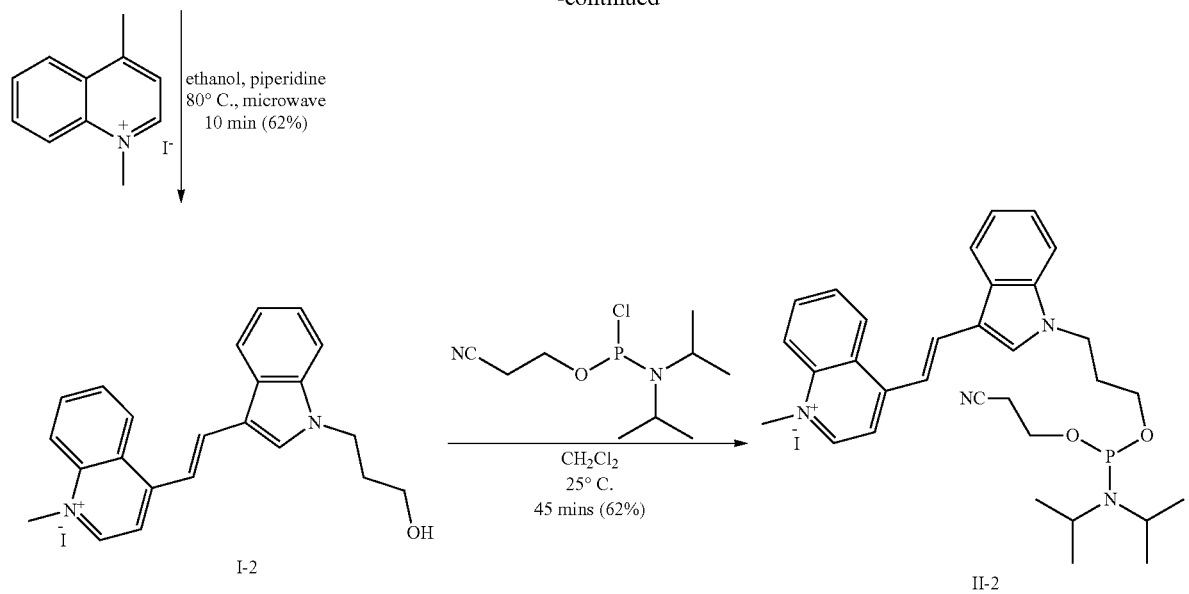
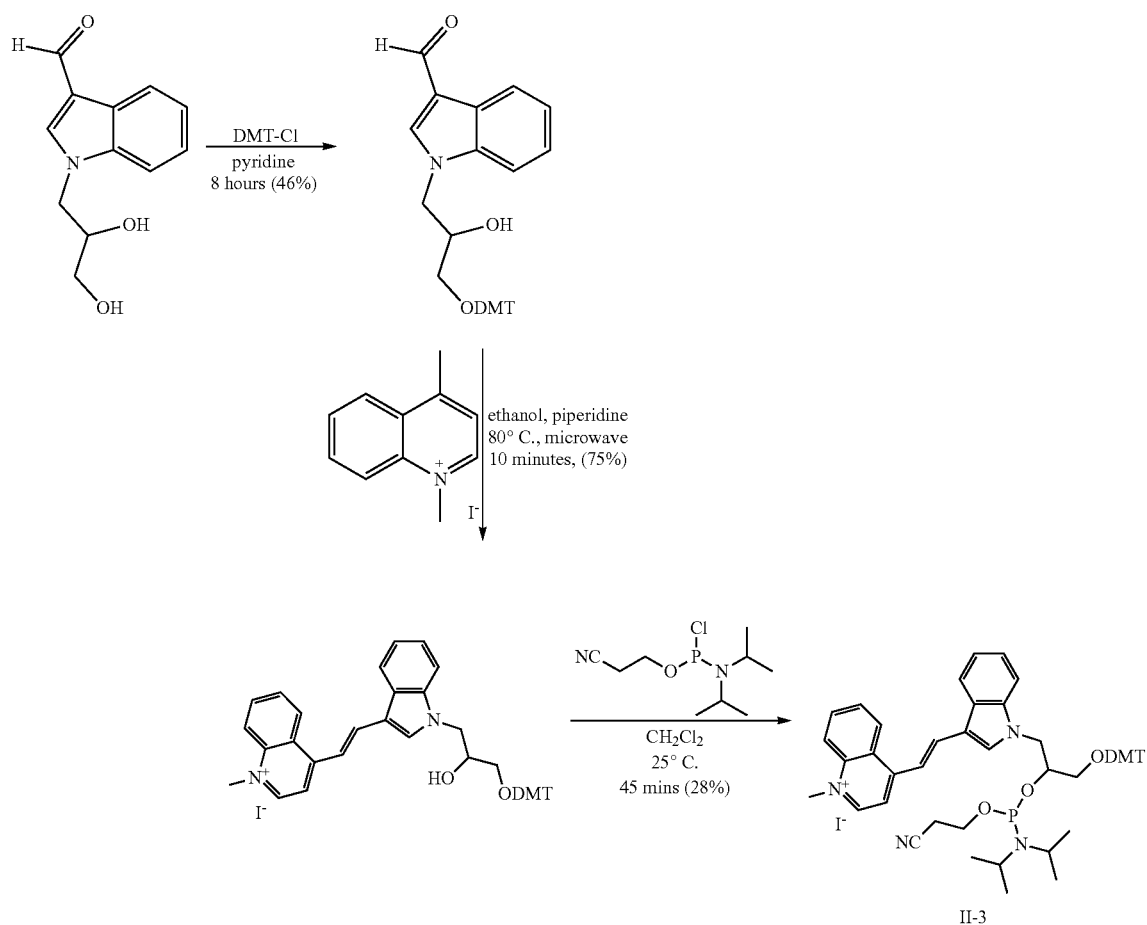
Scheme 2: Overview of 4QI-DMT phosphoramidite (compounds II-3) synthesis.

Solvatochromic and Photophysical Properties of 4QI

4QI-alcohol and 4QI-DMT contain the same fluorophore such that characterization of 4QI-alcohol is representative of the solvatochromic and photophysical capacity of the 4QI fluorophore. Fluorescence spectrometry revealed that 4QI absorbs light within the visible region and, when free in H$_2$O, exhibits $\lambda_{ex}$ and $\lambda_{em}$ maxima of 520 nm and 580 nm, respectively. Excitation and emission in the visible region as opposed to the ultraviolet (UV) region is favorable because the dye can be excited using a visible lamp rather than a more expensive UV lamp. Further characterization revealed that 4QI has a Stokes shift of 104 nm, and a moderate extinction coefficient of 26,660 L/(mol·cm).

Figure 1:
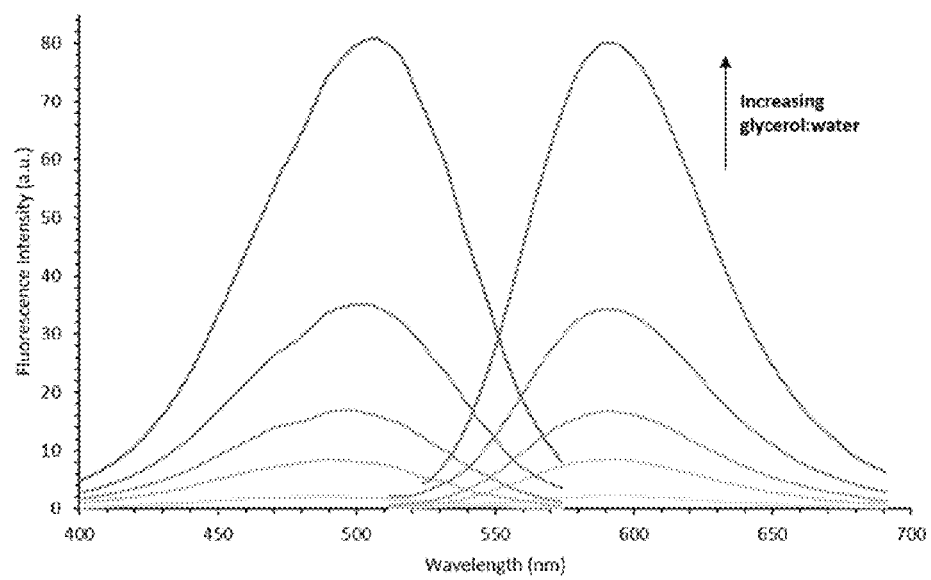
FIG. 1 shows fluorescence excitation and emission spectra of 5 µM solutions of 4QI diluted with increasing proportions MQ $H_2O$ and glycerol.

Solvent viscosity studies were preformed to determine if 4QI displays the molecular rotor capabilities characteristic of merocyanine dyes. This type of study involves observing dye fluorescence excitation and emission spectra in increasingly viscous solvents. In this case, glycerol was added to water to increase solvent viscosity without substantially altering polarity. When monitored in solutions with increasing ratios of glycerol:water, the fluorescence intensity of 4QI increased with viscosity, indicating this dye acts as a molecular rotor (FIG. 1).

Solvatochromic studies were also performed to determine how 4QI responds to solvent polarity. In contrast to viscosity studies, solvatochromic studies involve observing fluorescence spectra in solvents of varying polarity rather than viscosity. As previously explained, merocyanine dyes are known to respond to solvent polarity due to stabilization or destabilization of the TICT state. (Sasaki et al, 2016) Solvatochromic analysis revealed that the fluorescence intensity of 4QI increases and shifts to the red in solvents of decreasing polarity, and therefore confirms that this probe acts a molecular rotor (Table 2).

TABLE 2

Solvatochromic properties of 4QI.

| Solvent | Polarity Index[a] | $\lambda_{ex\,max}$ (nm) | $I_{rel}$[b] |
|---|---|---|---|
| H$_2$O | 10.2 | 486 | 1.0 |
| Acetonitrile | 5.8 | 494 | 3.6 |
| Methanol | 5.1 | 512 | 5.2 |
| THF | 4.1 | 514 | 23.9 |
| Isopropyl-alcohol | 3.9 | 523 | 28.3 |

[a]Solvent polarity relative to pentane (0.0).[64]
[b]$I_{rel} = I_{4QI}$ in solvent/$I_{4QI\,in\,H2O}$.

Preparation of Modified TBAs

Following the synthesis and characterization of 4QI, this dye was incorporated within TBA using various labelling methods. Label-free mTBA (4QI-TBA-Free) was generated by incubating 4QI-alcohol with native TBA purchased from and purified by Sigma Aldrich (Oakville, ON). End-labelled TBA (4QI-TBA-E) was synthesized by linking 4QI-alcohol to the 5' end of TBA.

Previous literature was consulted to determine an effective site for internal 4QI incorporation which would ideally favour an emissive response without inhibiting target binding. Knowing that thrombin interacts with TBA preferentially at the T-T loop residues, it was decided that the internal modification should replace one of these T residues. (Smirnov et al., 2000) As previously stated, there are four T residues within these loops which could house the internal modification: T$_3$, T$_4$, T$_{12}$ and T$_{13}$. Previous research by Cservenyi et al. in 2017 helped to narrow down the optimal site of incorporation. (Cservenyi et al., 2016) Recall that these researchers synthesized a fluorescently modified DNA nucleotide (FurdU) which was responsive to thrombin binding, and was incorporated within TBA to replace each of the natural T residues within the aptamer's T-G-T and T-T loops. (Cservenyi et al., 2016) Thrombin binding affinity varied greatly depending on the site of incorporation, however modification at T$_3$ showed the greatest emissive response to target binding while retaining high target affinity. (Cservenyi et al., 2016) Based on this data, T$_3$ was chosen as the site for TBA internal modification with 4QI-DMT, affording internally-labelled TBA (4QI-TBA-I).

Both 4QI-TBA-E and 4QI-TBA-I were prepared using in-house DNA synthesis with deprotection under UltraMild conditions and reverse-phase HPLC purification. Recall that standard conditions for oligonucleotide deprotection involve heating to 55° C. for 4 h in ammonium hydroxide (Table 3). Kinetic studies of the 4QI probe revealed that under both Standard and UltraFast deprotection conditions, 4QI absorbance was completely bleached within 6.5 h and 3 min respectively. However, the fluorescence intensity of 4QI only decreased by 11% throughout the 17-hour kinetic study under UltraMild conditions. Therefore, all mTBA were deprotected under UltraMild conditions.

TABLE 3

Deprotection conditions for synthetic oligonucleotides.

| Deprotection Method | Solution | Temp | Duration |
|---|---|---|---|
| Standard | NH$_4$OH | RT | 16 hr |
| | | 55° C. | 4 hr |
| | | 65° C. | 2 hr |
| UltraMild | 0.05M K$_2$CO$_3$ in MeOH | RT | 12 hr |
| UltraFast | 1:1 mixture (v/v) of aqueous NH$_4$OH and CH$_3$NH$_2$ | 65° C. | 5-10 min |

As the DMF-dG and Bz-dA amidites used during standard DNA synthesis contain protecting groups which cannot be removed under UltraMild conditions, phenoxyacetyl protected dA (Pac-dA) and 4-isopropyl-phenoxyacetyl protected dG (iPr-Pac-dG) were purchased. The only other amidite which contains a protecting group is Ac-dC, however the acetyl group is easily removed under UltraMild conditions. Recall, that the 3' nucleotide of a growing aptamer is tethered to a solid support throughout DNA synthesis. (Caruthers et al., 1987) Since the 3' nucleotide of synthetic TBA would be DMF-dG, an alternative solid-support bound nucleotide needed to be used. dT was therefore added to the 3' end of all mTBA, extending the aptamer length to 16 bases. A native version of this 16-mer oligonucleotide (TBA-16) was purchased and studied to confirm that the additional base does not impact aptamer structure or stability.

Results and Discussion

Impact of 4QI on TBA Structure and Stability

Thermal Melting

Thermal melting analysis demonstrated the effects of the various fluorescent modifications on the stability of the TBA.

TABLE 4

Thermal melting analysis for the mTBA series versus native TBA.

| Dye | $T_m{}^a$ $(\Delta T_m{}^b)_{GQ}$ ° C. | $T_m$ $(\Delta T_m{}^c)_{Dup}$ ° C. |
|---|---|---|
| TBA-16 | 53.6 | 64.1 |
| TBA-Free | 53.3 (−0.3) | 63.8 (−0.3) |
| TBA-E | ND$^d$ | 58.9 (−5.2) |
| TBA-I | 52.2 (−1.4) | 62.2 (−1.9) |

$^a T_m$ values in ° C. were determined from solutions of 6 µM oligonucleotide in 10% K$^+$ buffer diluted with MQ H$_2$O. Samples were monitored at 295 nm over 5 ramps at a rate of 0.5° C. min − 1.
$^b \Delta T_m = T_m$ (mTBA GQ) − $T_m$ (native TBA GQ).
$^c \Delta T_m = T_m$ (mTBA duplex) − $T_m$ (native TBA duplex).
$^d T_m$ curve could not be obtained.

Thermal melting analysis revealed that the GQ $T_m$ of TBA-16 (53.6° C.) was not significantly different than that of TBA-15 (53.5° C.), meaning the addition of an extra T at the 3'-end of TBA-15 did not affect the stability of the native aptamer. When in the presence of free 4QI, the $T_m$ of both the duplex and GQ were not significantly changed with $\Delta T_m$=−0.3° C. in both cases (Table 4). This indicates that when free in solution, 4QI does not affect the stability of the duplex nor the GQ formed by TBA.

The internal-label at position $T_3$ caused a slight decrease in GQ stability with a $\Delta T_m$ of −1.4° C. (Table 4). $T_3$ resides within one of the anterior T-T edge loops of TBA, and it is known that these loops play a role in determining GQ stability. (Cservenyi et al, 2016; Ghimire etal., 2014) Therefore, structural alterations imparted by internal modification could cause overall secondary structure destabilization. The internal-label also caused slight duplex destabilization, with a $\Delta T_m$ of −1.9° C. (Table 4). In this case, the diminished backbone structure and hydrogen bonding potential of the internal-label could be the source of decreased stability.

A GQ $T_m$ curve could not be generated for 4QI-TBA-E (Table 4). In contrast to the sigmoidal curve generated by the other mTBA, the absorbance of 4QI-TBA-E appeared to be linear and there were no clear upper or lower boundaries from which a $T_m$ could be calculated. This type of curve can occur due to additional thermal driven processes which occur before GQ unfolding, such as helix-helix transition and single-stranded base unstacking. (Lane et al., 2008) These processes have small enthalpy values which effectively broaden melting point transitions, thereby reducing the accuracy of $T_m$ calculations. (Lane et al., 2008) 4QI-TBA-E may therefore experience more complex GQ formation than the other mTBA, or perhaps form a more poorly defined overall GQ structure. Interestingly, significant GQ destabilization ($\Delta T_m$ of −9.5° C.) has been reported for another mTBA end-labelled with fluorescein (FAM). (Van Reisen et al., 2018) Together these results suggest that end-labels in general tend to have profound effects on TBA GQ stability.

Finally, duplex $T_m$ analysis for 4QI-TBA-E was successful and resulted in $\Delta T_m$=−5.2° C. (Table 4). Many merocyanine dyes, particularly positively charged molecules with short polymethine bridges, intercalate within duplex DNA. (Armitage et al., 2005) Although intercalation usually increases duplex stability, attenuation of hydrogen bonding between the nucleotides by bulky intercalators can be destabilizing and may therefore explain the decreased duplex stability in this case. (Xu et al., 2017)

Circular Dichroism

CD analysis revealed that 4QI-TBA-Free, 4QI-TBA-E and 4QI-TBA-I form similar GQ structures to that of native TBA.

Circular dichroism was used to provide insight regarding the effect of various modifications on TBA, and the effect of thrombin addition on the structure of each mTBA. Native TBA has a CD signature which clearly reflects a unimolecular, antiparallel GQ with a strong positive peak at 290 nm, and smaller positive and negative peaks at 245 nm and 260 nm, respectively. (Karsisiotis et al., 2011; Fadock et al., 2017)

Figure 2:
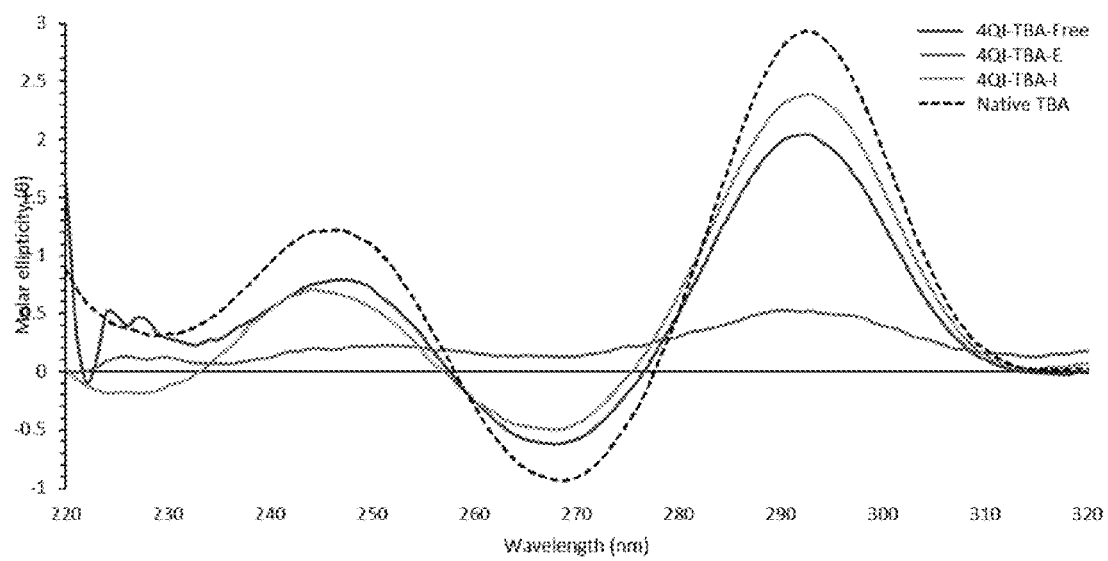
FIG. 2 shows circular dichroism spectra for 6 µM solutions of native TBA (black dashed), 4QI-TBA-Free (red), 4QI-TBA-E (blue) and 4QI-TBA-I (green) in 10% $K^+$ buffer diluted with MQ $H_2O$.

As shown in FIG. 2, all three of the mTBA have CD signatures which reflect an antiparallel GQ. In some literature reported research, fluorescent modifications cause changes in aptamer secondary structure. (Fadock et al., 2017) However, none of the modifications induced an alternative GQ structure despite causing changes in overall complex stability. 4QI-TBA-E has a notably weaker CD signal than the other modifications, which correlates with the absence of a $T_m$ curve and the notion that this strand forms a poorly defined GQ structure. Likewise, the signal intensities of 4QI-TBA-Free and 4QI-TBA-I were reduced proportionally with GQ stability.

Figure 3:
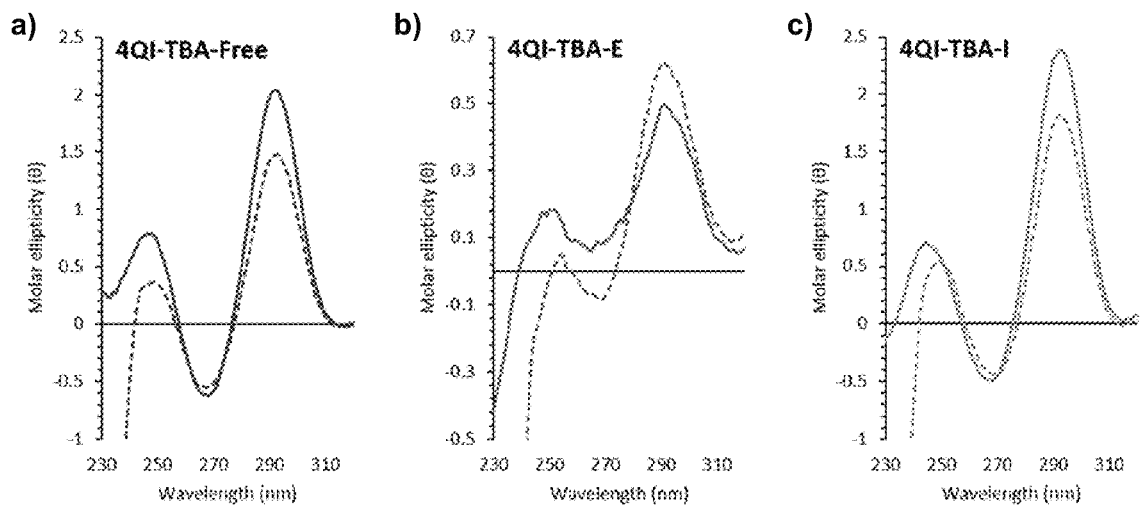
FIG. 3 shows circular dichroism spectra for 6 µM solutions of 4QI-TBA-Free (a), 4QI-TBA-E (b) and 4QI-TBA-I (c) in 10% $K^+$ buffer diluted with MQ $H_2O$ before (solid) and after (dashed) the addition of 1 eq. thrombin protein.

The effect of thrombin addition on aptamer secondary structure was observed by adding thrombin to each mTBA solution (FIG. 3). Upon the addition of thrombin to native TBA, spectral CD changes are limited to small intensity changes in each of the characteristic GQ peaks without wavelength shifts. The CD spectra of 4QI-TBA-Free and 4QI-TBA-I follow this same trend in that only small reduction in signal intensity is observed upon thrombin addition. In contrast, 4QI-TBA-E signal intensity increases at 290 nm and decreases at 260 nm, suggesting the target induces tighter GQ folding in this case. After thrombin addition, each mTBA CD spectrum shows a large, shouldered negative peak at 211 nm which is intrinsic of thrombin protein (not pictured).

Fluorescence

The fluorescence intensity and excitation and emission maxima of 4QI are modification dependent within TBA.

The fluorescence intensity of 4QI in each mTBA was observed to provide information regarding the dye's microenvironment in both duplex and GQ DNA. As described previously, merocyanine dyes show enhanced, red-shifted fluorescence in rigid, non-polar media due to the TICT phenomenon. (Sasaki et al., 2016) Thus, comparing the fluorescence of 4QI when free in solution versus bound to duplex or GQ DNA could provide insight regarding the binding modes in each case.

Figure 4:
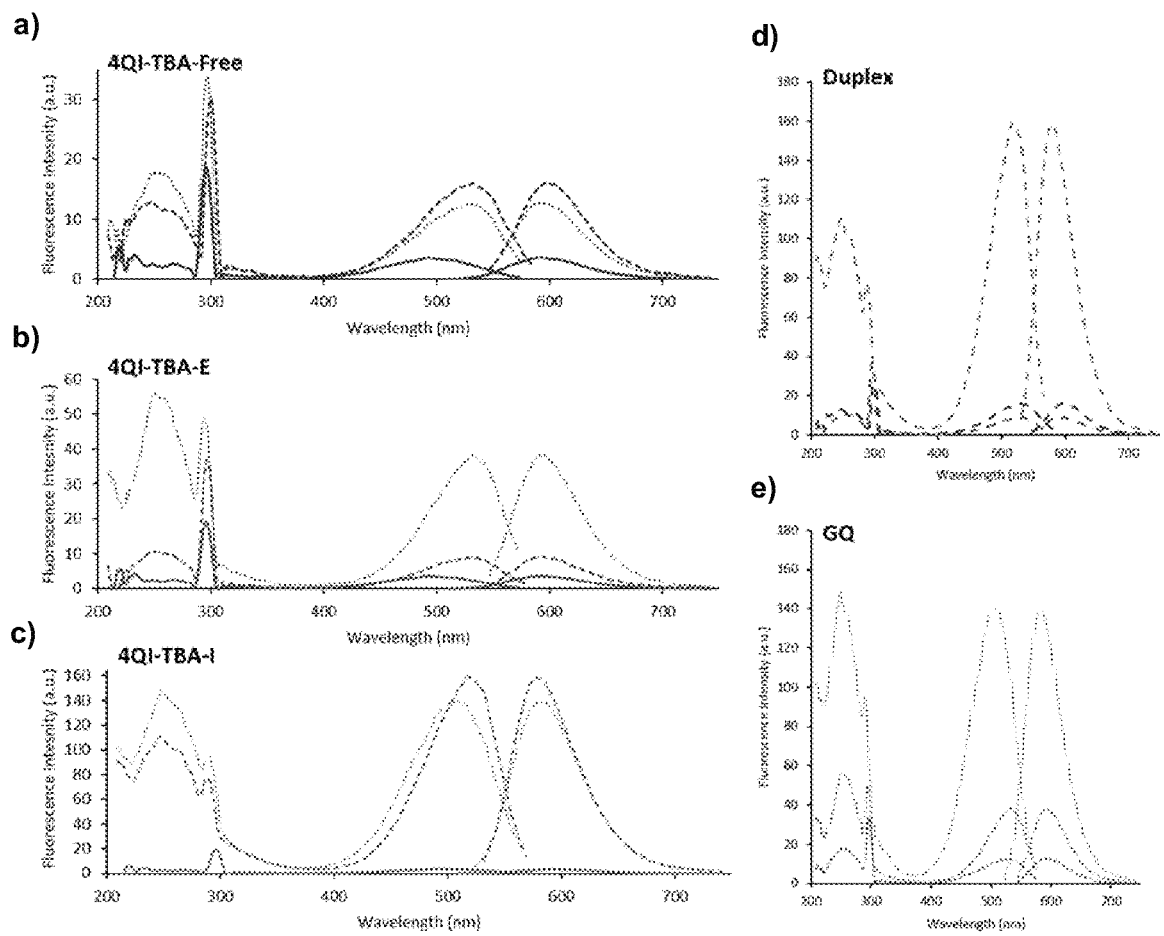
FIG. 4 shows fluorescence spectra for 2 µM solutions of 4QI-TBA-Free (a), 4QI-TBA-E (b) and 4QI-TBA-I (c) as free-dye (solid line), in duplex (d, dashed line), in GQ (e, dotted line).

Each mTBA showed distinctive fluorescence within single-stranded, duplex and GQ DNA (FIG. 4). The fluorescence intensity of 4QI-TBA-Free was increased by a factor of 3.5 when bound to GQ DNA, and 4.5 when bound to the duplex. In this case, the relative fluorescence intensity of duplex:GQ was $I_{rel}$=1.3. Regarding 4QI-TBA-E, fluorescence intensity increased by a factor of 10.8 in the GQ and 2.6 in the duplex, with a duplex:GQ $I_{rel}$=4.2. Finally, the fluorescence intensity of 4QI-TBA-I was increased by a factor of 39.4 in the GQ and 44.9 in the duplex; with a GQ:duplex $I_{rel}$=1.1.

These results show that the internal-label was the brightest mTBA in both the duplex and GQ, meaning the probe was rigidified to the greatest extent in each case. Accordingly, a two-point strand connection as seen in 4QI-TBA-I is expected to enhance rigidity by inhibiting rotation on either side of 4QI. In contrast, the single-point strand connection in 4QI-TBA-E circumvents some of this rigidity leading to the observed reduced fluorescent output. Interestingly, the free-dye was more fluorescent than the end-label in duplex DNA. Judging by the decreased duplex stability of the 4QI-TBA-E versus 4QI-TBA-Free, 4QI may stack better in the label-free system resulting in increased rigidity and therefore fluorescence. Only the end-label was more fluorescent in the GQ than the duplex, meaning this strand is amenable to a duplex-GQ exchange system which could afford a light-up response.

The fluorescence intensity resulting from the transfer of energy between DNA and dye molecules can also be used to further diagnose the interactions between these molecules. Fluorescence due to energy transfer (ET) occurs at ~256 nm, and is enhanced due to stacking interactions between guanosine nucleotides and fluorescent ligands. (Dumas et al., 2011) ET can only occur when the dye is in close proximity to DNA, either stacking in-between base pairs or onto the bottom or top faces of external G-quarters. (Kong et al., 2009) Loop binding does not give rise to ET, meaning ET intensity can be used to diagnose fluorophore binding modes. (Kong et al., 2009) Energy transfer ratios (ETRs) speak to stacking strength and can be calculated by dividing the fluorescence intensity of the ET band by the fluorescence intensity at 4QI's excitation maxima. Typically, ETRs are increased in GQ versus duplex DNA. (Dumas et al., 2011) Herein, duplex and GQ ETRs for all mTBA were calculated, along with % changes in ETR when switching from duplex→GQ form (Table 5).

TABLE 5

ETRs and percent change in ETR from duplex to GQ DNA of modified TBAs.

| mTBA | $ETR_{Dup}$ | $ETR_{GQ}$ | $\Delta ETR_{Dup \rightarrow GQ}{}^a$ |
|---|---|---|---|
| 4QI-TBA-Free | 0.807 | 1.416 | 43% |
| 4QI-TBA-E | 1.185 | 1.461 | 19% |
| 4QI-TBA-I | 0.698 | 1.064 | 34% |

$^a\Delta ETR_{Dup \rightarrow GQ}$ was calculated as $ETR_{GQ} - ETR_{Dup}/ETR_{GQ} \times 100\%$.

In the absence of DNA, 4QI does not display a peak at 256 nm (ETR=0). All mTBA had ET bands at ~256 nm from which ETRs could be calculated. As expected, all mTBA showed increased ETRs, and therefore increased stacking efficiency, when switching from duplex to GQ. Both the GQ and duplex ETRs increased by the order of 4QI-TBA-I<4QI-TBA-Free <4QI-TBA-E. Correlating the ETR results with the $T_m$ data, ETR was positively associated with GQ stability. For example, 4QI-TBA-I has the lowest $ETR_{GQ}$ and formed the least stable GQ.

Binding Studies

Fluorescence titration and fluorescence polarization revealed that all mTBA bind thrombin with reduced affinity as compared with native TBA, and that the fluorescent response to the target is modification specific.

Fluorescence thrombin-aptamer titrations were performed to monitor the site-specific emissive response of 4QI to protein binding, and FP titrations were performed to determine the thrombin binding affinity of each mTBA. Ideally the binding data herein would be compared to that of native TBA to draw conclusions regarding how modification type and location impact target binding affinity. However, the reported $K_d$ for native TBA was calculated using isothermal titration calorimetry, which cannot be accurately compared to data generated from a different analytical technique. (Pagano et al., 2008) FP binding data for TBA 5' end-labelled with FAM was therefore used as a comparison in this work ($K_d$=4.9 µM). (Van Riesen et al. 2018)

Figure 5:
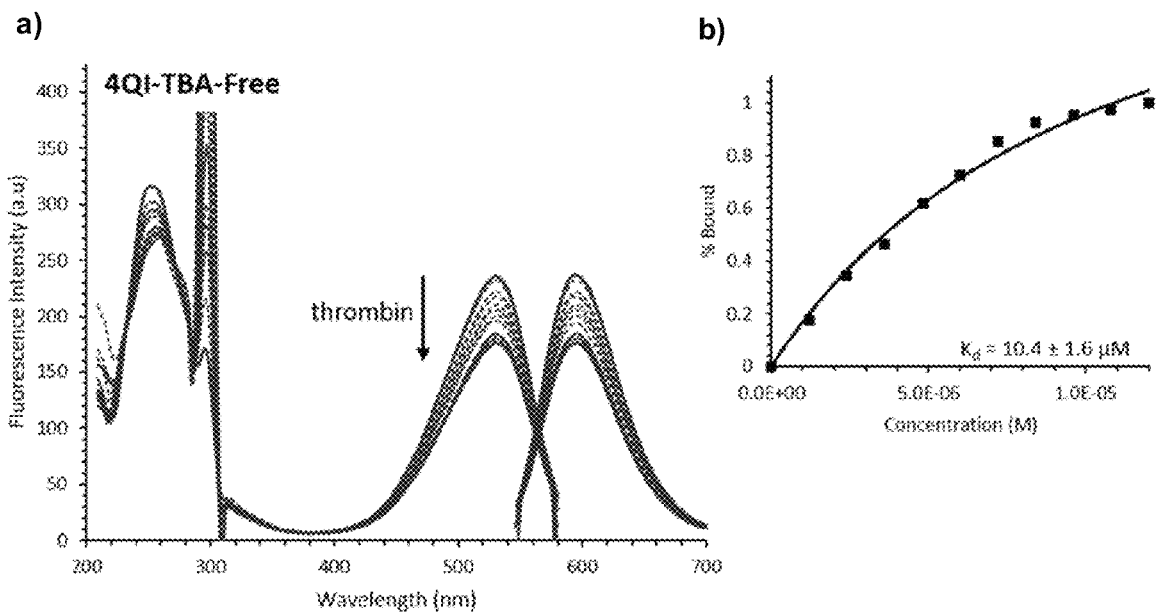
FIG. 5 shows fluorescence titration spectra (a) and fluorescence polarization binding data (b) of 6 µM 4QI-TBA-Free with 2 eq. thrombin in 10% $K^+$ buffer diluted with MQ $H_2O$.

Titration of 4QI-TBA-Free with thrombin protein caused small decreases in fluorescence intensity which plateaued at approximately 1 equivalent, corresponding to a 24% decrease in fluorescence intensity (FIG. 5). The magnitude of ET as indicated by the intensity of the ET band at 260 nm also decreased with thrombin addition, suggesting that 4QI is displaced from the GQ upon thrombin binding. To assess the binding affinity of thrombin for 4QI-TBA-Free, FP was performed wherein titration of thrombin into the mTBA solution resulted in reduction of FA proportional to thrombin binding. The data from this titration fitted a one-site saturation (OSS) binding model well ($R^2$=0.9911), yielding a $K_d$ of 10.4±1.6 µM. This $K_d$ is approximately 5 µM higher than that of 5'-FAM TBA, meaning 4QI binding further reduced the aptamer's affinity for thrombin. (Cservenyi et al., 2016)

Figure 6:
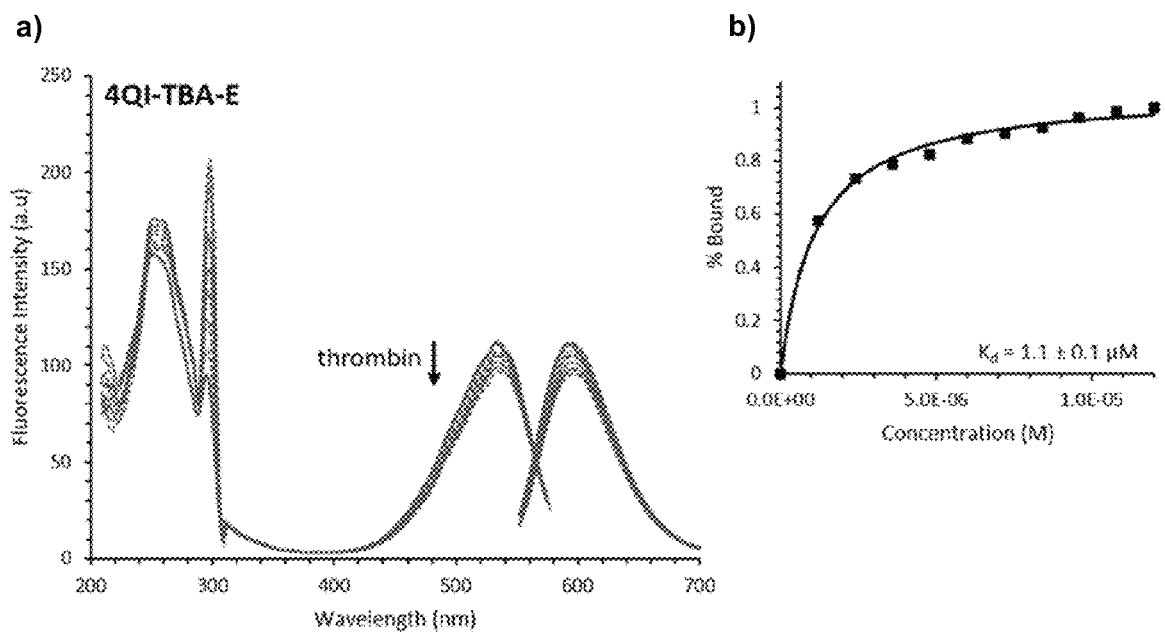
FIG. 6 shows fluorescence titration spectra (a) and FP binding data (b) of 6 µM 4QI-TBA-E with 2 eq. thrombin in 10% $K^+$ buffer diluted with MQ $H_2O$.

While titration of 4QI-TBA-E with thrombin protein also caused reduction in fluorescence intensity, this decrease was minimal and consistent indicating that the observed response was due to sample dilution rather than target binding (FIG. 6). The magnitude of the ET band was increased slightly upon thrombin addition, indicating that 4QI was not displaced from the GQ in this case. Interestingly, addition of thrombin to 4QI-TBA-E reduced FA in a fashion which closely fits a OSS model ($R^2$=0.9946), affording a low $K_d$ of 1.1±0.1 µM. Together, this information suggests that while thrombin was able to bind 4QI-TBA-E with advanced affinity over 5'-FAM TBA, no quantifiable fluorescent response was produced. (Van Riesen et al. 2018)

Figure 7:
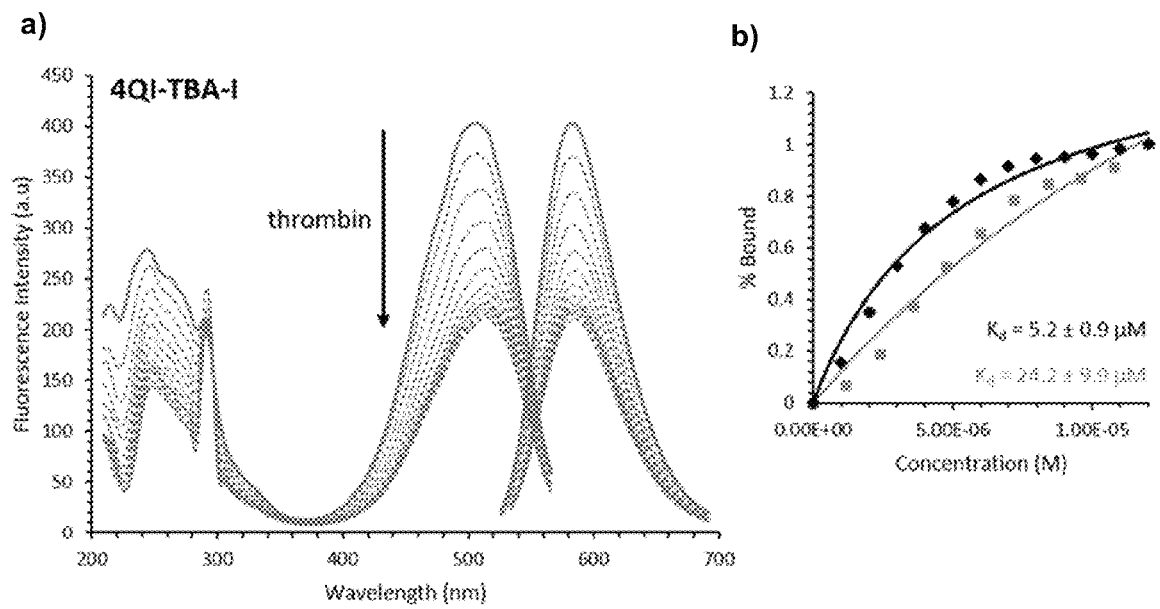
FIG. 7 shows fluorescence titration spectra (a), fluorescence binding data (b, diamond line) and FP binding data (b, square line) of 6 µM 4QI-TBA-I with 2 eq. thrombin in 10% $K^+$ buffer diluted with MQ $H_2O$.

Titration of 4QI-TBA-I with thrombin protein caused a dramatic 46% decrease in fluorescence intensity which plateaued at approximately 1 equivalent of thrombin (FIG. 7). As with the label-free assay, the ET intensity of 4QI-TBA-I decreased with thrombin addition indicating dye displacement. Changes in $\lambda_{em}$ maxima reasonably fit an OSS binding curve ($R^2$=0.9842), yielding a $K_d$ of 5.6±0.9 µM (FIG. 7, diamond line). Fluorescence polarization titration also reasonably fit the same model ($R^2$=0.9788) but yielded a higher binding constant of 24.4±9.9 µM (FIG. 7, square line). This difference can be attributed to differences in method sensitivity, demonstrated by the low error and better fit of the fluorescence titration corresponding to the more sensitive method. When accounting for experimental error, the lowest calculated $K_d$ was not significantly different that of 5'-FAM TBA, indicating the internal-modification herein was comparable in terms of binding affinity to the 5'-FAM end-label.

Figure 8:
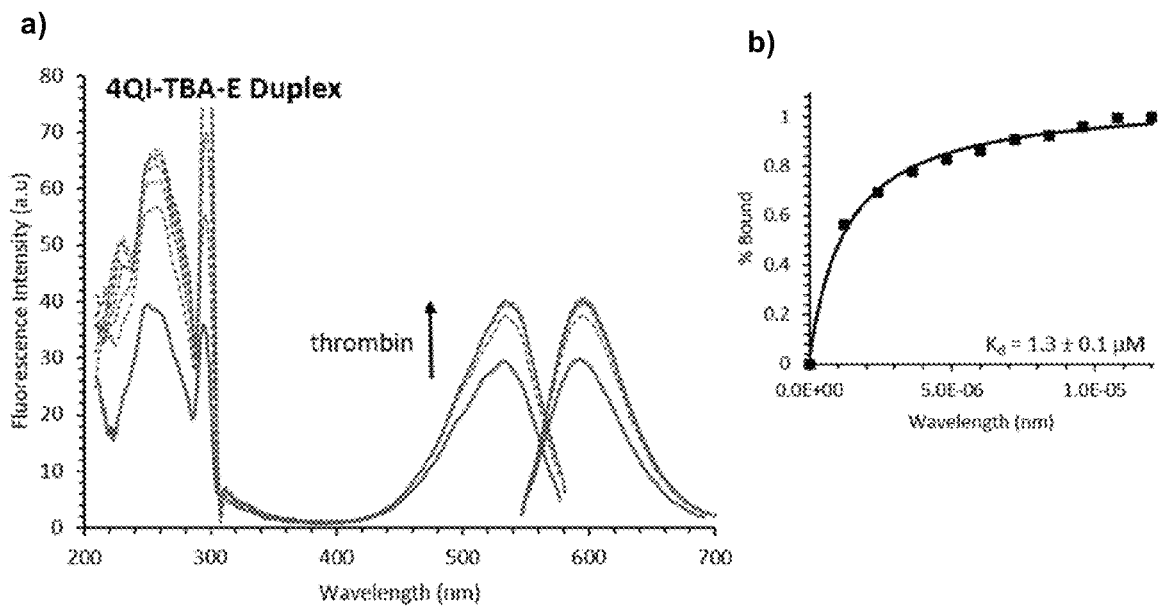
FIG. 8 shows fluorescence titration spectra (a) and FP binding data (b) of 3 µM 4QI-TBA-E and 3.3 µM TBA-C9 duplex with 1.2 eq. thrombin in 10% $K^+$ buffer diluted with MQ $H_2O$.

Thrombin titration of the duplex formed by 4QI-TBA-E and a 9-mer, 3'-5' antisense complementary DNA (cDNA) strand caused a 36% increase in the fluorescence intensity which plateaued at approximately 1 equivalent of thrombin (FIG. 8). ET intensity increased accordingly, suggesting that as the duplex dissociates, 4QI stacks upon the newly formed GQ. FP titration yielded data which closely fit a OSS binding model ($R^2$=0.9939), with a low $K_d$ of 1.3±0.1 µM. This binding constant is nearly equal to that of the 4QI-TBA-E GQ assay (1.1 µM), meaning thrombin has a similar affinity for 4QI-TBA-E in each case. In this case, the observed increase in fluorescence intensity occurs as thrombin binding thrusts the labelled aptamer from a duplex to GQ environment, where 4QI fluorescence is notably higher. In contrast to the GQ assays already presented, the fluorescent response herein was "Signal-On". This result is exciting because assays which result in signal enhancement are typically more sensitive and therefore favourable over "Signal-Off" assays. (Wang et al. 2011)

TABLE 6

Summary of fluorescence, binding and ET data for the mTBA series.

| mOTAA | $K_d^a$ (µM) | % displacement[b] | $ETR_{GQ}$ |
|---|---|---|---|
| 4QI-TBA-Free | 3.4 ± 0.3 | 24 | 1.416 |
| 4QI-TBA-E | 1.5 ± 0.3 | 13 | 1.461 |
| 4QI-TBA-I | 5.2 ± 0.9 | 46 | 1.064 |

[a] Resulting from the most sensitive titration.
[b] % displacement = $(E_{initial} - E_{plateau})/E_{initial} \times 100$.

The fluorescence and binding data relating to the GQ assays in this section along with relevant ETR data are summarized (Table 6). All the mTBA formed antiparallel GQs and retained their thrombin binding ability, despite backbone disruption and elimination of some hydrogen binding due to internal- and end-labelling. Despite slight to moderate GQ destabilization, all the mTBA bound thrombin with an equal to or better affinity than 5'-FAM TBA. Two of the mTBA displayed a quantifiable emissive response to thrombin binding, characterized by decreased fluorescence intensity which is attributed to probe displacement from the GQ and into more polar, less rigid surrounding media.

4QI-TBA-E was the only mTBA which did not show a fluorescent response to thrombin, a phenomenon which could be related to modification site and/or the aptamer's stacking potential. The end-label was incorporated on the top face of the aptamer which does not interact directly with the thrombin protein, so that target binding may not produce a big enough change in this probe's local environment to cause a fluorescent response. Another explanation could be that since 4QI-TBA-E has the greatest stacking potential of the mTBA, the target may have difficulty in displacing the dye in this case.

4QI-TBA-I was the most successful mTBA, with the lowest $K_d$ and the greatest % displacement. The success of this modification is likely explained by the site of 4QI incorporation, which is directly within the target binding site for this aptamer and therefore experiences the maximal change in local environment upon target binding. 4QI-TBA-I also had the weakest stacking potential, which could have further favored probe displacement relative to the other mTBA. 4QI-TBA-Free also responded fluorescently to thrombin binding but was less effective than the internal-label in terms of binding affinity and % displacement. In this case, the decreased displacement efficiency could be related to a relatively higher stacking potential or probe binding to the GQ face which is not in direct contact with the target protein.

Altogether, these results show that thrombin detection can be achieved using a merocyanine dye as a label-free, end-label and internal-label within TBA. Melting analysis revealed that aptamer stability is both modification dependent and duplex versus GQ specific. CD analysis showed that all mTBA adopt the same antiparallel GQ conformation as native TBA, and that this conformation is maintained upon thrombin binding. Further, CD signal strength was positively correlated with GQ stability. The intrinsic fluorescence of each mTBA usually increased when going from a single-stranded→duplex→GQ environment, except for 4QI-TBA-E which was brightest in the duplex. Thrombin binding reduced 4QI-TBA-Free fluorescence by 24%, with a binding affinity roughly double that of 5'-FAM TBA. The internal-label responded even better to thrombin, with a 46% decrease in florescence intensity a binding affinity which not significantly different from 5'-FAM TBA. As demonstrated by FP, 4QI-TBA-E bound thrombin with an even higher affinity than 5'-FAM TBA, however no quantifiable fluorescent response was produced. Using a duplex→GQ assay, the binding affinity of 4QI-TBA-E was retained while achieving a 36% decrease in fluorescence intensity. These binding results, together with information regrading aptamer structure and stability, emphasize the importance of modification site in developing successful fluorometric aptamer-based detection assays.

Example 3: Incorporation of 4QI within the Ochratoxin-A (OTA) Aptamer

Ochratoxin-A (OTA) is an abundant foodstuff contaminant which is produced by *Aspergillus* and *Penicillium* fungus (shown below). (Pohland et al., 1992) This mycotoxin accumulates as a secondary metabolite within improperly stored cereal and grain products, and is known to be acutely and sub-chronically nephrotoxic leading to kidney failure. (Pfohl-Leszkowicz et al., 2007) OTA attracted worldwide attention when the International Agency for Research on Cancer classified OTA as a possible human carcinogen. (IARC Working Group, 2002) As a result, OTA detection has been a focus in the field of small molecule detection, prompting several research groups to select DNA aptamers for OTA. (Cruz-Aguado et al., 2008; Barthelmebs et al., 2011; McKeague et al., 2014) One of these ochratoxin-A aptamers (OTAA) is 31 bases long and binds OTA with an affinity of 0.5 µM. (Cruz-Aguado et al., 2008) Many research groups have worked to characterize this aptamer, and although no crystal structure has been generated it is known that OTAA forms a unimolecular, antiparallel G-quadruplex. (Dumas et al., 2011)

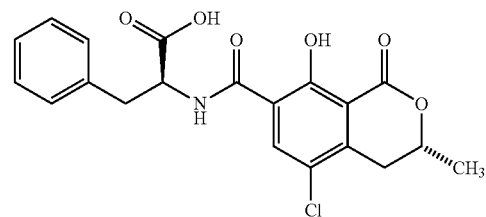 [SMILES: C[C@@H]1Cc2c(Cl)cc(C(=O)N[C@@H](Cc3ccccc3)C(=O)O)c(O)c2C(=O)O1]

Chemical structure of ochratoxin-A. (Pfohl-Leszkowicz et al., 2007)

To date, there have been no reports of OTA detection using internally-labelled OTAA, or end-labelled OTAA without requiring a quencher molecule. Further, there has been no reported investigation regarding the utility of a single fluorophore in OTA detection using different OTAA labelling strategies. Experiments were conducted to develop fluorometric aptasensors for OTA using label-free, end-labelled and internally-labelled OTAA with merocyanine 4QI dye and to compare the utility of these three DNA aptasensors in OTA detection.

Preparation of Modified OTAAs

As with the synthesis of the mTBA series, 4QI was incorporated within OTAA using various labelling methods. Label-free mOTAA (4QI-OTAA-Free) involved incubating 4QI-alcohol with native OTAA purchased from and purified by Sigma Aldrich (Oakville, ON). To create end-labelled OTAA (4QI-OTAA-E), 4QI-alcohol was attached to the 5' end of OTAA using in-house DNA synthesis.

Creating internally-labelled OTAA was more complicated because the label could be incorporated at 31 different positions within OTAA. Selecting modification locations which would not prevent OTA binding, but were also amenable to microenvironmental alteration was paramount to assay success.

Figure 9:
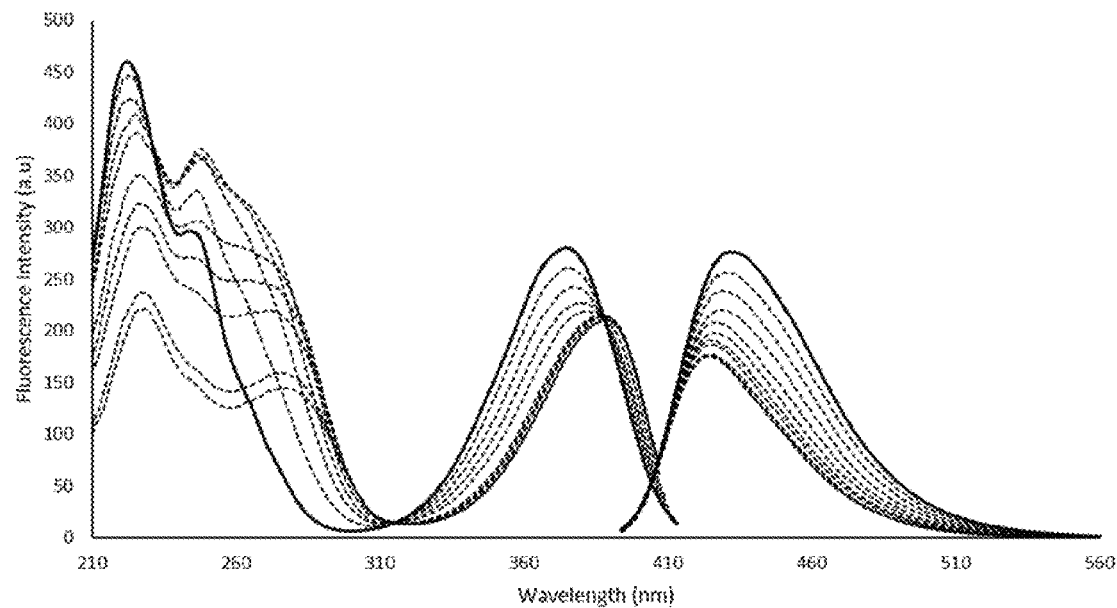
FIG. 9 shows fluorescence titration of 3 µM OTA with 3 eq. modified OTAA ($G_{13}$ replaced by T) in 10% OTAA binding buffer diluted with MQ $H_2O$.

Fluorescence titrations were performed with the goal of determining OTAA nucleobases favourable for structural modification. OTAA was systematically modified at different positions wherein native nucleobases were replaced with alternative natural nucleobases (e.g., $G_{13}$ was replaced with T). Fluorescence titration revealed that all the modifications within the OTAA tails and at $G_9$ eliminated OTA binding affinity, suggesting these regions are critical for OTA binding. OTA binding affinity was only slightly reduced due to modification at $G_{13}$ and $T_{19}$, suggesting these bases could be altered without preventing target binding (FIG. 9).

Therefore, positions $G_{13}$ and $T_{19}$ were chosen as sites for internal OTAA modification with 4QI-DMT, affording 4QI-OTAA-13 and 4QI-OTAA-19, respectively. As these sites reside on different faces of the aptamer, analysis of these internal labels was expected to provide structural information regarding the OTAA binding site.

Finally, as with the mTBA series, all end-labelled and internally-labelled mOTAA were prepared using in-house DNA synthesis with deprotection using UltraMild conditions and reverse-phase HPLC purification. UltraMild Pac-dA and iPr-Pac-dG were used in addition to standard Ac-dC and dT amidites during DNA synthesis. Since cytosine is the 3' nucleotide of native OTAA, an alternative solid support column was not required.

Results and Discussion
Impact of 4QI on OTAA Structure and Stability
Thermal Melting Thermal melting analysis revealed that modification of OTAA with 4QI impacts aptamer stability in a modification-dependent manner.

TABLE 7

Thermal melting analysis for the mOTAA series versus native OTAA.

| mOTAA | $T_m^a$ ($\Delta T_m^b$)$_{GQ}$ |
|---|---|
| Native OTAA | 51.1 |
| 4QI-OTAA-Free | 64.2 (13.1) |
| 4QI-OTAA-E | 45.6 (−5.5) |
| 4QI-OTAA-13 | 54.8 (3.7) |
| 4QI-OTAA-19 | 50.2 (−0.9) |

$^a T_m$ values in ° C. were determined from solutions of 6 μM oligonucleotide in 10% OTABB diluted with MQ H$_2$O. Samples were monitored at 295 nm over 5 ramps at a rate of 0.5° C. min − 1.
$^b \Delta T_m = T_m$ (mOTAA GQ) − $T_m$ (native OTAA GQ).

The thermal melting results of the mOTAA series are outlined in Table 7. 4QI-OTAA-19 was the only modification which only slightly reduced GQ stability, with a $\Delta T_m$ of −0.9° C. Position $T_{19}$ resides within the largest edge loop of OTAA, and as previously stated, loops are thought to be a major source of aptamer stability. (Ghimire et al., 2014) Therefore, structural alternation imparted by internal loop modification could cause overall secondary structure destabilization in this case.

Both 4QI-OTAA-Free and 4QI-OTAA-13 had stabilizing effects with $T_m$s which were greater than that of native OTAA by 13.1° C. and 3.7° C., respectively. As stacking interactions typically increase GQ stability, probe stacking is likely responsible for this observed stabilization. (Ghimire et al., 2014; Lane et al., 2008) Though they followed the same trend, the stabilizing effect of 4QI was much more pronounced for 4QI-OTAA-Free than 4QI-OTAA-I. Considering there are no covalent structural disruptions to overcome in the label-free system, it is unsurprising that 4QI-OTAA-Free was able to achieve much greater stabilization.

Unlike the label-free or internal-label modifications, 4QI-OTAA-E caused significant destabilization of OTAA with a $\Delta T_m$ of −5.5° C. As previously mentioned, OTAA tails are thought to be crucial for OTA binding, meaning these tails could also play a role in stabilizing the GQ aptamer structure. (Ghimire et al., 2014) Thus, it is reasonable to propose that inserting a bulky fluorescent ligand onto the end of one of these tails could lead to GQ destabilization.

Circular Dichroism

CD analysis revealed that all the fluorescent modifications herein caused structural alterations compared to the native OTAA GQ.

Figure 10:
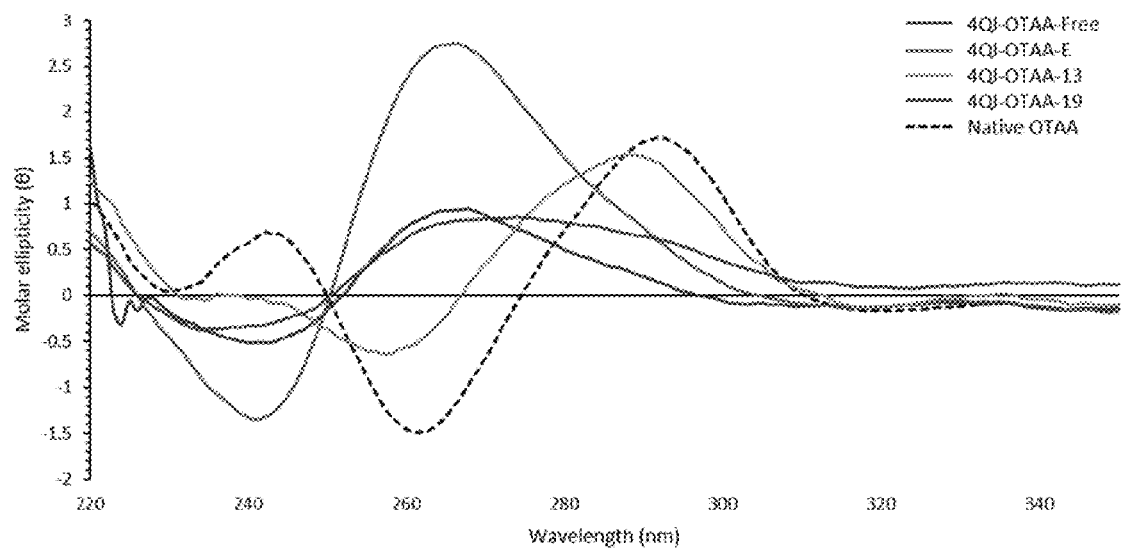
FIG. 10 shows circular dichroism spectra for 6 µM samples of native OTAA (black dashed), 4QI-OTAA-Free (red), 4QI-OTAA-E (blue) and 4QI-OTAA-13 (green) ad 4QI-OTAA-19 (purple) in 10% OTABB diluted with MQ $H_2O$.

Native OTAA forms a unimolecular, antiparallel GQ with strong positive and negative peaks at 290 nm and 260 nm, and a smaller positive peak at 240 nm (FIG. 10). Comparative CD analysis of the modified OTAA strands was used to visualize how each modification type influences aptamer secondary structure.

Both 4QI-OTAA-Free and 4QI-OTAA-E showed radically different CD spectra from native OTAA, each with a strong positive peak at 265 nm and a smaller negative peak at 240 nm (FIG. 10). These peaks are representative of a parallel GQ, meaning OTAA switches from an antiparallel to a parallel GQ both in the presence of 4QI and when 4QI is tethered to the 5'-end. Recall that 4QI-OTAA-Free was significantly more stable than the other mOTAAs, and since this aptamer forms a parallel GQ, it is reasonable to propose that in addition to stacking interactions this alternate GQ structure could be inherently more stable. However, this theory is easily disputed when considering that 4QI-OTAA-E also forms a parallel GQ but is significantly destabilized as compared to native OTAA. More likely, the major stabilizing force within 4QI-OTAA-Free is indeed probe stacking.

4QI-OTAA-13 shows only slight change in GQ topology as compared to native OTAA (FIG. 10). Specifically, both the 290 nm and 260 nm peaks are blue shifted towards those indicative of a parallel GQ. In contrast, 4QI-OTAA-19 has a broad peak spanning 260-290 nm which indicates that this GQ has strong antiparallel and parallel attributes. Thus, it is postulated that both 4QI-OTAA-13 and 4QI-OTAA-19 form hybrid GQs with antiparallel and parallel character, while the former more closely resembles the native antiparallel GQ. Recall that the GQs of both internally-modified mOTAA were destabilized. This result lends itself to the idea that hybrid GQs are inherently less stable than their parallel or antiparallel counterparts, however structural disruption could also cause the observed destabilization.

Figure 11:
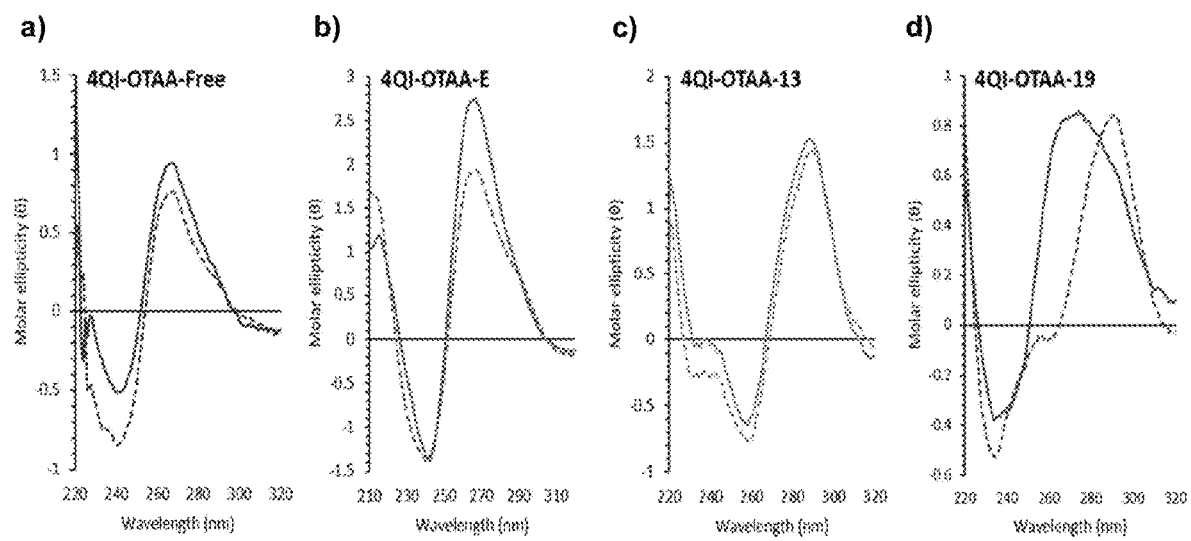
FIG. 11 shows circular dichroism spectra for 6 µM solutions of 4QI-OTAA-Free (red), 4QI-OTAA-E (blue), 4QI-OTAA-13 (green) and 4QI-OTAA-19 (purple) in 10% OTABB diluted with MQ $H_2O$ before (solid) and after (dashed) the addition of 1 eq. OTA.

The effect of OTA on aptamer secondary structure was observed by adding OTA to each mOTAA solution (FIG. 11). When native OTAA binds OTA, the intensity of the 260 nm and 290 nm peaks slightly decrease and increase, respectively. For 4QI-OTAA-Free and 4QI-OTAA-E, addition of OTA caused the 240 nm and 265 nm peaks to decrease slightly, with the emergence of a shoulder at 290 nm. Thus, it appears that OTA interacts with each of these mOTAA and encourages antiparallel GQ character. This effect is further pronounced with 4QI-OTAA-19, where the addition of OTA causes disappearance of the 260 nm peak with the emergence of a strong 290 nm peak. This drastic shift indicates that OTA addition completely reverts this GQ back to its native antiparallel structure. In contrast, the CD spectral changes of the other internal-label, 4QI-OTAA-13, are limited to small decreases in the intensity of the 260 nm and 290 nm peaks upon OTA addition. This decreased peak intensity without wavelength shifts suggests that OTA was unable to bind 4QI-OTAA-13.

Fluorescence

The fluorescence intensity and wavelength maxima of 4QI is modification dependent within OTAA.

The fluorescence intensity of 4QI in each mOTAA was observed to provide information regarding the dye's microenvironment in each case. Recall that 4QI has molecular rotor character, and therefore displays increased fluorescence intensity in relatively non-polar, viscous media.

Figure 12:
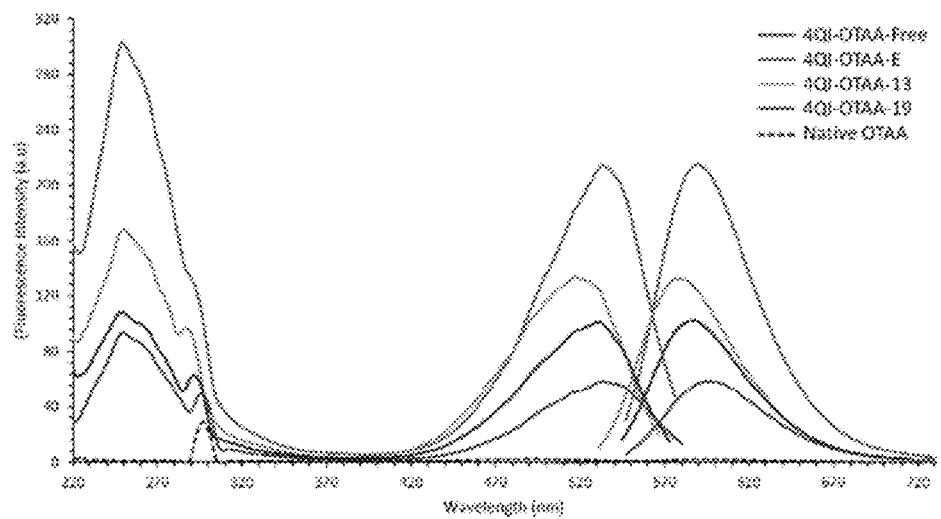
FIG. 12 shows fluorescence spectrafor 2 µM solutions of 4QI free dye (black, dashed), 4QI-OTAA-Free (red), 4QI-OTAA-E (green), 4QI-OTAA-13 (blue) and 4QI-OTAA-19 (purple) in 10% OTABB diluted with MQ $H_2O$.

Each mOTAA showed distinctive fluorescence within single-stranded and GQ DNA (FIG. 12). The fluorescence intensity of 4QI increased upon binding to OTAA in the GQ form with an $I_{rel}$=23.2. This fluorescence was increased even higher when 4QI was incorporated as an internal-label, with $I_{rel}$=52.6 and $I_{rel}$=40.6 for 4QI-OTAA-13 and 4QI-OTAA-19, respectively. Finally, 4QI had the greatest intensity when incorporated as an end-label, with an $I_{rel}$=85.3. This result is surprising, considering that the TBA internal-label herein (4QI-TBA-I) was more rigid, and therefore more fluorescent than the end-label (4QI-TBA-E). The main difference here is that the OTAA end-label is situated near two long hydrophobic tails. (Fadock et al., 2017) Therefore, general steric restriction, along with non-specific tail binding and probe stacking, could collectively play a role in the elevated fluorescence of 4QI-OTAA-E.

Recall that, in the absence of DNA, 4QI does not display a peak at 256 nm (ETR=0). All the mOTAA displayed ET, meaning that 4QI either stacks between or onto the external faces of the OTAA G-tetrads. As shown, the ETRs increase by the order of 4QI-OTAA-19<4QI-OTAA-13<4QI-OTAA-E<4QI-OTAA-Free (Table 8). All the mOTAA had ETR >1, meaning ET intensity was greater than emission intensity, thus indicating excellent stacking ability. These ETR therefore support the suspicion of strong probe stacking, which likely plays an important role in the GQ stability of the mOTAA series.

TABLE 8

ETRs of mOTAA GQ.

| mOTAA | $ETR_{GQ}$ |
| --- | --- |
| 4QI-OTAA-Free | 1.604 |
| 4QI-OTAA-E | 1.409 |
| 4QI-OTAA-13 | 1.269 |
| 4QI-OTAA-19 | 1.059 |

Binding Studies

Fluorescence titration revealed that both 4QI emission and OTA binding affinity were greatly impacted by modification location within OTAA.

OTA is unique from thrombin because it is intrinsically fluorescent with $\lambda_{ex}$ and $\lambda_{em}$ maxima at 375 nm and 432 nm, respectively. (Fadock et al., 2017) Upon binding to OTAA, OTA fluorescence decreases drastically, with an isosbestic point around 315 nm and bathochromic (red) and hypsochromic (blue) shifted $\lambda_{ex}$ and $\lambda_{em}$ maxima, respectively. (Fadock et al., 2017) Thus, binding affinity can be determined using fluorescence spectrometry such that FP is not required. Two types of fluorescence titrations were therefore performed herein, where either the dye's fluorescence or intrinsic OTA fluorescence were monitored with the addition of OTA or mOTAA, respectively. The comparative $K_d$ value used for native OTAA was previously determined by Fadock and Manderville using fluorescence spectrometry to be 1.1 μM. (Fadock et al., 2017)

Figure 13:
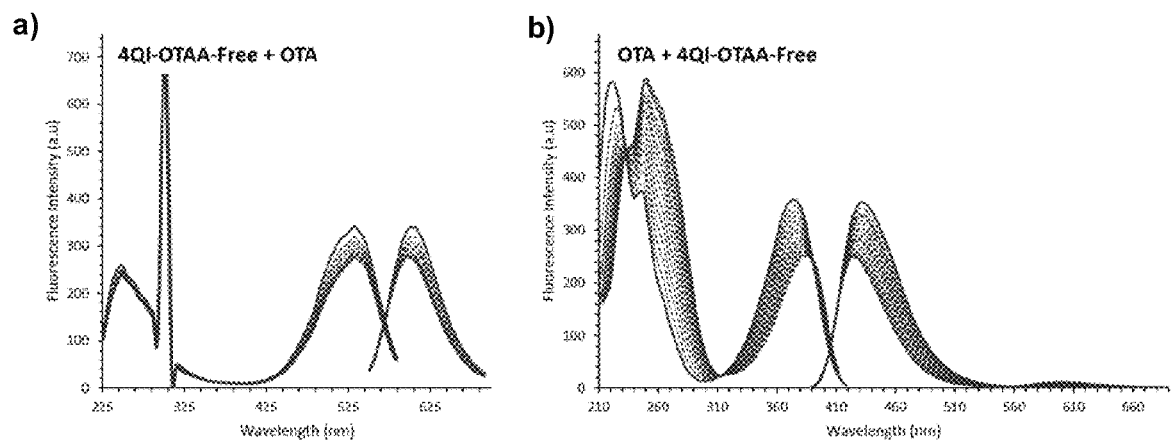
FIG. 13 shows fluorescence titration of (a) 6 µM 4QI-OTA-Free with 2 eq. OTA and (b) 6 µM OTA with 3.4 eq. 4QI-OTAA-I both in 10% OTABB diluted with $H_2O$.

When OTA was titrated into 4QI-OTAA-Free, the fluorescence intensity of 4QI decreased and plateaued at approximately 1 equivalent, corresponding to a 20% decrease in fluorescence intensity (FIG. 13A). Binding data from this titration closely fit a OSS binding model ($R^2$=0.9911), yielding a binding constant of 3.4±0.3 μM. Considering the reverse titration, OTA fluorescence was quenched upon addition of an OTAA-4QI complex, with red and blue shifted $\Delta_{ex}$ and $\lambda_{em}$ maxima (FIG. 13B). Further, the ET intensity of OTA increased throughout the titration with a clear isosbestic point at 315 nm. The binding data from this titration also fit the binding curve well ($R^2$=0.9958) but yielded a slightly higher binding constant of 8.5±0.6 μM. The discrepancy between the calculated $K_d$ values reflects differences in fluorescence sensitivity when using either the aptamer or the target as a fluorescent source, but together provide strong evidence of OTA binding to 4QI-OTAA-Free.

Figure 14:
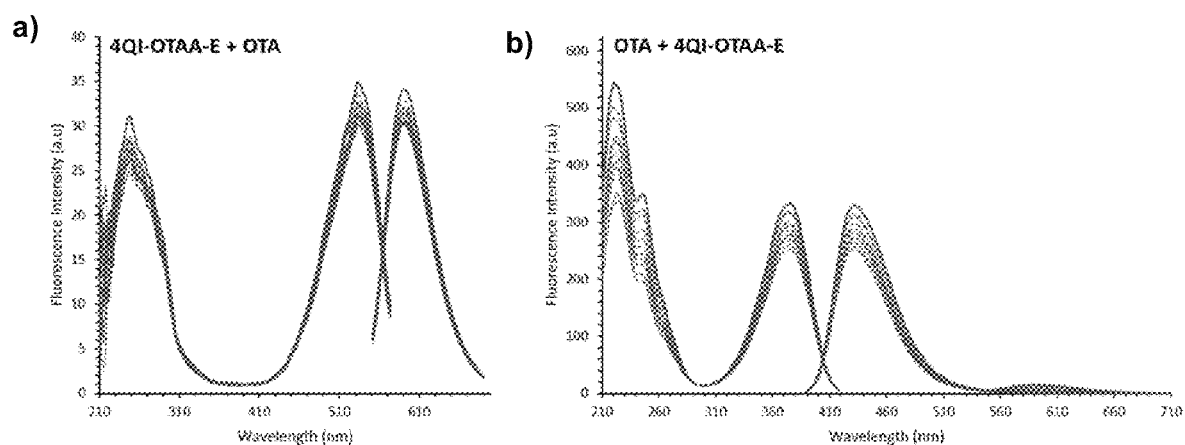
FIG. 14 shows fluorescence titration of (a) 6 µM 4QI-OTA-E with 2 eq. OTA and (b) 6 µM OTA with 2 eq. 4QI-OTAA-E both in 10% OTABB diluted with $H_2O$.

Titration of 4QI-OTAA-E with OTA caused slight, consistent decreases in 4QI fluorescence intensity which did not appear to plateau after the addition of 2 equivalents (FIG. 14A). However, the binding data weakly fit a OSS binding curve ($R^2$=0.9615), corresponding to a $K_d$ 1.5±0.3 μM. When 4QI-OTAA-E was titrated into a solution of OTA, the fluorescent intensity of OTA was reduced following the same trend (FIG. 14B). Further, the ET intensity of OTA decreased consistently throughout the titration and there was no observable isosbestic point. The binding data from this titration fit a linear trend with nearly the same variability as a OSS model ($R^2$=0.9885 and $R^2$=0.9865, respectively), yielding a large binding constant (42±3 μM) suggestive of weak to no OTA binding. This $K_d$ conflicts with that generated from the former titration, an effect which could also be due to differences in fluorophore sensitivity. However, considering the absence of wavelength shifts and isosbestic points in both titrations, along with decreased energy transfer to OTA, there does not appear to be strong binding between OTA and 4QI-OTAA-E.

Figure 15:
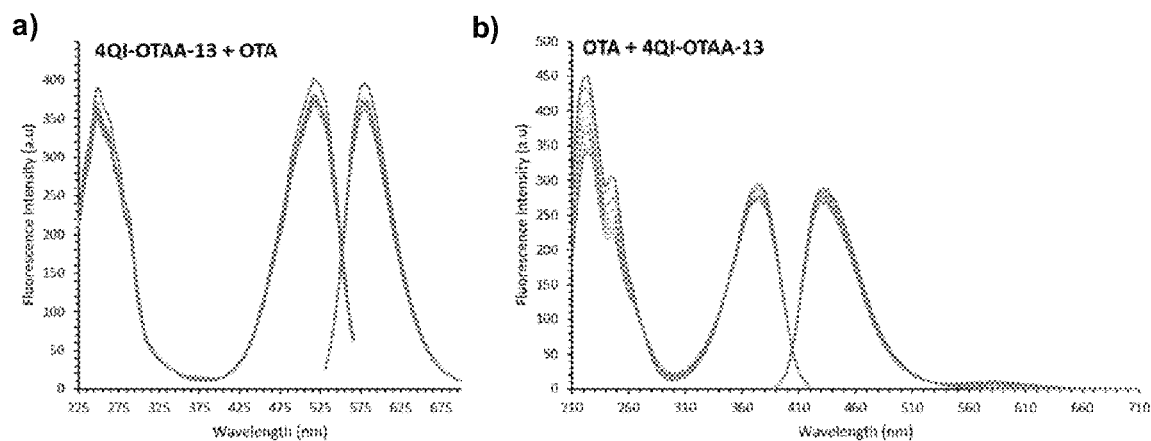
FIG. 15 shows fluorescence titration of (a) 6 µM 4QI-OTA-13 with 2 eq. OTA and (b) 6 µM OTA with 2 eq. 4QI-OTAA-13 both in 10% OTABB diluted with $H_2O$.

Titration of 4QI-OTAA-13 followed the same trend as the end-label, namely small, inconsistent decreases in 4QI fluorescence intensity which did not plateau after 2 equivalents of OTA (FIG. 15A). Although a low $K_d$ could be calculated from this titration data (0.7±0.2 μM), this binding curve had relatively large variability ($R^2$=0.9494), suggesting poor $K_d$ accuracy. The reverse titration of OTA with 4QI-OTAA-13 followed a similar trend, with small decreases in fluorescence intensity, no wavelength shifts, decreasing ET and no observable isosbestic point (FIG. 15B). When fitted to linear and single-site saturation models, similar variability was observed ($R^2$=0.9023 and $R^2$=0.9045, respectively) and a $K_d$ could not be obtained. Thus, considering the poor $K_d$ accuracy of the first titration combined with the lack of binding observed in the second titration, there does not appear to be significant OTA binding to 4QI-OTAA-13.

Figure 16:
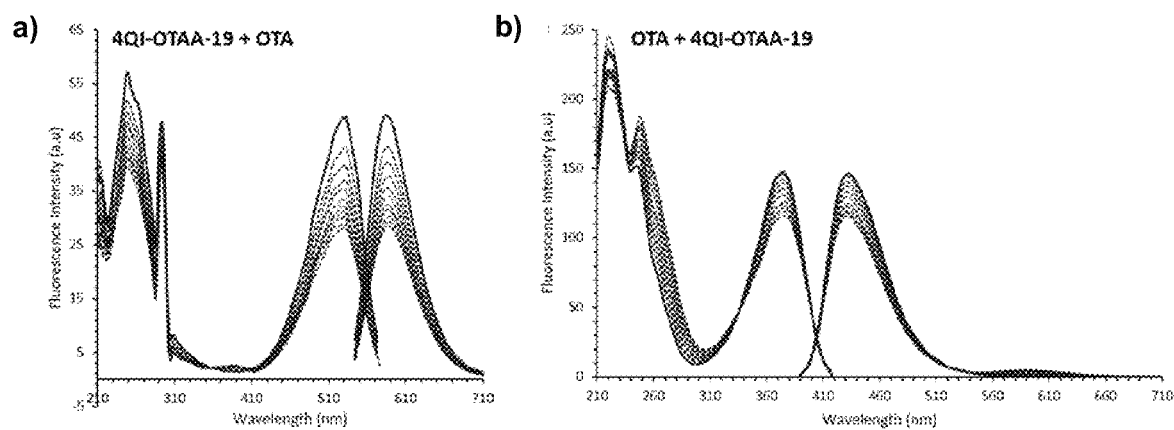
FIG. 16 shows fluorescence titration of (a) 1 µM 4QI-OTA-19 with 2 eq. OTA and (b) 1 µM OTA with 2 eq. 4QI-OTAA-19 both in 10% OTABB diluted with $H_2O$.

Titration of 4QI-OTAA-19 with OTA caused pronounced decreases in 4QI fluorescence intensity which decreased in magnitude and plateaued at approximately 2 equivalents of OTA, corresponding to a 42% decrease in fluorescence intensity (FIG. 16A). The binding data from this titration closely fit a single-site saturation binding model ($R^2$=0.9979) and yielded a $K_d$ of 1.0 t 0.1 μM. Regarding the reverse titration, OTA fluorescence intensity decreased with the addition of 4QI-OTAA-19 with slight shifts in $\lambda_{ex}$ and $\lambda_{em}$ maxima (FIG. 16B). OTA ET intensity also increased throughout the titration with a clear isosbestic point at 330 nm. Interestingly, this binding data did not closely fit a single-site saturation model ($R^2$=0.9888) and yielded high, imprecise $K_d$ of 24.5±31.6 µM. Based on these results it is clear that OTA binds 4QI-OTAA-19 with measurable affinity, and again differences in fluorophore sensitivity may account for the discrepancies in the calculated $K_d$ values.

TABLE 9

Experimental fluorescence, binding, ET and structural data for the mOTAA series.

| mOTAA | $K_d{}^a$ (µM) | % displacement[b] | $ETR_{GQ}$ | GQ |
|---|---|---|---|---|
| 4QI-OTAA-Free | 3.4 ± 0.3 | 20 | 1.604 | parallel |
| 4QI-OTAA-E | NAB[c] | 10 | 1.409 | parallel |
| 4QI-OTAA-13 | NAB | 6 | 1.269 | hybrid |
| 4QI-OTAA-19 | 1.0 ± 0.1 | 42 | 1.059 | hybrid |

[a]Resulting from the most sensitive titration.
[b]% displacement = ($E_{initial}$ − $E_{plateau}$)/$E_{initial}$ × 100.
[c]No apparent binding.

The fluorescence and binding data gathered in this section along with relevant CD data are summarized in Table 9. Based on the $K_d$ values calculated for 4QI-OTAA-19 and 4QI-OTAA-Free, these mOTAA bound OTA with nearly the same or slightly reduced affinity than the native aptamer (1.1 µM). (Cruz-Aguado et al., 2008) In both of these cases, the fluorescence intensity of 4QI decreased alongside decreased ET to 4QI, with increased ET to OTA. Therefore, it is proposed that OTA binding caused displacement of 4QI from a G-tetrad surface and into more polar, less rigid surrounding media. The % displacement observed in 4QI-OTAA-Free was relatively inefficient when compared to 4QI-OTAA-19. This effect could result from the relatively poor binding affinity of 4QI-OTAA-Free, its increased stacking strength or perhaps because of differences in how OTA binds a parallel versus hybrid GQ structure.

Interestingly, OTA was unable to bind 4QI-OTAA-E or 4QI-OTAA-13, resulting in small % displacement attributed to sample dilution. Since OTA bound to the parallel GQ of 4QI-OTAA-Free but not to that of 4QI-OTAA-E, this lack of binding suggests that the aptamer tails are crucial for OTA binding. This same idea translates to 4QI-OTAA-13, where the observed lack of binding was likely not due to an altered GQ structure, but rather the specific site of modification. Recall that previous studies showed that replacing $G_{13}$ within the bottom loop of OTAA with another native nucleotide did not inhibit OTA binding. Therefore, based on the lack of binding observed with 4QI-OTAA-13, backbone integrity and/or hydrogen bonding within this bottom loop may be crucial for OTA binding.

These results show that OTA detection can be achieved using a merocyanine dye strategically incorporated within OTAA. Melting temperature and CD analysis illustrated how modification type and location impacts OTAA structure. Specifically, 4QI-OTAA-Free and 4QI-OTAA-E reversed the GQ topology from parallel to antiparallel. Internal-modification resulted in hybrid parallel-antiparallel GQs, where incorporation at $G_{13}$ and $T_{19}$ favoured antiparallel and parallel character, respectively. The fluorescence of 4QI-OTAA-Free was reduced by 20% with OTA binding, as evidenced by CD and fluorescence titration, with a K of 3.4±0.3 µM. Both 4QI-OTAA-E and 4QI-OTAA-13 did not show fluorescence or CD responses which would indicate strong OTA binding affinity. However, OTA bound the 4QI-OTAA-19 with a $K_d$ of 1.0±0.1 µM, corresponding to a 42% decrease in fluorescence emission. Accordingly, this binding event caused reversal from a hybrid to native GQ structure. Finally, by comparing the binding affinities of the internal-versus end-label mOTAA, there is evidence to support the notion that OTA binds the bottom face of the aptamer. Altogether, these results highlight the utility of merocyanine dyes in a DNA aptasensor for small-molecule detection.

Example 4: Ligand-Induced G-Quadruplex Polymorphism as a Conformation-Al Switch for a Label-Free Aptasensor Platform G-Quadruplexes (GQs) serve as popular construction components for DNA aptasensors and typically rely on duplex→GQ exchange to activate a sensing mechanism. However, this platform requires optimization of the complementary strand for target-mediated strand displacement and involves complex equilibria between the duplex and the GQ-target complex. Herein it is highlighted that GQ polymorphism as an alternative conformational switch for label-free aptasensor detection. Utilizing the ochratoxin A (OTA) binding aptamer (OTABA) that folds into an antiparallel GQ in the absence and presence of its target OTA, it is demonstrated that cationic fluorogenic hemicyanine dyes convert the antiparallel GQ of OTABA into a parallel or hybrid topology depending on dye structure that is accompanied by a light-up dye emission response. The GQ-specific dye thioflavin T (ThT) also binds OTABA to exhibit impressive light-up emission but fails to induce a conformational change in the antiparallel fold of the aptamer. Subsequent additions of OTA to the aptamer-dye complexes demonstrate efficient displacement of the hemicyanines with turn-off emission, while ThT is poorly displaced from the aptamer. These results are the first to exemplify ligand-induced GQ polymorphism as a label-free aptasensor mechanism.

Aptamers are nucleic acid biosensors consisting of synthetic oligonucleotides generated by an in vitro selection process (or SELEX) to afford single strands that bind target molecules with high affinity and specificity. (Ellington et al, 1990; Tuerk et al, 1990; Bunka et al., 2006; Du et al., 2017; Akki et al., 2018) A common "read-out configuration" is the G-quadruplex (GQ) DNA based strategy that is employed when a selected G-rich aptamer folds into a GQ topology upon target binding. (Du et al., 2017) GQs are four-stranded structures containing stacked G-tetrads that are connected via loop residues. The GQ topology is well-suited for binding various metal cations (Li et al., 2010; Blanchard et al., 2016; Zhou et al., 2017), which electrostatically bind to the carbonyl oxygen of the quartet guanines. They also provide a scaffold for protein targets (Russo Krauss et al., 2012; Cservenyi et al., 2016), and the nearly planar G-tetrad surfaces provide good receptors for conjugated aromatic small molecules and macrocycles. (Vummidi et al., 2013)

To turn aptamer-binding events into read-out signals, the aptamer typically undergoes a significant conformational change upon target binding to activate a sensing mechanism. (Li et al., 2010; Akki et al., 2018) For the GQ strategy a common platform is duplex-GQ exchange (Alerbti et al., 2003), in which the aptamer is base-paired with a complementary strand to afford a duplex structure. Displacement of the complementary oligo from the aptamer mediated by formation of the GQ-target complex activates the read-out signal. (Alberti et al., 2003; Cruz-Aguado et al., 2008; Sproviero et al., 2014; Li et al., 2010) An issue with this platform is the need for optimization of the complementary strand for displacement that involves complex equilibria between duplex and the GQ-target complex.

An alternative conformational switching mechanism could involve the tendency of GQs to undergo polymorphism. (Deore et al., 2018; Prisian et al., 2008) Indeed, intramolecular GQ nucleic acids can adopt a variety of strand orientations (antiparallel, parallel, or hybrid) that are influenced by cation nature (Sproviero et al., 2015), molecular crowding agents (Largy et al., 2016) and ligands (Buscaglia et al., 2013). Herein, it is demonstrated the concept of ligand-induced GQ polymorphism as a conformational switch for target-mediated dye displacement in a label-free fluorescent aptasensor platform (Marchand et al., 2015) using the GQ-target complex produced by the fungal carcinogen ochratoxin A (OTA) (Du et al., 2013; Manderville et al., 2017) and its 31-mer aptamer (OTABA, see below). (Lee et al., 2008) The 31-mer OTABA binds OTA in an antiparallel topology with an anticlockwise loop progression connecting two G-tetrads (Fadock et al., 2017) and serves as a proof-of-concept aptamer for small molecule detection. (McKeague et al., 2015) Three cationic fluorogenic dyes were used as signalling ligands and include the commercial dye Thioflavin T (ThT), with acceptor (shown in red) and donor (in blue) directly attached to afford a twisted biphenyl-like structure, that is widely used to selectively detect GQ nucleic acids due to its impressive light-up emission response upon GQ binding. (Mohanty et al., 2013; Liu et al., 2014; Renaud de la Faverie et al., 2014) The 4-quinolinium-indole (4QI, 1-2) derivative belongs to a family of cyanine-styryl dyes that are utilized for fluorescent DNA staining. (Bohländer et al., 2013) The coumarin-hemicyanine hybrid (BtC) has also been used to fluorescently stain GQ topologies produced by the 22-mer human telomeric (HTelo) DNA (Yan et al., 2015) and the hemin binding aptamer (PS2.M). (Deore et al., 2019)

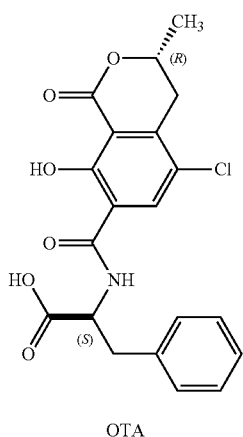
OTA

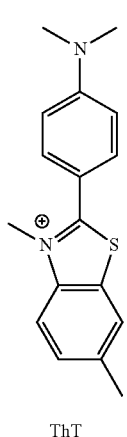
ThT

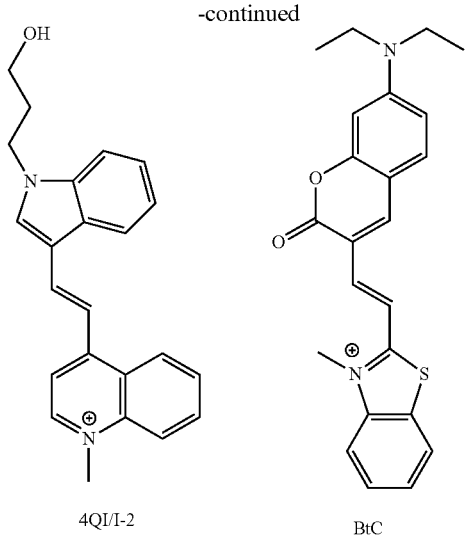
4QI/I-2      BtC

5'-GATCGGGTGTGGGTGGCGTAAAGGGAGCATC-3'

31-mer OTABA

Dye interaction with OTABA and subsequent displacement by OTA was initially investigated using fluorescence spectroscopy (FIG. 17) in the previously optimized OTA binding buffer. (Fadock et al., 2017) Additions of OTABA (up to 1.5 equiv.) to the dye (6 µM) caused dose-dependent increases in ligand emission at 488 nm for ThT (240-fold increase at 1.5 equiv. OTABA, FIG. 17a), 605 nm for the 4QI (42-fold, FIG. 17b) and 640 nm for BtC (8-fold, FIG. 17c). The excitation spectrum of each dye:OTABA mixture also displayed an energy transfer (ET) band at ~256 nm, which is indicative of dye stacking interactions with the G-tetrad within the GQ-dye complex. (Dumas et al., 2011) Plots of relative increase in dye fluorescence intensities upon OTABA binding afforded apparent dissociation constants ($K_d$) of 10.9 µM (ThT), 2.5 µM (4QI) and 3.2 µM (BtC), highlighting stronger aptamer affinity by the hemicyanines compared to ThT.

For dye displacement from the aptamer mediated by OTA, a 2:1 dye:OTABA mixture (12:6 µM) was treated with aliquots of OTA up to 1.5 equiv. (9 µM). Under these conditions, ThT was poorly displaced from the aptamer, displaying only a 6% drop in emission intensity (FIG. 17d). Better responses were observed for 4QI (28% displacement, FIG. 2e) and BtC (52% displacement, FIG. 17f). Significant differences in the ability of OTA to displace the dyes from the aptamer was not anticipated. Furthermore, given the relative binding affinities of the dyes for OTABA, ThT was expected to display the greatest ease of displacement. Clearly the ability of OTA to displace the dyes from the aptamer had little to do with the dye aptamer binding affinity.

To determine the analytical potential of the dye displacement assay, the 2:1 dye:OTABA starting mixture was optimized and the OTA titrations were repeated using 0.5 µM OTABA in the presence of 1 µM dye. A representative titration for BtC displacement mediated by OTA is displayed in FIG. 18. Additions of OTA up to 1.5 equiv (0.75 µM) caused 93% BtC displacement, as evidenced by the loss of emission intensity for the aptamer-bound BtC at 640 nm, coupled with the loss of the ET band at 256 nm for BtC stacking with the G-tetrad of the folded aptamer. The extent of BtC displacement (93%) considerably improved from the 52% displacement observed at the higher concentration regime (FIG. 17f). From the fluorescence displacement data an apparent dissociation constant ($K_d$)~112 nM (insert, FIG. 18) was determined for OTA binding to OTABA.

Additions of OTA to the 2:1 ThT:OTABA mixture (1:0.5 µM) also increased the drop in ThT emission intensity (23%, Figure S2a) compared to the high concentration regime (6%, FIG. 17b) and afforded a $K_d$ of 292 nM for OTA aptamer binding. Under the same conditions OTA caused 47% displacement of 4QI with an aptamer affinity ($K_d$) of 356 nM. From the OTA titrations involving hemicyanine dye displacement (4QI and BtC), a limit of detection (LoD)~15 nM (6 ng/mL) and a limit of quantification (LoQ)~45-47 nM (~18 ng/mL) were determined ($R^2$=0.95-0.99). In contrast, an LoD of 73 nM (29 ng/mL) and LoQ of 222 nM (89 ng/mL, $R^2$=0.85) was determined from the ThT displacement data. Superior sensitivity for OTA detection was obtained using the hemicyanine dyes that also exhibited significantly brighter emission intensity compared to ThT (1 µM) when bound to 0.5 µM OTABA in the starting aptamer-dye complex (intensity ratio of 1:5.6:15 for ThT:4QI:BtC, results are summarized in Table 10).

4QI:OTABA complex that adopts a parallel GQ topology, OTA additions caused loss in amplitude of the positive 260 nm peak, and formation of a distinct positive shoulder at ~290 nm (FIG. 19e), suggesting production of the antiparallel GQ topology required for OTA binding. Additions of OTA to the BtC:OTABA complex that is ascribed to an antiparallel-parallel hybrid topology, clearly converted the CD profile back into the antiparallel fold upon formation of the OTA:OTBA complex (FIG. 19f). Overall, the CD results demonstrated ligand-induced GQ polymorphism for OTABA and provided a rationale for the distinct differences in dye performance in the target-mediated displacement assays.

It was demonstrated that ThT binds OTABA without perturbing the antiparallel GQ topology, while the hemicyanines induce OTABA polymorphism and convert the native antiparallel GQ into the hybrid or parallel topology depending on dye structure (FIG. 20). Compared to ThT, the hemicyanines are larger π-planar compounds and a number of extended aromatic fluorophores are known to preferentially bind to parallel GQ structures, due in part, to favorable

TABLE 10

Fluorescence-based parameters for the dyes binding to OTABA and subsequent displacement by OTA

| | dye bound to OTABA | | | | | | dye displacement by OTA | | | | |
|---|---|---|---|---|---|---|---|---|---|---|---|
| dye | $\lambda_{ex}^a$ (nm) | $\lambda_{em}$ (nm) | $I_{rel}^b$ (B/F) | $I_{rel}$ dyes$^c$ | $K_d$ (µM)$^d$ | GQ topology | % D (6 → 0.5 µM)$^e$ | $K_d$ (nM)$^f$ | LoD (ng/mL) | LoQ (ng/mL) | GQ topology |
| ThT | 448 (412) | 488 | 240 | 1 | 10.9 ± 0.5 | antiparallel | 6-23 | 291.6 ± 43.2 | 29.3 | 88.8 | antiparallel |
| 4QI | 532 (493) | 605 | 42 | 5.6 | 2.5 ± 0.2 | parallel | 28-47 | 355.9 ± 15.2 | 6.0 | 18.1 | parallel |
| BtC | 580 (549) | 640 | 8 | 15 | 3.2 ± 0.3 | hybrid | 52-93 | 111.8 ± 8.9 | 6.2 | 18.7 | antiparallel |

In search of a possible rationale for the poor sensitivity displayed by ThT compared to the hemicyanine dyes, dye impact on the GQ topology produced by OTABA was explored using CD spectroscopy (FIG. 19). Native OTABA exhibits positive CD peaks at 290 and 240 nm and a negative peak at 260 nm, which is characteristic of the antiparallel fold. (Fadock et al., 2017) Addition of ThT had little impact on the antiparallel GQ, exhibiting only slight changes in the amplitudes of the three characteristic peaks (FIG. 19a). In sharp contrast, additions of 4QI led to loss of the antiparallel CD features and afforded a strong positive peak at ~260 nm (FIG. 19b), which is characteristic of the parallel GQ with the all anti-glycosidic conformation of the G-tetrads. (Prisian et al., 2008; Largy et al., 2016; Heddi et al., 2011) Addition of BtC to OTABA also caused the aptamer to adopt an alternative GQ fold (FIG. 19c). The strong positive peak at 293 nm for the antiparallel GQ of native OTABA shifted to 291 nm and contained a shoulder at ~275 nm. The negative peak at 260 nm decreased in amplitude considerably and shifted to 256 nm and was followed by a small positive peak at 247 nm. The CD profile adopted by OTABA in the presence of BtC strongly resembled the profile adopted by the extended H-Telo oligonucleotide that favors formation of a mixed parallel-antiparallel GQ (hybrid-2). (Dai et al., 2007)

Dye displacement mediated by OTA was also monitored by CD spectroscopy. Additions of OTA to the ThT:OTABA complex (12:6 µM) caused the amplitudes of the characteristic antiparallel peaks to increase (FIG. 19d). For the end-stacking interactions with the exposed planar G-tetrad of the parallel fold. (Nicoludis etal., 2012; Buscaglia et al, 2013; Vummidi et al., 2013) This outcome provides a conformational switch for hemicyanine dye displacement mediated by the target OTA and provides a clear application for ligand-induced GQ polymorphism. A major focus for the design of GQ-targeting ligands has been to visualize GQ structures in cellular environments (Manna et al., 2018), help establish their structure and function, and serve as possible chemotherapeutic agents. (Neidle et al., 2017; Hansel-Hertsch et al., 2017) An alternative focus is provided for GQ-targeting ligands as signaling molecules of specific GQ aptamer-target complexes important for diagnostic applications.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Akki, S. U.; Werth, C. J. Critical Review: DNA Aptasensors, Are They Ready for Monitoring Organic Pollutants in Natural and Treated Water Sources? *Environ. Sci. Technol.* 2018, 52, 8989-9007.

Alberti, P.; Mergny, J.-L. DNA Duplex-Quadruplex Exchange as the Basis for a Nanomolecular Machine. *Proc. Natl. Acad. Sci. USA* 2003, 100, 1569-1573.

Annamaria, R.; Derosa, M. C. Small-Molecule Binding Aptamers: Selection Strategies, Characterization, and Applications. *Front. Chem.* 2016, 4, Article 4.

Armitage, B. A. Cyanine Dye-DNA Interactions: Intercalation, Groove Binding, and Aggregation. *Top. Curr. Chem.* 2005, 253, 55-76.

Barthelmebs, L.; Jonca, J.; Hayat, A.; Prieto-Simon, B.; Marty, J.-L. Enzyme-Linked Aptamer Assays (ELAAs), Based on a Competition Format for a Rapid and Sensitive Detection of Ochratoxin A in Wine. *Food Control* 2011, 22, 737-743.

Blanchard, J. M.; Manderville, R. A. An Internal Charge Transfer-DNA Platform for Fluorescence Sensing of Divalent Metal Ions. *Chem. Commun.* 2016, 52, 9586-9588.

Blind, M.; Blank, M. Aptamer Selection Technology and Recent Advances. *Mol. Ther.—Nucleic Acids* 2015, 4 (1), 1-7.

Bohländer, P. R.; Wagenknecht, H. A. Synthesis and Evaluation of Cyanine-Styryl Dyes with Enhanced Photostability for Fluorescent DNA Staining. *Org. Biomol. Chem.* 2013, 11 (43), 7458-7462.

Bunka, D. H. J.; Stockley, P. G. Aptamers Come of Age—At Last. *Nat. Rev. Microbiol.* 2006, 4, 588-596.

Buscaglia, R.; Miller, M. C.; Dean, W. L.; Gray, R. D.; Lane, A. N.; Trent, J. O.; Chaires, J. B. Polyethylene Glycol Binding Alters Human Telomere G-Guadruplex Structure by Conformational Selection. *Nucleic Acids Res.* 2013, 41, 7934-7946.

Caruthers, M. H.; Barone, A. D.; Beaucage, S. L.; Dodds, D. R.; Fisher, E. F.; Mcbride, L. J.; Matteucci, M.; Stabinsky, Z.; Tang, J.-Y. Chemical Synthesis of Deoxyoligonucleotides by the Phosphoramidite Method. *Methods Enzymol.* 1987, 154, 287-313.

Coe, B. J.; Foxon, S. P.; Harper, E. C.; Harris, J. A.; Helliwell, M.; Raftery, J.; Asselberghs, I.; Clays, K.; Franz, E.; Brunschwig, B. S.; et al. The Syntheses, Structures and Nonlinear Optical and Related Properties of Salts with Julolidinyl Electron Donor Groups. *Dye. Pigment.* 2009, 82 (2), 171-186.

Cruz-Aguado, J. A.; Penner, G. Fluorescence Polarization Based Displacement Assay for the Determination of Small Molecules with Aptamers. *Anal. Chem.* 2008, 80, 8853-8855.

Cruz-Aguado, J. A.; Penner, G. Determination of Ochratoxin A with a DNA Aptamer. *J. Agric. Food Chem.* 2008, 56, 10456-11061.

Cservenyi, T. Z.; Van Riesen, A. J.; Berger, F. D.; Desoky, A.; Manderville, R. A. A Simple Molecular Rotor for Defining Nucleoside Environment Within a DNA Aptamer-Protein Complex. *ACS Chem. Biol.* 2016, 11, 2576-2582.

Dai, J.; Carver, M.; Punchihewa, C.; Jones, R. A.; Yang, D. Structure of the Hybrid-2 Type Intramolecular Human Telomeric G-Quadruplex in K+ Solution: Insights into Structure Polymorphism of the Human Telomeric Sequence. *Nucleic Acids Res.* 2007, 35, 4927-4940.

Deore, P. S.; Soldatov, D. V.; Manderville, R. A. A 5'-BODIPY End-label for Monitoring DNA Duplex-Quadruplex Exchange. *Sci. Rep.* 2018, 8, 16874.

Deore, P. S.; Coman, D. S.; Manderville, R. A. A Coumarin-Hemicyanine Hybrid as a Ratiometric Fluorescent Sensor of Microenvironment Proticity. *Chem. Commun.* 2019, 55, 3540-3543.

Du, Y.; Dong, S. Nucleic Acid Biosensors: Recent Advances and Perspectives. *Anal. Chem.* 2017, 89, 189-215.

Du, Y.; Li, B.; Wang, E. "Fitting" Makes "Sensing" Simple: Label-Free Detection Strategies Based on Nucleic Acid Aptamers. *Acc. Chem. Res.* 2013, 46, 203-213.

Dumas, A.; Luedtke, N. W. Highly Fluorescent Guanosine Mimics for Folding and Energy Transfer Studies. *Nucleic Acids Res.* 2011, 39 (15), 6825-6834.

Ellington, A. D.; Szostak, J. W. In vitro Selection of RNA Molecules that Bind Specific Ligands. *Nature* 1990, 346, 818-822.

Fadock, K. L.; Manderville, R. A.; Sharma, P.; Wetmore, S. D. Optimization of Fluorescent 8-Heteroaryl-Guanine Probes for Monitoring Protein-Mediated Duplex to G-Quadruplex Exchange. *Org. Biomol. Chem.* 2016, 14 (14), 4325-4544.

Fadock, K. L.; Manderville, R. A. DNA Aptamer-Target Binding Motif Revealed Using a Fluorescent Guanine Probe: Implications for Food Toxin Detection. *ACS Omega* 2017, 2, 4955-4963.

Ghimire, C.; Park, S.; Iida, K.; Yangyuoru, P.; Otomo, H.; Yu, Z.; Nagasawa, K.; Sugiyama, H.; Mao, H. Direct Quantification of Loop Interaction and T-T Stacking for G-Quadruplex Stability at the Submolecular Level. *J. Am. Chem. Soc.* 2014, 136 (44), 15537-15544.

Hansel-Hertsch, R.; Di Antonio, M.; Balasubramanian, S. DNA G-Quadruplexes in the Human Genome: Detection, Functions and Therapeutic Potential. *Nat. Rev. Mol. Cell Biol.* 2017, 18, 279-284.

Heddi, B.; Phan, A. T. Structure of Human Telomeric DNA in Crowded Solution. *J. Am. Chem. Soc.* 2011, 133, 9824-9833.

Hirayama, T.; Ishikawa, T.; Okaniwa, M.; Kakei, H.; Banno, H.; Yokota, A. Preparation of N,N-Dialkylimidazo[1,2-a]Pyrdine-2-Carboxamide Derivatives as Anticancer Agents. WO 2012008508, 2012.

Hong, P.; Li, W.; Li, J. Applications of Aptasensors in Clinical Diagnostics. *Sensors* 2012, 12 (2), 1181-1193.

IARC Working Group on the Evaluation of Carcinogenic Risks to Humans. *IARC Monographs on the Evaluation of Carcinogenic Risks to Humans: Volume 82: Some Traditional Herbal Medicines, Some Mycotoxins, Naphthalene and Styrene*; Lyon, 2002.

Jayasena, S. D. Aptamers: An Emerging Class of Molecules That Rival Antibodies in Diagnostics. *Clin. Chem.* 1999, 45 (9), 1628-1650.

Justino, C.; Duarte, A.; Rocha-Santos, T. Recent Progress in Biosensors for Environmental Monitoring: A Review. *Sensors* 2017, 17 (12), 2-25.

Karsisiotis, A. I.; Hessari, N. M. A.; Novellino, E.; Spada, G. P.; Randazzo, A.; Webba Da Silva, M. Topological Characterization of Nucleic Acid G-Quadruplexes by UV Absorption and Circular Dichroism. *Angew. Chemie—Int. Ed.* 2011, 50 (45), 10645-10648.

Kelly, J. A.; Feigon, J.; Yeates, T. O. Reconciliation of the X-Ray and NMR Structures of the Thrombin-Binding Aptamer d(GGTTGGTGTGGTTGG). *J. Mol. Biol.* 1996, 256 (3), 417-422.

Kong, D.-M. M.; Ma, Y.-E. E.; Wu, J.; Shen, H.-X. X. Discrimination of G-Quadruplexes from Duplex and Single-Stranded DNAs with Fluorescence and Energy-Transfer Fluorescence Spectra of Crystal Violet. *Chem.—A Eur. J.* 2009, 15 (4), 901-909.

Lane, A. N.; Chaires, J. B.; Gray, R. D.; Trent, J. O. Stability and Kinetics of G-Quadruplex Structures. *Nucleic Acids Res.* 2008, pp 5482-5515.

Largy, E.; Marchand, A.; Amrane, S.; Gabelica, V.; Mergny, J.-L. Quadruplex Turncoats: Cation-Dependent Folding and Stability of Quadruplex-DNA Double Switches. *J. Am. Chem. Soc.* 2016, 138, 2780-2792.

Lee, H. J.; Ryu, D. Significance of Ochratoxin A in Breakfast Cereals from the United States. *J. Agric. Food Chem.* 2015, 63, 9404-9409. (25) Cruz-Aguado, J. A.; Penner, G. Determination of ochratoxin A with a DNA aptamer. *J. Agric. Food Chem.* 2008, 56, 10456-10461.

Li, T.; Dong, S. J.; Wang, E. K. A Lead(II)-Driven DNA Molecular Device for Turn-On Fluorescence Detection of Lead(II) Ion with High Selectivity and Sensitivity. *J. Am. Chem. Soc.* 2010, 132, 13156-13157.

Li, D.; Song, S. P.; Fan, C. H. Target-Responsive Structural Switching for Nucleic Acid-Based Sensors. *Acc. Chem. Res.* 2010, 43, 631-641.

Liu, L.; Shao, Y.; Peng, J.; Huang, C.; Liu, H; Zhang, L. Molecular Rotor-Based Fluorescent Probe for Selective Recognition of Hybrid G-Quadruplex and as a K+ Sensor. *Anal. Chem.* 2014, 86, 1622-1631.

Macaya, R. F.; Schultze, P.; Smith, F. W.; Roe, J. A.; Feigon, J. Thrombin-Binding DNA Aptamer Forms a Unimolecular Quadruplex Structure in Solution. *Proc. Natl. Acad. Sci.* 1993, 90 (8), 3745-3749.

Manderville, R. A.; Wetmore, S. D. Mutagenicity of Ochratoxin A: Role for a Carbon-Linked C8-Deoxyguanosine Adduct? *J. Agric. Food Chem.* 2017, 65, 7097-7105.

Manna, S.; Srivatsan, S. G. Fluorescence-Based Tools to Probe G-Quadruplexes in Cell-Free and Cellular Environments. *RSC Adv.* 2018, 8, 25673-25694.

Marchand, A.; Granzhan, A.; Iida, K.; Tsushima, Y.; Ma, Y.; Nagasawa, K.; Teulade-Fichou, M.-P.; Gabelica, V. Ligand-Induced Conformational Changes with Cation Ejection upon Binding to Human Telomeric DNA G-Quadruplexes. *J. Am. Chem. Soc.* 2015, 137, 750-756.

McKeague, M.; De Girolamo, A.; Valenzano, S.; Pascale, M.; Ruscito, A.; Velu, R.; Frost, N. R.; Hill, K.; Smith, M.; McConnell, E. M.; DeRosa, M. C. Comprehensive Analytical Comparison of Strategies used for Small Molecule Aptamer Evaluation. *Anal. Chem.* 2015, 87, 8608-8612.

McKeague, M.; Velu, R.; Hill, K.; Bardóczy, V.; Mészáros, T.; DeRosa, M. C. Selection and Characterization of a Novel DNA Aptamer for Label-Free Fluorescence Biosensing of Ochratoxin A. *Toxins (Basel).* 2014, 6 (8), 2435-2452.

Modh et al., Aptamer-Modified Magnetic Beads in Biosensing. *Sensors,* 2018, 18, 1041.

Mohanty, J.; Barooah, N.; Dhamodharan, V.; Harikrishna, S.; Pradeepkumar, P. I.; Bhasikuttan, A. C. Thiolavin T as an Efficient Inducer and Selective Fluorescent Sensor for the Human Telomeric G-Quadruplex DNA. *J. Am. Chem. Soc.* 2013, 135, 367-376.

Naik, P. N.; Khan, A.; Kusurkar, R. S. Intramolecular Diels-Alder Reaction for the Synthesis of Tetracyclic Carbazoles and Isocanthines. *Tetrahedron* 2013, 69 (50), 10733-10738.

Neidle, S. Quadruplex Nucleic Acids as Targets for Anticancer Therapeutics. *Nat. Rev. Chem.* 2017, 1, 0041.

Nicoludis, J. M.; Miller, S. T.; Jeffrey, P. D.; Barrett, S. P.; Rablen, P. R.; Lawton, T. J.; Yatsunyk, L. A. Optimized End-Stacking Provides Specificity on N-Methyl Mesoporphyrin IX for Human Telomeric G-Quadruplex DNA. *J. Am. Chem. Soc.* 2012, 134, 20446-20456.

Padmanabhan, K.; Padmanabhan, K. P.; Ferrara, J. D.; Sadler, J. E.; Tulinsky, A. The Structure of Alpha-Thrombin Inhibited by a 15-Mer Single-Stranded DNA Aptamer. *J. Biol. Chem.* 1993, 268 (24), 17651-17654.

Padmanabhan, K.; Tulinsky, A. An Ambiguous Structure of a DNA 15-Mer Thrombin Complex. *Acta. Crystallogr. D. Biol. Crystallogr.* 1996, 52 (2), 272-282.

Pagano, B.; Martino, L.; Randazzo, A.; Giancola, C. Stability and Binding Properties of a Modified Thrombin Binding Aptamer. *Biophys. J.* 2008, 94 (2), 562-569.

Pfohl-Leszkowicz, A.; Manderville, R. A. Ochratoxin A: An Overview on Toxicity and Carcinogenicity in Animals and Humans. *Mol. Nutr. Food Res.* 2007, 51 (1), 61-99.

Pohland, A. E.; Nesheim, S.; Friedman, L. Ochratoxin A: A Review. *Pure Appl. Chem* 1992, 64 (7), 1029-1046.

Prisian, I.; Lah, J.; Vesnaver, G. Diverse Polymorphism of G-Quadruplexes as a Kinetic Phenomenon. *J. Am. Chem. Soc.* 2008, 130, 14161-14169.

Renaud de la Faverie, A.; Guedin, A.; Bedrat, A.; Yatsunyk, L. A.; Mergny, J. L. Thioflavin T as a Fluorescence Light-up Probe for G4 Formation. *Nucleic Acids Res.* 2014, 42, e65.

Russo Krauss, I.; Merlino, A.; Randazzo, A.; Novellino, E.; Mazzarella, L.; Sica, F. High-Resolution Structures of Two Complexes between Thrombin and Thrombin-Binding Aptamer Shed Light on the Role of Cations in the Aptamer Inhibitory Activity. *Nucleic Acids Res.* 2012, 40 (16), 8119-8128.

Sasaki, S.; Drummen, G. P. C.; Konishi, G. Recent Advances in Twisted Intramolecular Charge Transfer (TICT) Fluorescence and Related Phenomena in Materials Chemistry. *J. Mater. Chemsitry C* 2016, 4 (14), 2731-2743.

Smimov, I.; Shafer, R. H. Effect of Loop Sequence and Size on DNA Aptamer Stability. *Biochemistry* 2000, 39 (6), 1462-1468.

Sproviero, M.; Fadock, K. L.; Witham, A. A.; Manderville, R. A.; Sharma, P.; Wetmore, S. D. Electronic Tuning of Fluorescent 8-Aryl-Guanine Probes for Monitoring DNA Duplex-Quadruplex Exchange. *Chem. Sci.* 2014, 5, 788-796.

Sproviero, M.; Fadock, K. L.; Witham, A. A.; Manderville, R. A. Positional Impact of Fluorescently Modified G-Tetrads within Polymorphic Human Telomeric G-Quadruplex Structures. *ACS Chem. Biol.* 2015, 10, 1311-1318.

Turner, Anthony P. F.; Wilson, G. S. *Biosensors Fundamentals and Applications*; Oxford University Press: New York, 1989; Vol. 53.

Tuerk, C.; Gold, L. Systematic evolution of ligands by exponential enrichment: RNA ligands to bacteriophage T4 DNA polymerase. *Science* 1990, 249, 505-510.

Van Riesen, A. J.; Fadock, K. L.; Deore, P. S.; Desoky, A.; Manderville, R. A.; Sowlati-Hashjin, S.; Wetmore, S. D. Manipulation of a DNA Aptamer-Protein Binding Site through Arylation of Internal Guanine Residues. *Org. Biomol. Chem.* 2018, 16 (20), 3831-3840.

Vummidi, B. R.; Alzeer, J.; Luedtke, N. W. Fluorescent Probes for G-Quadruplex Structures. *Chem. Bio. Chem.* 2013, 14, 540-558.

Wang, K. Y.; Bolton, P. H.; Krawczyk, S. H.; Bischofberger, N.; Swaminathan, S. The Tertiary Structure of a DNA Aptamer Which Binds to and Inhibits Thrombin Determines Activity. *Biochemistry* 1993, 32 (42), 11285-11292.

Wang, K. Y.; Bolton, P. H.; McCurdy, S.; Shea, R. G.; Swaminathan, S. A DNA Aptamer Which Binds to and Inhibits Thrombin Exhibits a New Structural Motif for DNA. *Biochemistry* 1993, 32 (8), 1899-1904.

Wang, R. E.; Zhang, Y.; Cai, J.; Cai, W.; Gao, T. Aptamer-Based Fluorescent Biosensors. *Curr. Med. Chem.* 2011, 18 (27), 4175-4184.

Xu, W.; Min Chan, K.; Kool, E. T. Fluorescent Nucleobases as Tools for Studying DNA and RNA. *Nat. Chem.* 2017, 9, 1043-1055.

Yan, J.-W.; Tian, Y.-G.; Tan, J.-H.; Huang, Z.-S. Colorimetric and Fluorescence Detection of G-Quadruplex Nucleic Acids with a Coumarin-Benzothiazole Probe. *Analyst* 2015, 140, 7146-7149.

Zhou, W.; Saran, R.; Liu, J. Metal Sensing by DNA. *Chem. Rev.* 2017, 117, 8272-8325.

---

The invention claimed is:

1. A fluorescent compound of Formula 1,

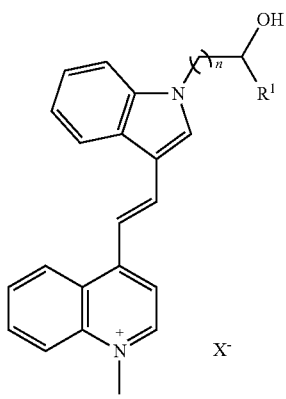

I

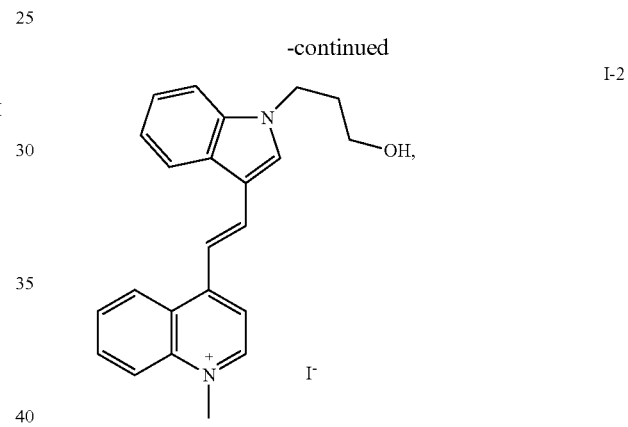

wherein $R^1$ is selected from H and $CH_2OH$;
$X^-$ is a suitable counterion; and
n=1 or 2.

2. The fluorescent compound of claim 1, wherein the compound is selected from the group consisting of

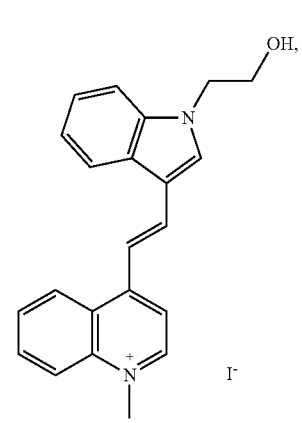

-continued

I-4

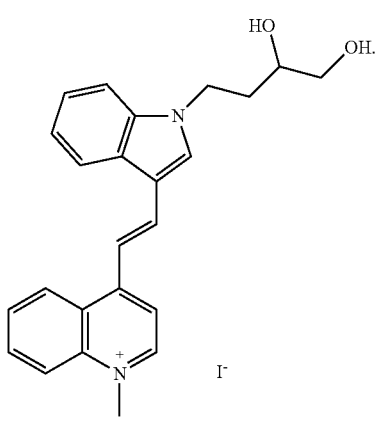

3. A fluorescent phosphoramidite of Formula II

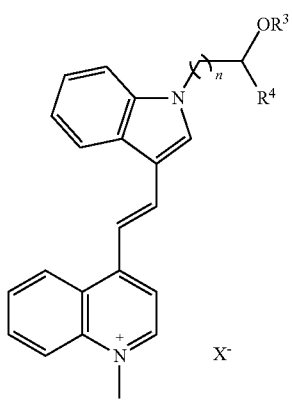

II wherein R³ is selected from a protective group and a phosphoramidite functionality;
R⁴ is selected from the group consisting of H and —CH₂Phosphoramidite;
n=1 or 2;
X⁻ is a suitable counterion;
when R⁴ is H, R³ is the phosphoramidite functionality; and when R⁴ is —CH₂Phosphoramidite, R³ is the protective group.

4. The fluorescent phosphoramidite of claim 3, wherein the protective group is an acid-labile protective group.

5. The fluorescent phosphoramidite of claim 4, wherein the acid-labile protective group is selected from the group consisting of dimethoxytrityl (DMT), and 5'-O-2,7-dimethylpixyl

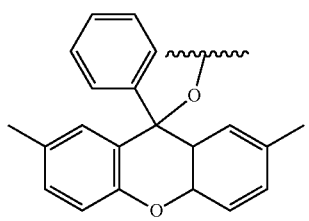

(DMPx).

6. The fluorescent phosphoramidite of claim 3, wherein the phosphoramidite functionality is

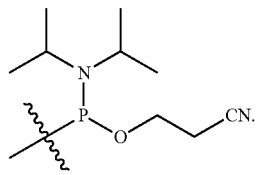 [SMILES: *P(OCCC#N)N(C(C)C)C(C)C]

7. The fluorescent phosphoramidite of claim 3, wherein the —CH₂Phosphoramidite is

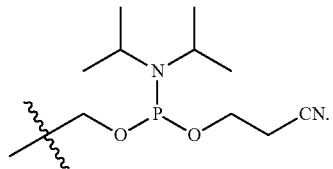 [SMILES: *COP(OCCC#N)N(C(C)C)C(C)C]

8. The fluorescent phosphoramidite of claim 3, wherein the fluorescent phosphoramidite is selected from the group consisting of

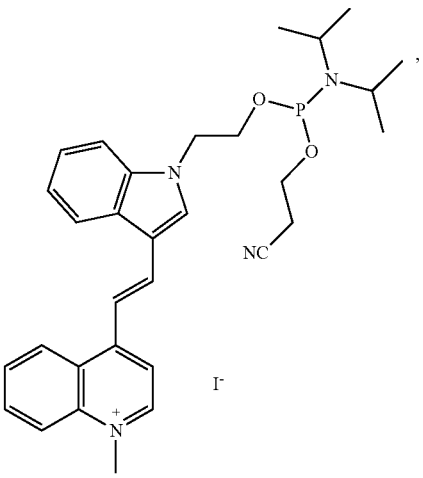

II-1

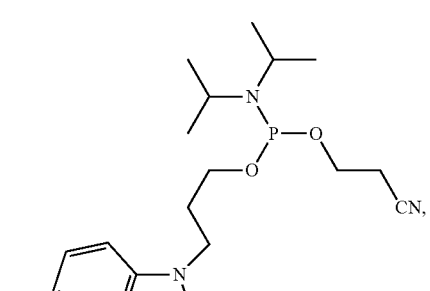

II-2

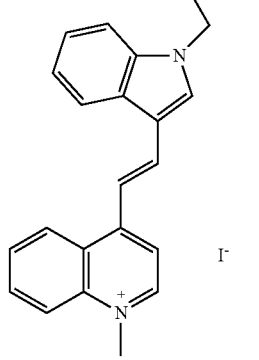

-continued

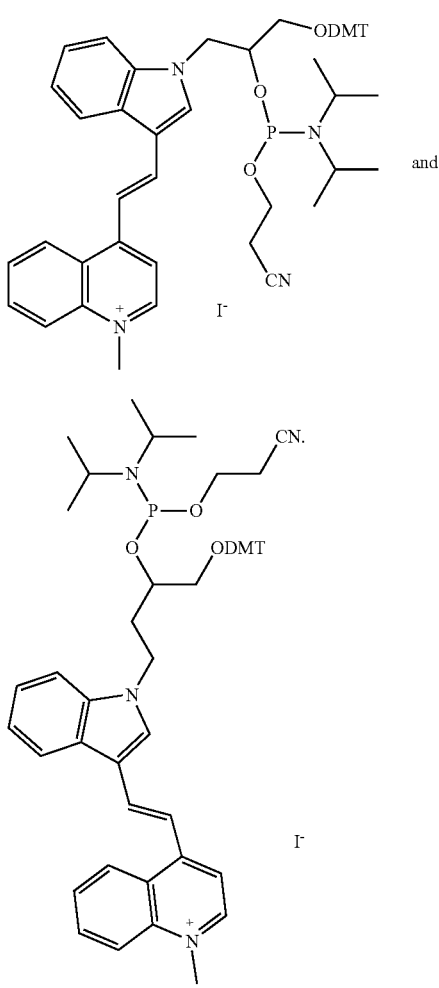

II-3 and

II-4

9. A compound of Formula III

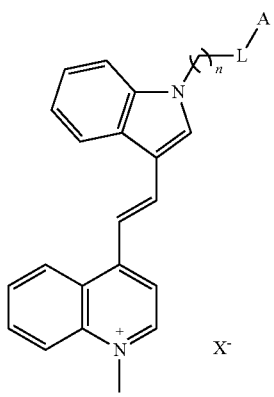

wherein L is an optional linker;
A is a substrate;
X⁻ is an optional suitable counterion; and
n is an integer between 1 to 4; wherein said substrate is a binding agent selected from the group consisting of an aptamer, a ligand or an antibody; a biomolecule selected from the group consisting of a polypeptide, a polynucleotide, a polysaccharide, a lipid, a carbohydrate, and an organic molecule; or a drug.

10. The compound for Formula III of claim 9, wherein the substrate comprises a binding agent that binds to a target.

11. The compound of claim 10, wherein the substrate is an aptamer, ligand or antibody.

12. The compound of claim 9, wherein the substrate comprises a polynucleotide and the compound is a fluorescently labelled polynucleotide of structure selected from Formulae V, and VI, VII

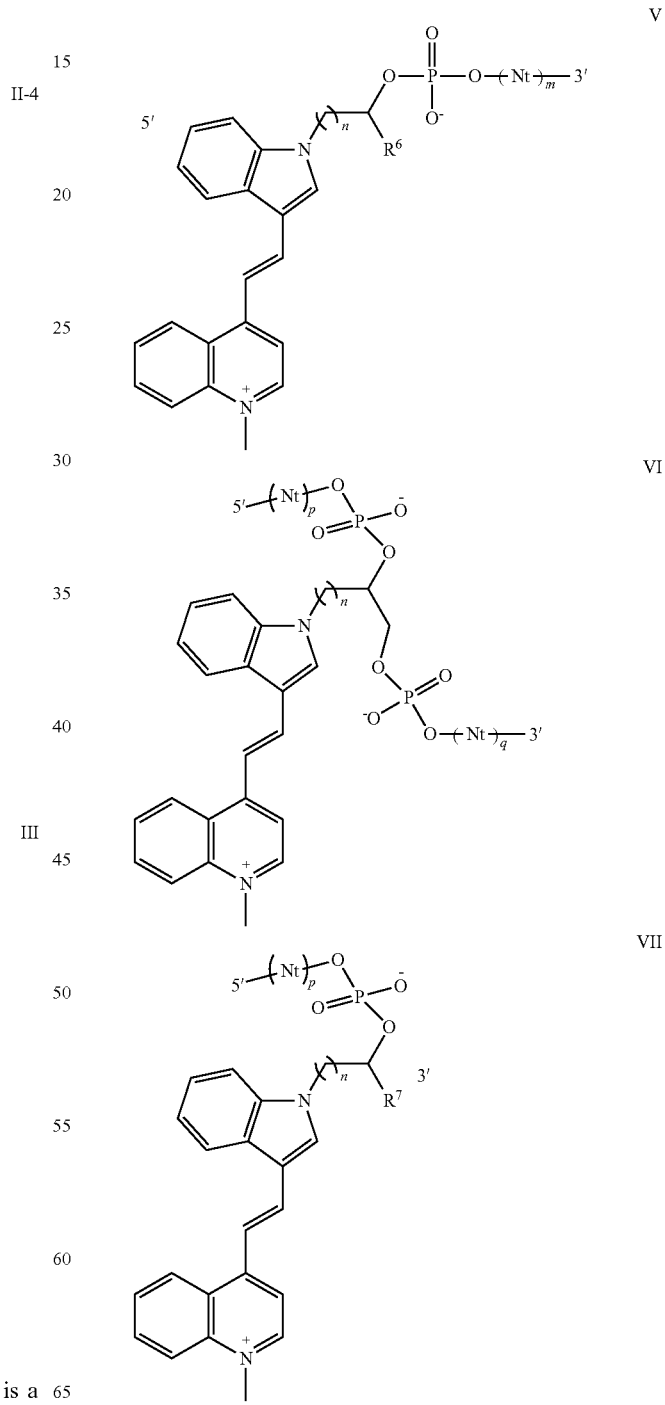

wherein $R^6$ and $R^7$ are independently selected from H and $CH_2OH$;

n=1 or 2;

m, p and q are independently an integer between 1 and 1000; and

Nt is a nucleotide.

13. The compound of claim 12, wherein the polynucleotide is an aptamer that binds to a target.

14. A method for detecting a target in a sample, the method comprising:

contacting the sample with the fluorescent compound of claim 1 and a binding agent for the target, wherein binding of the binding agent to the target changes the optical properties of the fluorescent compound in the sample; and detecting a change in the optical properties of the fluorescent compound in the sample.

15. The method of claim 14, wherein the binding agent and the fluorescent compound are combined prior to contacting the sample.

16. The method of claim 14 wherein the binding agent is a DNA aptamer.

17. A method for detecting a target in a sample, the method comprising:

contacting the sample with the compound of claim 10 wherein the binding agent is capable of binding to the target; and detecting the compound bound to the target in the sample.

18. The method of claim 17, wherein detecting the compound bound to the target in the sample comprises detecting a change in one or more optical properties of the compound.

19. The method of claim 18, wherein detecting the change in the one or more optical properties of the compound comprises detecting a change in absorbance, fluorescence, fluorescence polarization or circular dichroism relative to a control.

20. The method of claim 19, wherein detecting the compound bound to the target comprises detecting an emission at one or more wavelengths between about 550 nm to 650 nm.

* * * * *

UNITED STATES PATENT AND TRADEMARK OFFICE
CERTIFICATE OF CORRECTION

PATENT NO. : 11,215,619 B2
APPLICATION NO. : 16/884927
DATED : January 4, 2022
INVENTOR(S) : Richard Manderville et al.

Page 1 of 1

It is certified that error appears in the above-identified patent and that said Letters Patent is hereby corrected as shown below:

In the Claims

1. Column 56, Line 11, Claim 12, "Formulae V, and VI, VII" should read --Formulae V, VI, and VII--

2. Column 58, Line 16, Claim 20, "The method of claim 19" should read --The method of claim 17--

Signed and Sealed this
Thirtieth Day of May, 2023

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Synthetic construct

<400> SEQUENCE: 1
ggttggtgtg gttgg                                                     15

<210> SEQ ID NO 2
<211> LENGTH: 31
<212> TYPE: DNA
<213> ORGANISM: Artificial Sequence
<220> FEATURE:
<223> OTHER INFORMATION: Synthetic construct

<400> SEQUENCE: 2
gatcgggtgt gggtggcgta aagggagcat c                                   31